(12) United States Patent
Chapman-McQuiston et al.

(10) Patent No.: US 10,991,466 B2
(45) Date of Patent: Apr. 27, 2021

(54) DISTRIBUTED CORRELATION AND ANALYSIS OF PATIENT THERAPY DATA

(71) Applicant: SAS Institute Inc., Cary, NC (US)

(72) Inventors: Emily Chapman-McQuiston, Cary, NC (US); Diane Emerton, Cary, NC (US); Ruth Baldasaro, Cary, NC (US); Daniel Kelly, Raleigh, NC (US)

(73) Assignee: SAS INSTITUTE INC., Cary, NC (US)

( * ) Notice: Subject to any disclaimer, the term of this patent is extended or adjusted under 35 U.S.C. 154(b) by 1373 days.

(21) Appl. No.: 15/145,222

(22) Filed: May 3, 2016

(65) Prior Publication Data

US 2016/0342742 A1    Nov. 24, 2016

Related U.S. Application Data

(60) Provisional application No. 62/156,806, filed on May 4, 2015.

(51) Int. Cl.
  *G16H 50/70*    (2018.01)
  *G16H 10/60*    (2018.01)
(52) U.S. Cl.
  CPC ............. *G16H 50/70* (2018.01); *G16H 10/60* (2018.01)
(58) Field of Classification Search
  CPC ............................................... G06Q 50/22–24
  See application file for complete search history.

(56) References Cited

U.S. PATENT DOCUMENTS

| 7,386,506 B2 | 6/2008 | Aoki et al. |
| 2001/0023419 A1* | 9/2001 | Lapointe ................ G16H 50/20 |
| | | 706/15 |
| 2003/0167189 A1* | 9/2003 | Lutgen .................. G06F 19/326 |
| | | 705/3 |
| 2003/0229519 A1 | 12/2003 | Eidex et al. |
| 2004/0122790 A1* | 6/2004 | Walker .................. G06F 19/321 |
| 2005/0181386 A1* | 8/2005 | Diamond ........... G01N 33/6893 |
| | | 435/6.11 |

(Continued)

FOREIGN PATENT DOCUMENTS

WO    2013070983    5/2013

OTHER PUBLICATIONS

Aral et al., "A prescription fraud detection model", Comput Methods Programs Biomed., Elsevier, Apr. 2012, 10 pages.

*Primary Examiner* — Robert A Sorey
(74) *Attorney, Agent, or Firm* — Kacvinsky Daisak Bluni PLLC

(57)    ABSTRACT

An apparatus includes a processor and storage to store instructions that cause the processor to identify at least one correlation between a diagnosis group and a medication class for each patient of a first set of patients to derive a set of models for each diagnosis group that correlates the diagnosis group to at least one medication class based on the at least one identified correlation; and for each patient of a second set of patients, employ each model of each set of models to make at least one prediction of at least one diagnosis group as indicated in the corresponding diagnosis group record based on at least one medication class indicated in the corresponding medication class record, and compare the at least one prediction to the corresponding diagnosis group record to derive a tally of at least one of true positives or false positives for each prediction.

27 Claims, 24 Drawing Sheets

(56) References Cited

U.S. PATENT DOCUMENTS

| | | | |
|---|---|---|---|
| 2008/0171916 A1* | 7/2008 | Feder | G16H 50/70 600/300 |
| 2012/0230560 A1 | 9/2012 | Spitz et al. | |
| 2015/0046181 A1 | 2/2015 | Adjaoute | |

* cited by examiner

500

```
┌─────────────────────────────────────────────────────────┐
│ RECEIVE GRID STATUS INFORMATION INCLUDING A PROJECT     │
│ STATUS OF A PORTION OF A PROJECT BEING EXECUTED BY A    │
│ NODE IN THE COMMUNICATIONS GRID                         │
│                        502                              │
└─────────────────────────────────────────────────────────┘
                            ↓
┌─────────────────────────────────────────────────────────┐
│           STORE THE GRID STATUS INFORMATION             │
│                        504                              │
└─────────────────────────────────────────────────────────┘
                            ↓
┌─────────────────────────────────────────────────────────┐
│ RECEIVE A FAILURE COMMUNICATION CORRESPONDING TO A      │
│ NODE IN THE COMMUNICATIONS GRID                         │
│                        506                              │
└─────────────────────────────────────────────────────────┘
                            ↓
┌─────────────────────────────────────────────────────────┐
│ REASSIGN A NODE OR A PORTION OF THE PROJECT BEING       │
│ EXECUTED BY THE FAILED NODE                             │
│                        508                              │
└─────────────────────────────────────────────────────────┘
                            ↓
┌─────────────────────────────────────────────────────────┐
│ RECEIVE UPDATED GRID STATUS INFORMATION BASED ON THE    │
│ REASSIGNMENT                                            │
│                        510                              │
└─────────────────────────────────────────────────────────┘
                            ↓
┌─────────────────────────────────────────────────────────┐
│ TRANSMIT A SET OF INSTRUCTIONS BASED ON THE UPDATED     │
│ GRID STATUS INFORMATION TO ONE OR MORE NODES IN THE     │
│ COMMUNICATIONS GRID                                     │
│                        512                              │
└─────────────────────────────────────────────────────────┘
```

FIG. 5

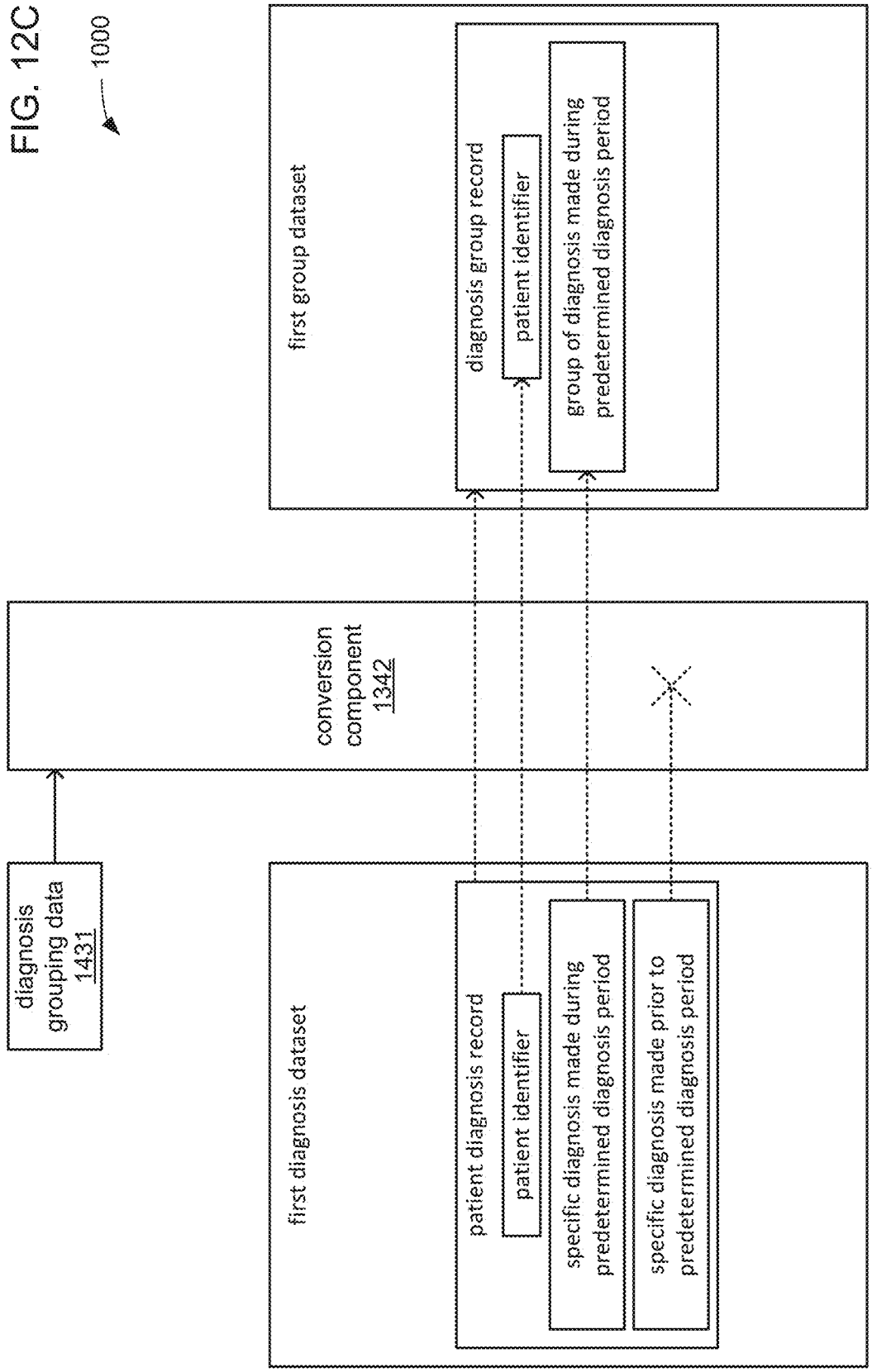

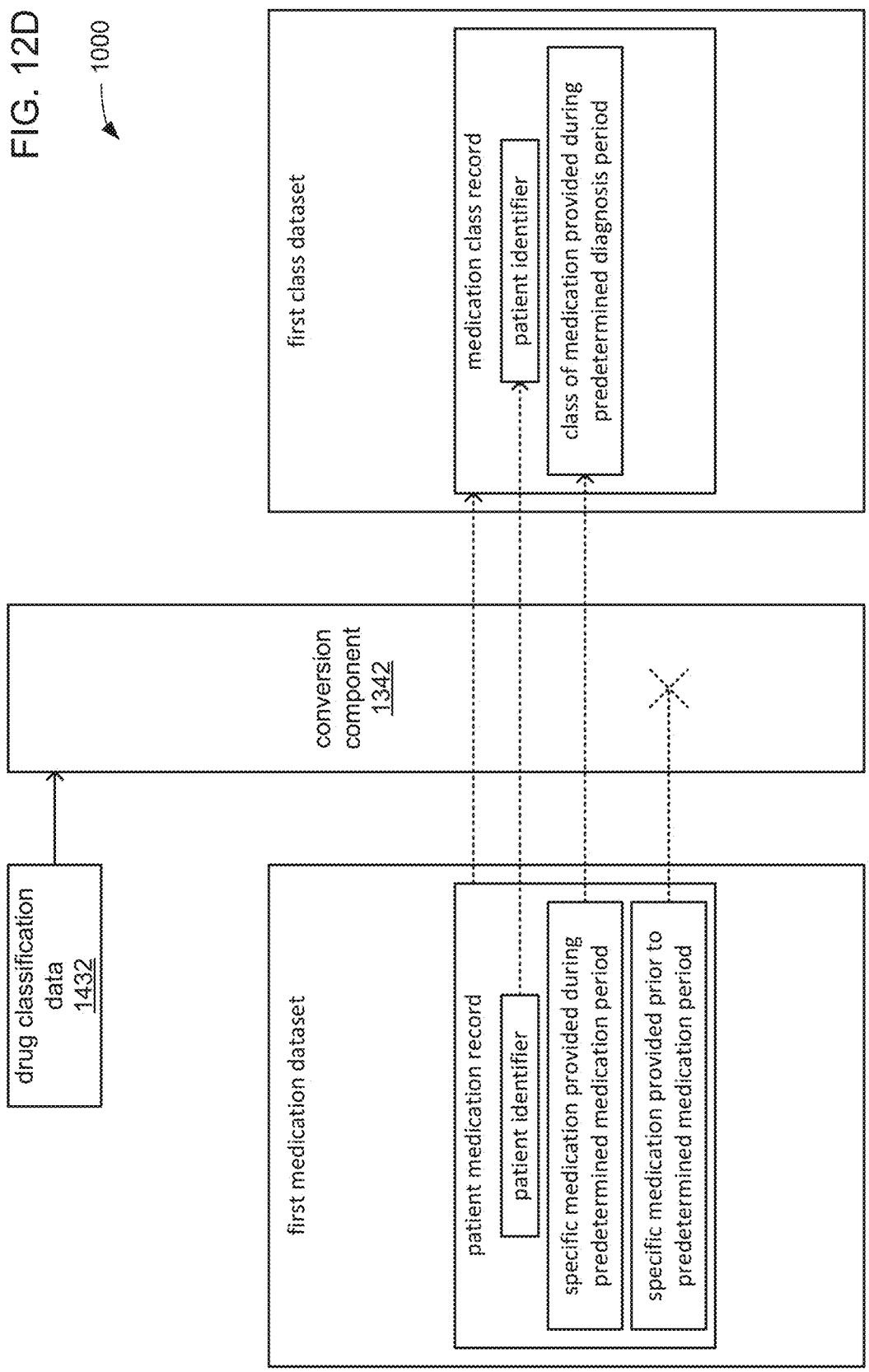

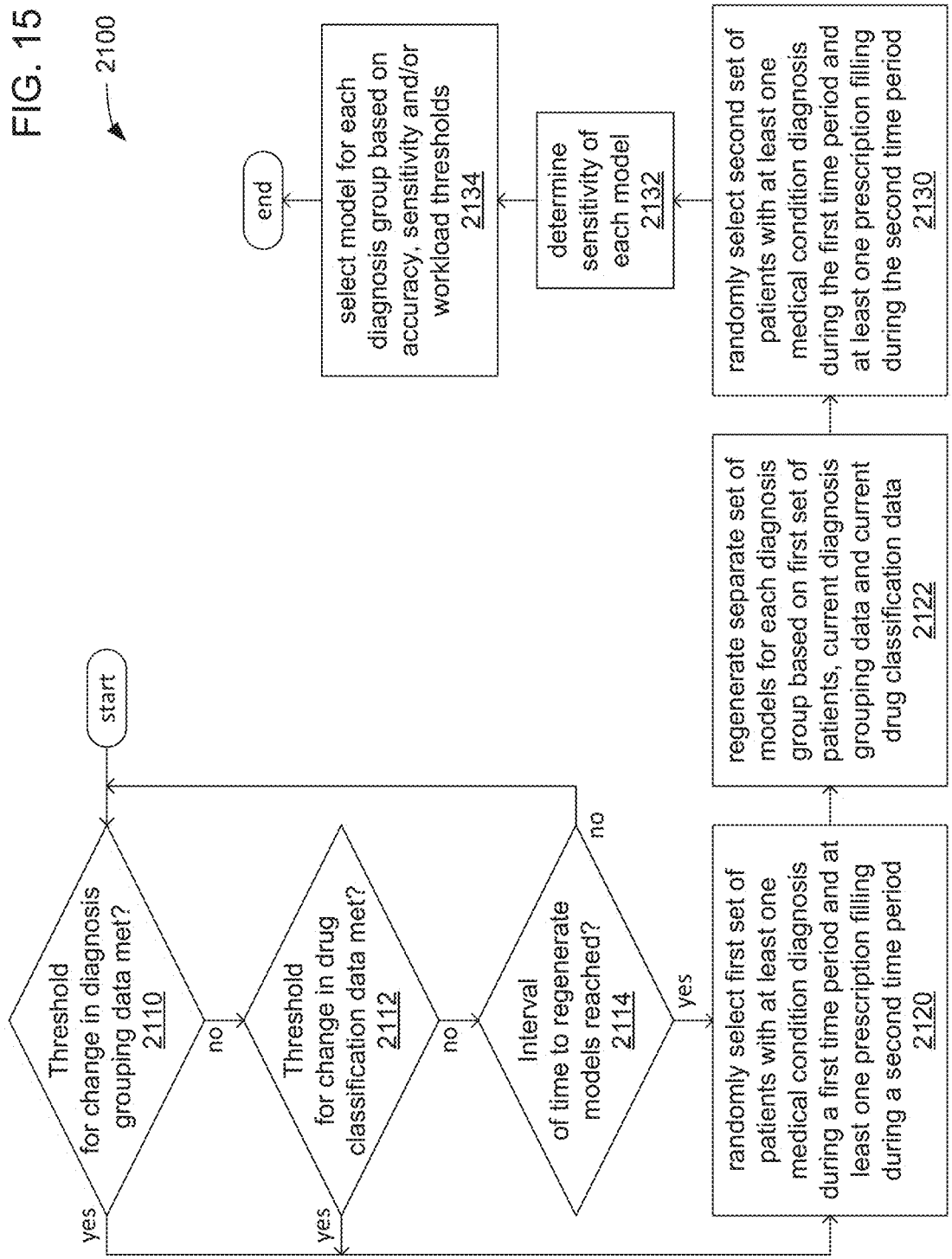

DISTRIBUTED CORRELATION AND ANALYSIS OF PATIENT THERAPY DATA

CROSS-REFERENCE TO RELATED APPLICATIONS

This application claims the benefit of priority under 35 U.S.C. § 119(e) to U.S. Provisional Application Ser. No. 62/156,806 filed May 4, 2015, the entirety of which is incorporated herein by reference.

BACKGROUND

Almost all medications can have undesirable side effects on the biochemistry and/or physiology of a patient, and there are combinations of medications that can interact within a patient's body in a way that can be toxic. It is for this reason that many medications require the issuance of a prescription by a licensed doctor to allow a pharmacy to provide them to a patient. However, lack of coordination in the storage and use of patient data among medical professionals involved in various stages of the provision of medications to patients can result in prescriptions for medications being issued without proper diagnoses and/or excessive quantities of medications being provided to patients. The results can be quite serious as overuse of a single medication and/or creations of combinations of medications that can have potentially deadly consequences.

SUMMARY

This summary is not intended to identify only key or essential features of the described subject matter, nor is it intended to be used in isolation to determine the scope of the described subject matter. The subject matter should be understood by reference to appropriate portions of the entire specification of this patent, any or all drawings, and each claim.

An apparatus may include a processor component and a storage to store instructions that, when executed by the processor component, cause the processor component to retrieve patient diagnosis records of a first set of patients and a second set of patients from a diagnosis database, and to retrieve patient medication records of the first set and the second set from a medication database. For each patient diagnosis record associated with a patient of the first set or the second set that includes at least one indication of a diagnosis made within a first time period, the processor component may be caused to perform operations including generate a corresponding diagnosis group record; correlate each diagnosis indicated in the patient diagnosis record as made within the first time period to a diagnosis group; and for each diagnosis group correlated to at least one diagnosis indicated as made within the first time period, generate in the corresponding diagnosis group record an indication of at least one diagnosis in the diagnosis group made within the first time period. For each patient medication record associated with a patient of the first set or the second set that includes at least one indication of at least one medication provided to the patient within a second time period, the processor component may be caused to perform operations perform operations including generate a corresponding medication class record; correlate each medication indicated in the patient medication record as provided to the patient within the second time period to a medication class; and for each medication class correlated to at least one medication indicated as provided to the patient within the second time period, generate in the corresponding medication class record an indication of at least one medication in the medication class provided to the patient within the second time period. For each patient of the first set of patients for which a corresponding diagnosis group record is generated and for which a corresponding medication class record is generated, the processor component may be caused to identify at least one correlation between at least one diagnosis group and at least one medication class. For each diagnosis group for which at least one correlation is identified, the processor component may be caused to derive a set of models that correlate the diagnosis group to at least one medication class based on the at least one identified correlation. For each patient of the second set of patients for which a corresponding diagnosis group record is generated and for which a corresponding medication class record is generated, the processor component may be caused to perform operations including employ each model of each set of models to make at least one prediction of at least one diagnosis group as indicated in the corresponding diagnosis group record based on at least one medication class indicated in the corresponding medication class record; and compare the at least one prediction to the corresponding diagnosis group record to derive a tally of at least one of true positives or false positives for each prediction.

The processor component may be caused to, for each diagnosis group for which a set of models is generated, perform operations including calculate at least one of a measure of sensitivity or a measure of accuracy for each model of the set of models based on the tally of at least one of the true positives and the false positives; and select one model of the set of models based at least on the measure of sensitivity or the measure of accuracy. The measure of accuracy may be evaluated based on at least one of a Kolmogorov-Smirnov test, a misclassification rate or an average-square error. The processor component may be caused to, for each diagnosis group for which a set of models is generated, perform operations including determine whether at least one model of the set of models meets a threshold of at least one of sensitivity or accuracy; and condition the selection of the one model on a determination that at least one model of the set of models meets the threshold.

The processor component may be caused to retrieve patient diagnosis records of a third set of patients from the diagnosis database, and to retrieve patient medication records of the third set from the medication database. For each patient diagnosis record associated with a patient of the third set that includes at least one indication of a diagnosis made within a first time period, the processor component may be caused to perform operations including generate a corresponding diagnosis group record; correlate each diagnosis indicated in the patient diagnosis record as made within the first time period to a diagnosis group; and for each diagnosis group correlated to at least one diagnosis indicated as made within the first time period, generate in the corresponding diagnosis group record an indication of at least one diagnosis in the diagnosis group made within the first time period. For each patient medication record associated with a patient of the third set that includes at least one indication of at least one medication provided to the patient within a second time period, the processor component may be caused to perform operations including generate a corresponding medication class record; correlate each medication indicated in the patient medication record as provided to the patient within the second time period to a medication class; and for each medication class correlated to at least one medication indicated as provided to the patient within the second time period, generate in the corresponding medication class record an indication of at least one medication in the medication class provided to the patient within the second time period. For each patient of the third set of patients for which a corresponding diagnosis group record is generated and for which a corresponding medication class record is generated, the processor component may perform operations including employ each selected model of each set of models for which a model is selected to make at least one determination of at least one diagnosis group that should be indicated in the corresponding diagnosis group record based on at least one medication class indicated in the corresponding medication class record; and compare the at least one determination to the corresponding diagnosis group record to derive a tally of at least one of matches or mismatches for at least one of each patient of the third set or each pharmacy that provides at least one medication to a patient of the third set.

The processor component may be caused to present an indication of a patient identified by a selected model as having been provided at least one medication of a medication class within the second time period, but not having a diagnosis in a diagnosis group made within the first time period that the model determined should have been made. The processor component may be caused to present an indication of a pharmacy as having provided medications to a plurality of patients of the third set, wherein each patient of the plurality of patients is identified by a selected model as having been provided at least one medication of a medication class within the second time period, but not having a diagnosis in a diagnosis group made within the first time period that the model determined should have been made; and the plurality of patients exceeds in number a predetermined threshold of patients so identified.

A computer-program product tangibly embodied in a non-transitory machine-readable storage medium may include instructions operable to cause a processor component to retrieve patient diagnosis records of a first set of patients and a second set of patients from a diagnosis database, and to retrieve patient medication records of the first set and the second set from a medication database. For each patient diagnosis record associated with a patient of the first set or the second set that includes at least one indication of a diagnosis made within a first time period, the processor component may be caused to perform operations including generate a corresponding diagnosis group record; correlate each diagnosis indicated in the patient diagnosis record as made within the first time period to a diagnosis group; and for each diagnosis group correlated to at least one diagnosis indicated as made within the first time period, generate in the corresponding diagnosis group record an indication of at least one diagnosis in the diagnosis group made within the first time period. For each patient medication record associated with a patient of the first set or the second set that includes at least one indication of at least one medication provided to the patient within a second time period, the processor component may be caused to perform operations including generate a corresponding medication class record; correlate each medication indicated in the patient medication record as provided to the patient within the second time period to a medication class; and for each medication class correlated to at least one medication indicated as provided to the patient within the second time period, generate in the corresponding medication class record an indication of at least one medication in the medication class provided to the patient within the second time period. For each patient of the first set of patients for which a corresponding diagnosis group record is generated and for which a corresponding medication class record is generated, the processor component may be caused to identify at least one correlation between at least one diagnosis group and at least one medication class. For each diagnosis group for which at least one correlation is identified, the processor component may be caused to derive a set of models that correlate the diagnosis group to at least one medication class based on the at least one identified correlation. For each patient of the second set of patients for which a corresponding diagnosis group record is generated and for which a corresponding medication class record is generated, the processor component may be caused to perform operations including employ each model of each set of models to make at least one prediction of at least one diagnosis group as indicated in the corresponding diagnosis group record based on at least one medication class indicated in the corresponding medication class record; and compare the at least one prediction to the corresponding diagnosis group record to derive a tally of at least one of true positives or false positives for each prediction.

The processor component may be caused to, for each diagnosis group for which a set of models is generated, perform operations including calculate at least one of a measure of sensitivity or a measure of accuracy for each model of the set of models based on the tally of at least one of the true positives and the false positives; and select one model of the set of models based at least on the measure of sensitivity or the measure of accuracy. The measure of accuracy may be evaluated based on at least one of a Kolmogorov-Smirnov test, a misclassification rate or an average-square error. The processor component may be caused to, for each diagnosis group for which a set of models is generated, perform operations including determine whether at least one model of the set of models meets a threshold of at least one of sensitivity or accuracy; and condition the selection of the one model on a determination that at least one model of the set of models meets the threshold.

The processor component may be caused to retrieve patient diagnosis records of a third set of patients from the diagnosis database, and to retrieve patient medication records of the third set from the medication database. For each patient diagnosis record associated with a patient of the third set that includes at least one indication of a diagnosis made within a first time period, the processor component may be caused to perform operations including generate a corresponding diagnosis group record; correlate each diagnosis indicated in the patient diagnosis record as made within the first time period to a diagnosis group; and for each diagnosis group correlated to at least one diagnosis indicated as made within the first time period, generate in the corresponding diagnosis group record an indication of at least one diagnosis in the diagnosis group made within the first time period. For each patient medication record associated with a patient of the third set that includes at least one indication of at least one medication provided to the patient within a second time period, the processor may be caused to perform operations including generate a corresponding medication class record; correlate each medication indicated in the patient medication record as provided to the patient within the second time period to a medication class; and for each medication class correlated to at least one medication indicated as provided to the patient within the second time period, generate in the corresponding medication class record an indication of at least one medication in the medication class provided to the patient within the second time period. For each patient of the third set of patients for which a corresponding diagnosis group record is generated and for which a corresponding medication class record is generated, the processor may be caused to perform operations including employ each selected model of each set of models for which a model is selected to make at least one determination of at least one diagnosis group that should be indicated in the corresponding diagnosis group record based on at least one medication class indicated in the corresponding medication class record; and compare the at least one determination to the corresponding diagnosis group record to derive a tally of at least one of matches or mismatches for at least one of each patient of the third set or each pharmacy that provides at least one medication to a patient of the third set.

The processor component may be caused to present an indication of a patient identified by a selected model as having been provided at least one medication of a medication class within the second time period, but not having a diagnosis in a diagnosis group made within the first time period that the model determined should have been made. The processor component may be caused to present an indication of a pharmacy as having provided medications to a plurality of patients of the third set, wherein each patient of the plurality of patients is identified by a selected model as having been provided at least one medication of a medication class within the second time period, but not having a diagnosis in a diagnosis group made within the first time period that the model determined should have been made; and the plurality of patients exceeds in number a predetermined threshold of patients so identified.

A computer-implemented method may include retrieving patient diagnosis records of a first set of patients and a second set of patients from a diagnosis database, and retrieving patient medication records of the first set and the second set from a medication database. For each patient diagnosis record associated with a patient of the first set or the second set that includes at least one indication of a diagnosis made within a first time period, the method may include performing operations including generating a corresponding diagnosis group record; correlating each diagnosis indicated in the patient diagnosis record as made within the first time period to a diagnosis group; and for each diagnosis group correlated to at least one diagnosis indicated as made within the first time period, generating in the corresponding diagnosis group record an indication of at least one diagnosis in the diagnosis group made within the first time period. For each patient medication record associated with a patient of the first set or the second set that includes at least one indication of at least one medication provided to the patient within a second time period, the method may include performing operations including generating a corresponding medication class record; correlating each medication indicated in the patient medication record as provided to the patient within the second time period to a medication class; and for each medication class correlated to at least one medication indicated as provided to the patient within the second time period, generating in the corresponding medication class record an indication of at least one medication in the medication class provided to the patient within the second time period. For each patient of the first set of patients for which a corresponding diagnosis group record is generated and for which a corresponding medication class record is generated, the method may include identifying at least one correlation between at least one diagnosis group and at least one medication class. For each diagnosis group for which at least one correlation is identified, the method may include deriving a set of models that correlate the diagnosis group to at least one medication class based on the at least one identified correlation. For each patient of the second set of patients for which a corresponding diagnosis group record is generated and for which a corresponding medication class record is generated, the method may include performing operations including employing each model of each set of models to make at least one prediction of at least one diagnosis group as indicated in the corresponding diagnosis group record based on at least one medication class indicated in the corresponding medication class record, and comparing the at least one prediction to the corresponding diagnosis group record to derive a tally of at least one of true positives or false positives for each prediction.

The method may include, for each diagnosis group for which a set of models is generated, performing operations including calculating at least one of a measure of sensitivity or a measure of accuracy for each model of the set of models based on the tally of at least one of the true positives and the false positives; and selecting one model of the set of models based at least on the measure of sensitivity or the measure of accuracy. The measure of accuracy is evaluated based on at least one of a Kolmogorov-Smirnov test, a misclassification rate or an average-square error. The method may include, for each diagnosis group for which a set of models is generated, performing operations including determining whether at least one model of the set of models meets a threshold of at least one of sensitivity or accuracy; and conditioning the selection of the one model on a determination that at least one model of the set of models meets the threshold.

The method may include retrieving patient diagnosis records of a third set of patients from the diagnosis database, and retrieving patient medication records of the third set from the medication database. For each patient diagnosis record associated with a patient of the third set that includes at least one indication of a diagnosis made within a first time period, the method may include performing operations including generating a corresponding diagnosis group record; correlating each diagnosis indicated in the patient diagnosis record as made within the first time period to a diagnosis group; and for each diagnosis group correlated to at least one diagnosis indicated as made within the first time period, generating in the corresponding diagnosis group record an indication of at least one diagnosis in the diagnosis group made within the first time period. For each patient medication record associated with a patient of the third set that includes at least one indication of at least one medication provided to the patient within a second time period, the method may include performing operations including generating a corresponding medication class record; correlating each medication indicated in the patient medication record as provided to the patient within the second time period to a medication class; and for each medication class correlated to at least one medication indicated as provided to the patient within the second time period, generating in the corresponding medication class record an indication of at least one medication in the medication class provided to the patient within the second time period. For each patient of the third set of patients for which a corresponding diagnosis group record is generated and for which a corresponding medication class record is generated, the method may include performing operations including employing each selected model of each set of models for which a model is selected to make at least one determination of at least one diagnosis group that should be indicated in the corresponding diagnosis group record based on at least one medication class indicated in the corresponding medication class record; and comparing the at least one determination to the corresponding diagnosis group record to derive a tally of at least one of matches or mismatches for at least one of each patient of the third set or each pharmacy that provides at least one medication to a patient of the third set.

The method may include presenting an indication of a patient identified by a selected model as having been provided at least one medication of a medication class within the second time period, but not having a diagnosis in a diagnosis group made within the first time period that the model determined should have been made. The method may include presenting an indication of a pharmacy as having provided medications to a plurality of patients of the third set, wherein each patient of the plurality of patients is identified by a selected model as having been provided at least one medication of a medication class within the second time period, but not having a diagnosis in a diagnosis group made within the first time period that the model determined should have been made; and the plurality of patients exceeds in number a predetermined threshold of patients so identified.

Each model of each set of models may include at least one of a decision tree, a regression, or a neural network. The diagnosis database may include a table wherein each patient diagnosis record comprises a row, each row of the diagnosis database may include at least one Boolean flag indicating whether a diagnosis is made, generation of a diagnosis group record may include an addition of a row that corresponds to a row of the diagnosis database to a table of a group dataset, and each row of the group dataset may include at least one Boolean flag indicating a whether a diagnosis in a diagnosis group was made within the first time period. The medication database may include a table wherein each patient medication record comprises a row, each row of the medication database may include at least one count of instances in which a medication is provided to a patient, generation of a patient class record may include an addition of a row that corresponds to a row of the medication database to a table of a class dataset, and each row of the class dataset may include at least one count of instances in which a medication of a medication class was provided to the patient within the second time period. The first time period may include 24 months and the second time period may include 12 months.

The foregoing, together with other features and embodiments, will become more apparent upon referring to the following specification, claims, and accompanying drawings.

BRIEF DESCRIPTION OF THE DRAWINGS

The present disclosure is described in conjunction with the appended figures:

FIG. 5 illustrates a flow chart showing an example process for adjusting a communications grid or a work project in a communications grid after a failure of a node, according to some embodiments of the present technology.

FIGS. 12A, 12B, 12C, 12D and 12E, together, illustrate an example of generating sets of models.

FIG. 15 illustrates an example embodiment of a logic flow of controlling generation, testing, selection and use of models.

DETAILED DESCRIPTION

Figure 1:
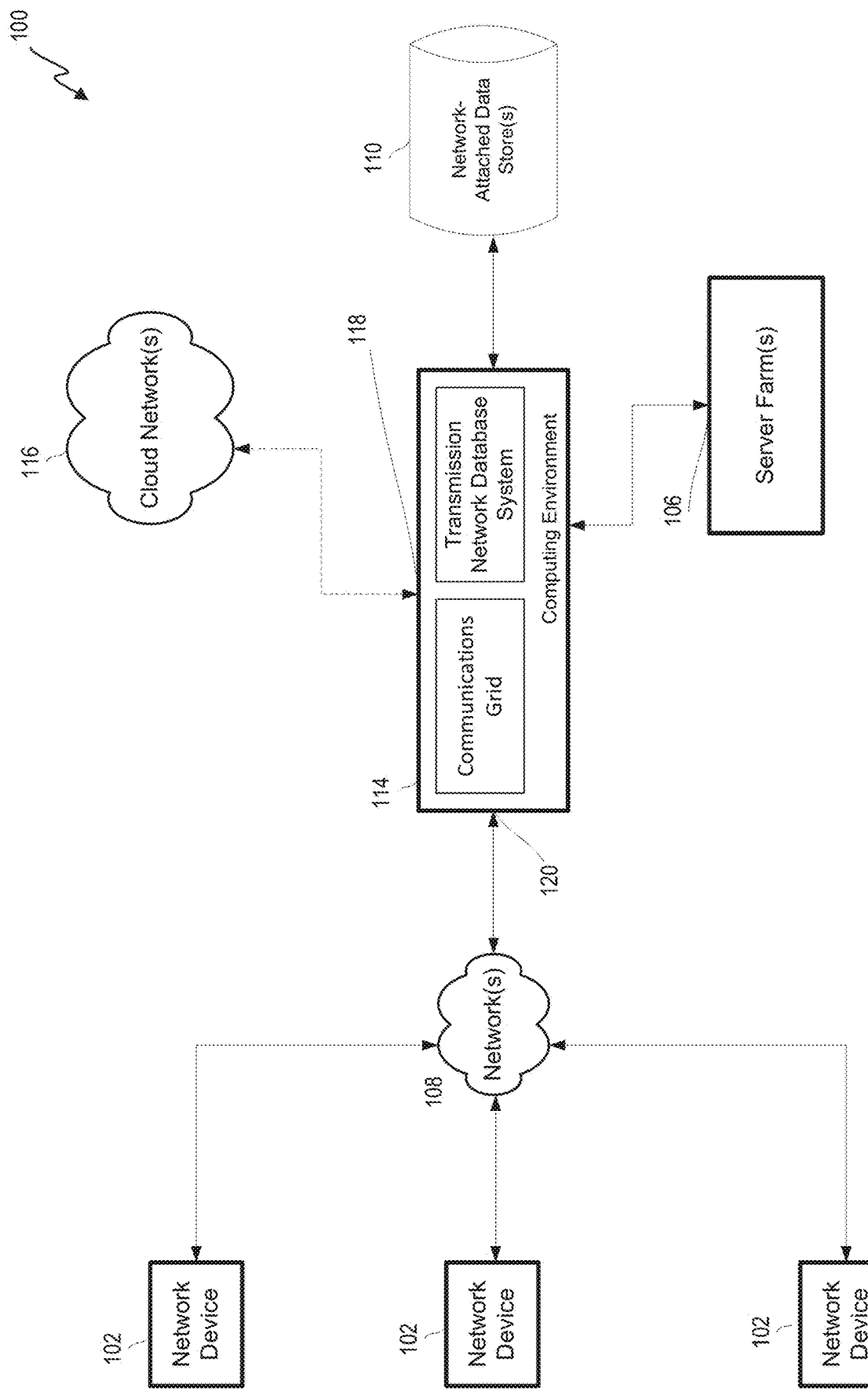
FIG. 1 illustrates a block diagram that provides an illustration of the hardware components of a computing system, according to some embodiments of the present technology.

Various embodiments described herein are generally directed to the detection of suspicious patterns in filling prescription medications by correlating medication histories with diagnosis histories. Separate sets of models for each group of diagnoses may be derived from correlations found between recent histories of diagnosis groups and recent histories of medication classes for a first set of patients. Once derived, the ability of the models to accurately predict diagnosis groups for recent diagnoses based on medication classes for recently filled medication prescriptions is evaluated using recent histories of diagnosis groups and recent histories of medication classes for a second set of patients. For each diagnosis group, a model is selected from the set of models associated with that group based on accuracy of predictions, sensitivity to suspicious patterns and/or capacity of investigators to investigate pharmacies and/or patients associated with suspicious prescription filling patterns.

For a first set of patients, a first diagnosis dataset of patient diagnosis records may be retrieved from a diagnosis database and a corresponding first medication dataset of patient medication records may be retrieved from a medication database. The first set of patients may be randomly selected for reasons of sample quality. Also, the first set of patients may also be limited to patients who have received at least one diagnosis of a medical condition within a predetermined diagnosis period, and who have had at least one prescription filled within a predetermined medication period to ensure that each patient presents at least one correlation between at least one diagnosis and at least one instance of receiving medication. As it may be expected that a prescription arises from a diagnosis, the predetermined diagnosis period may reach further back in time than the predetermined medication period (e.g., a predetermined diagnosis period of two years into the past versus a predetermined medication period of one year into the past).

A first group dataset may be generated from the first diagnosis dataset based on diagnosis grouping data that categorizes diagnoses into diagnosis groups that may each be correlated to a different system of the human body (e.g., cardiovascular system, endocrine system, etc.). In so doing, for each patient diagnosis record within the first diagnosis dataset, a corresponding diagnosis group record may be generated within the first group dataset. For each diagnosis indicated in the patient diagnosis record a corresponding indication of a diagnosis group may be included in the corresponding diagnosis group record.

Correspondingly, a first class dataset may be generated from the first medication dataset based on drug classification data that categorizes medications into medication classes that may each be correlated to physiological effects brought about by each medication and/or mechanism within the human by which each medication does so. In so doing, for each patient medication record within the first medication dataset, a corresponding medication class record may be generated within the first class dataset. For each medication indicated in the each patient medication record a corresponding indication of a medication class may be included in the corresponding medication class record.

Following the generation of the first group dataset and the first class dataset, models that correlate medication classes to diagnosis groups may be generated from the correspondences of diagnosis groups and medication classes found in the corresponding records of the first group dataset and the first class dataset. More specifically, a separate set of multiple models may be generated for each diagnosis group based on correspondences found between the diagnosis group and various medication classes. Different ones of the models in each set associated with a diagnosis group may be based on different modeling techniques.

Following generation of the sets of models, a second set of patients may be randomly selected for use in evaluating each of the multiple models in each of the sets of models. Again, in addition to being randomly selected, the second set of patients may also be limited to patients who have received at least one diagnosis of a medical condition within the predetermined diagnosis period, and who have had at least one prescription filled within the predetermined medication period. For the second set of patients, a second diagnosis dataset of patient diagnosis records may be retrieved from the diagnosis database and a corresponding second medication dataset of patient medication records may be retrieved from the medication database.

A second group dataset may be generated from the second diagnosis dataset based on the diagnosis grouping data. In so doing, for each patient diagnosis record within the second diagnosis dataset, a corresponding diagnosis group record may be generated within the second group dataset. Again, for each diagnosis indicated in the patient diagnosis record a corresponding indication of a diagnosis group may be included in the corresponding diagnosis group record. Correspondingly, a second class dataset may be generated from the second medication dataset based on the drug classification data. In so doing, for each patient medication record within the second medication dataset, a corresponding medication class record may be generated within the second class dataset. Again, for each medication indicated in the each patient medication record a corresponding indication of a medication class may be included in the corresponding medication class record.

Following the generation of the second group dataset and the second class dataset, the medication class records of the second class dataset may be used as inputs to each model in each set of models to derive predictions from the models of what diagnosis group or groups will be found to correspond to each indication in each medication class record of the filling of a prescription within a particular medication class. The predictions made by each model of each set of models may then be compared to diagnosis groups actually indicated in corresponding diagnosis group records of the second group dataset. The results of these comparisons may then be analyzed to determine degrees of accuracy and/or sensitivity for each model in each set of models. Thresholds of accuracy and/or sensitivity may then be applied to select a model from each set of models to be used in detecting suspicious patterns. Alternatively or additionally, the level of resources available to conduct investigations based on detected suspicious patterns may be taken into account. By way of example, a model among a set of models that detects too many or an insufficient number of suspicious patterns in filling prescriptions may not be selected in favor of selecting another model in that set that detects a number of suspicious patterns that more closely fits a current level of ability to conduct investigations. However, in some embodiments, it may be that none of the models within one or more of the sets of models meets the thresholds of accuracy and/or sensitivity such that none of the models within that set are selected.

Following the selection of one model from each set of models for which a selection is made, the selected models may be used with more of the records of the diagnosis database and corresponding records of the medication database to detect suspicious patterns in the filling of prescriptions. More specifically, patterns of claims filed by pharmacies for filling prescriptions that appear to be for fictitious prescriptions, for instances of filling proper prescriptions too frequently, etc. may be detected.

It is envisioned that as newer medications replace older ones and/or as changes occur in the manner in which medications are used over time, there will continue to be changes in correlations between diagnoses and the provision of medications to patients. Such changing usage of medications may include instances of so-called "off-label" usage of medications where a doctor determines that using a medication to address an ailment for which the medication may not have been originally created may help a patient for whom more conventional therapies have not been helpful. Thus, in some embodiments, such generation, testing and selection of models may be triggered to repeat at the end of a recurring interval of time (e.g., weekly or monthly) to keep the models that are used in detecting suspicious patterns up to date.

It should also be noted that, although the use of correlations between the provision of medications and diagnoses is described herein due to the typically strong nature of those correlations, correlations between the provision of medications and other aspects of patient histories may alternatively or additionally be used. For example, correlations between the provision of medications and one or more of genetic markers, past prescription history, past medication therapy outcomes, citizenship, economic status, marital status, age, occupational history, etc. Alternatively or additionally, correlations between the provision of medications and aspects of the medical histories of family members may be used, such diagnoses of family members, medications provided to family members, lifespans of family members, past medication therapy outcomes of family members, etc.

With general reference to notations and nomenclature used herein, portions of the detailed description that follows may be presented in terms of program procedures executed by a processor component of a machine or of multiple networked machines. These procedural descriptions and representations are used by those skilled in the art to most effectively convey the substance of their work to others skilled in the art. A procedure is here, and generally, conceived to be a self-consistent sequence of operations leading to a desired result. These operations are those requiring physical manipulations of physical quantities. Usually, though not necessarily, these quantities take the form of electrical, magnetic or optical communications capable of being stored, transferred, combined, compared, and otherwise manipulated. It proves convenient at times, principally for reasons of common usage, to refer to what is communicated as bits, values, elements, symbols, characters, terms, numbers, or the like. It should be noted, however, that all of these and similar terms are to be associated with the appropriate physical quantities and are merely convenient labels applied to those quantities.

Further, these manipulations are often referred to in terms, such as adding or comparing, which are commonly associated with mental operations performed by a human operator. However, no such capability of a human operator is necessary, or desirable in most cases, in any of the operations described herein that form part of one or more embodiments. Rather, these operations are machine operations. Useful machines for performing operations of various embodiments include machines selectively activated or configured by a routine stored within that is written in accordance with the teachings herein, and/or include apparatus specially constructed for the required purpose. Various embodiments also relate to apparatus or systems for performing these operations. These apparatus may be specially constructed for the required purpose or may include a general purpose computer. The required structure for a variety of these machines will appear from the description given.

Reference is now made to the drawings, wherein like reference numerals are used to refer to like elements throughout. In the following description, for purposes of explanation, numerous specific details are set forth in order to provide a thorough understanding thereof. It may be evident, however, that the novel embodiments can be practiced without these specific details. In other instances, well known structures and devices are shown in block diagram form in order to facilitate a description thereof. The intention is to cover all modifications, equivalents, and alternatives within the scope of the claims.

Systems depicted in some of the figures may be provided in various configurations. In some embodiments, the systems may be configured as a distributed system where one or more components of the system are distributed across one or more networks in a cloud computing system.

FIG. 1 is a block diagram that provides an illustration of the hardware components of a data transmission network 100, according to embodiments of the present technology.

Data transmission network 100 is a specialized computer system that may be used for processing large amounts of data where a large number of computer processing cycles are required.

Data transmission network 100 may also include computing environment 114. Computing environment 114 may be a specialized computer or other machine that processes the data received within the data transmission network 100. Data transmission network 100 also includes one or more network devices 102. Network devices 102 may include client devices that attempt to communicate with computing environment 114. For example, network devices 102 may send data to the computing environment 114 to be processed, may send signals to the computing environment 114 to control different aspects of the computing environment or the data it is processing, among other reasons. Network devices 102 may interact with the computing environment 114 through a number of ways, such as, for example, over one or more networks 108. As shown in FIG. 1, computing environment 114 may include one or more other systems. For example, computing environment 114 may include a database system 118 and/or a communications grid 120.

Figure 8:
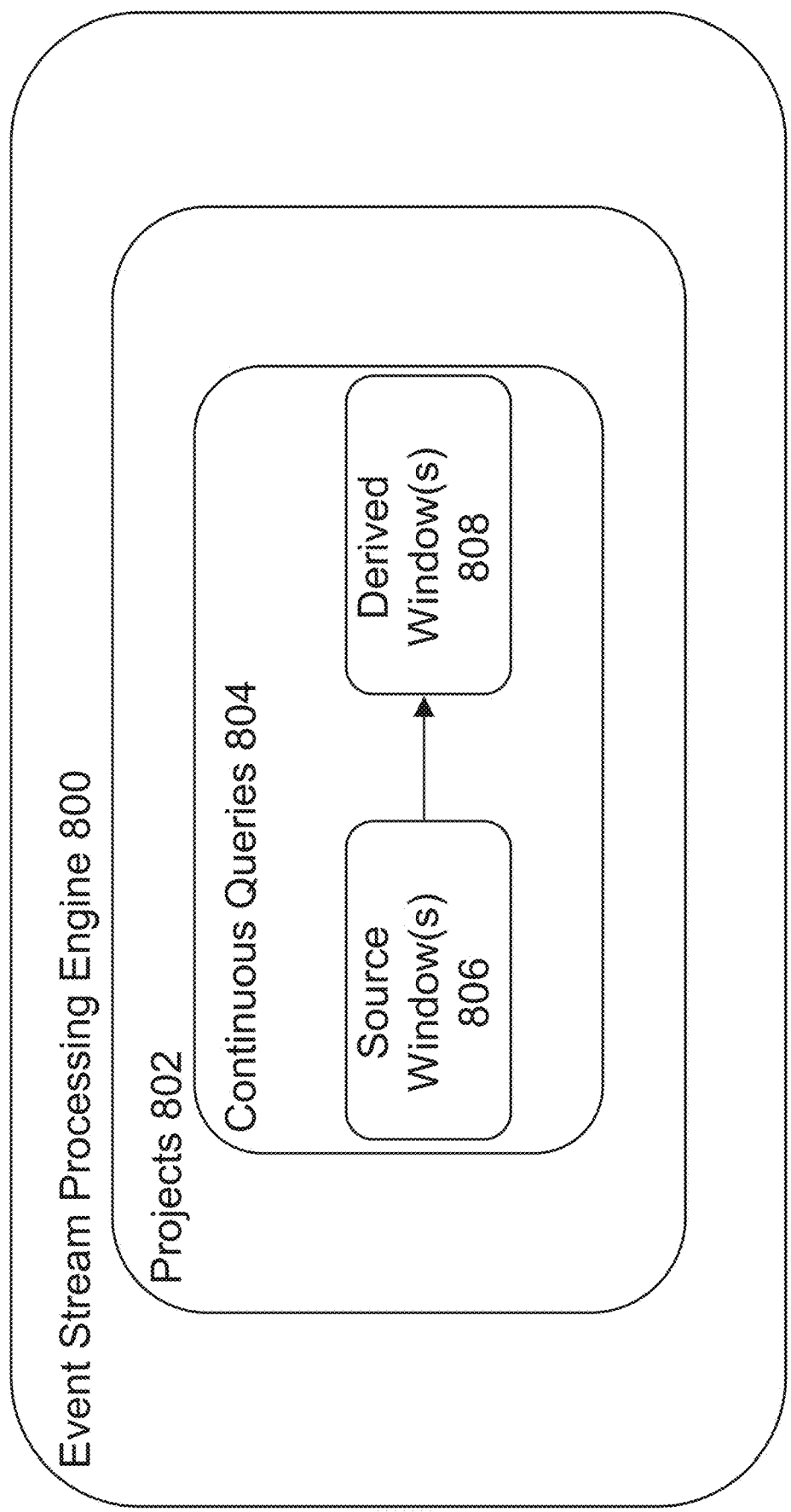
FIG. 8 illustrates a block diagram including components of an Event Stream Processing Engine (ESPE), according to embodiments of the present technology.
Figure 9:
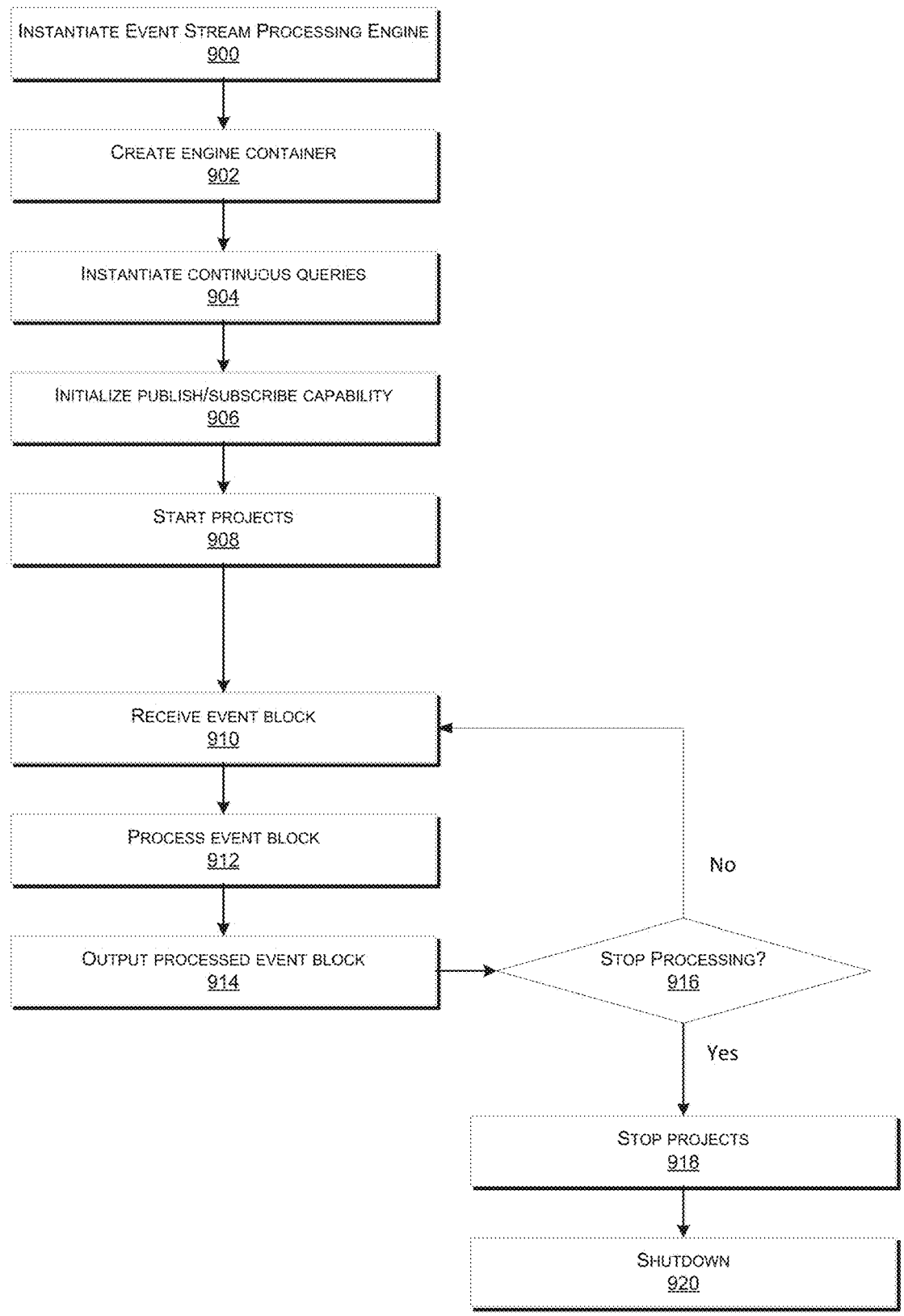
FIG. 9 illustrates a flow chart showing an example process including operations performed by an event stream processing engine, according to some embodiments of the present technology.
Figure 10:
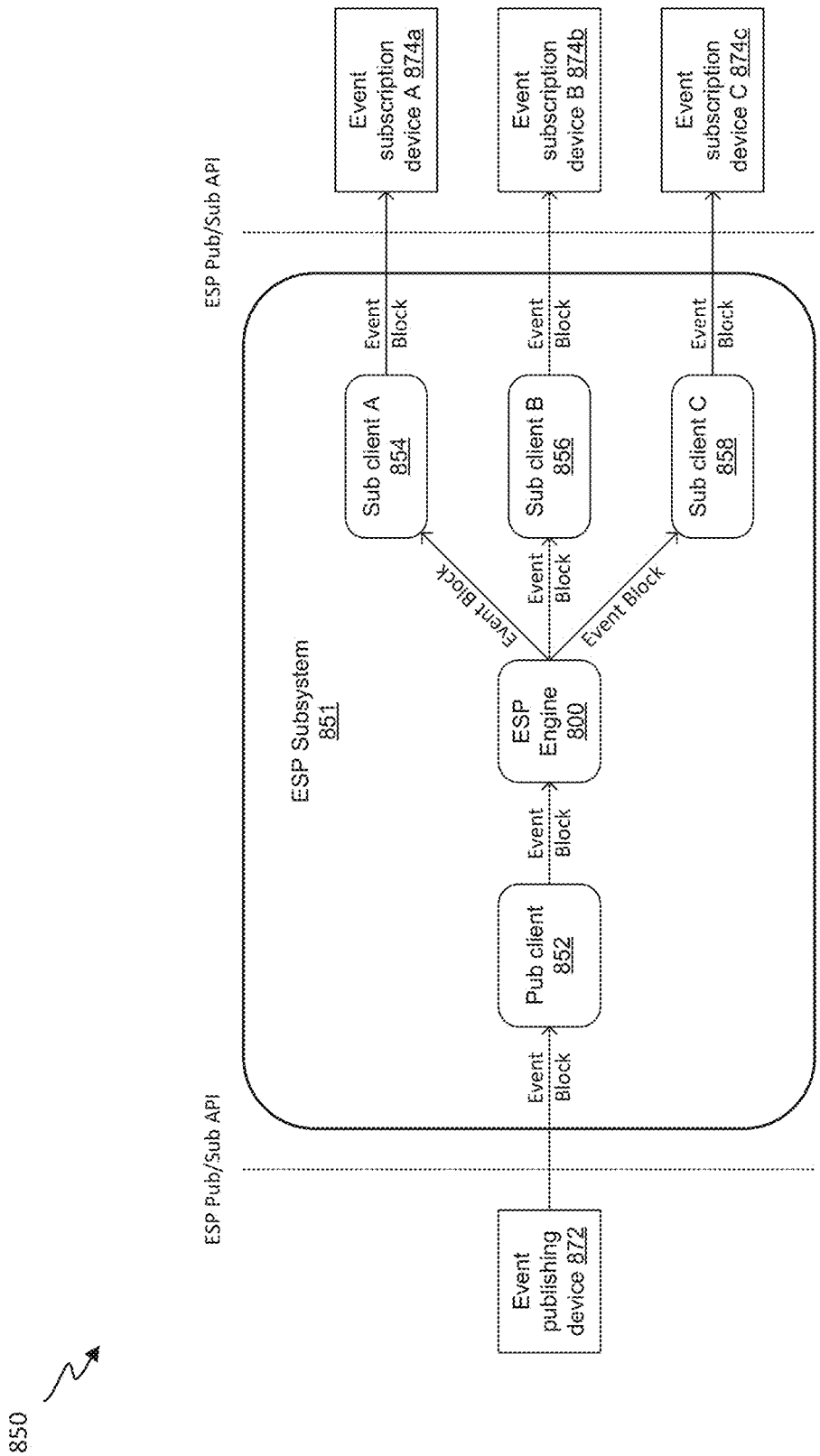
FIG. 10 illustrates an ESP system interfacing between a publishing device and multiple event subscribing devices, according to embodiments of the present technology.

In other embodiments, network devices may provide a large amount of data, either all at once or streaming over a period of time (e.g., using event stream processing (ESP), described further with respect to FIGS. 8-10), to the computing environment 114 via networks 108. For example, network devices 102 may include network computers, sensors, databases, or other devices that may transmit or otherwise provide data to computing environment 114. For example, network devices may include local area network devices, such as routers, hubs, switches, or other computer networking devices. These devices may provide a variety of stored or generated data, such as network data or data specific to the network devices themselves. Network devices may also include sensors that monitor their environment or other devices to collect data regarding that environment or those devices, and such network devices may provide data they collect over time. Network devices may also include devices within the internet of things, such as devices within a home automation network. Some of these devices may be referred to as edge devices, and may involve edge computing circuitry. Data may be transmitted by network devices directly to computing environment 114 or to network-attached data stores, such as network-attached data stores 110 for storage so that the data may be retrieved later by the computing environment 114 or other portions of data transmission network 100.

Data transmission network 100 may also include one or more network-attached data stores 110. Network-attached data stores 110 are used to store data to be processed by the computing environment 114 as well as any intermediate or final data generated by the computing system in non-volatile memory. However in certain embodiments, the configuration of the computing environment 114 allows its operations to be performed such that intermediate and final data results can be stored solely in volatile memory (e.g., RAM), without a requirement that intermediate or final data results be stored to non-volatile types of memory (e.g., disk). This can be useful in certain situations, such as when the computing environment 114 receives ad hoc queries from a user and when responses, which are generated by processing large amounts of data, need to be generated on-the-fly. In this non-limiting situation, the computing environment 114 may be configured to retain the processed information within memory so that responses can be generated for the user at different levels of detail as well as allow a user to interactively query against this information.

Network-attached data stores may store a variety of different types of data organized in a variety of different ways and from a variety of different sources. For example, network-attached data storage may include storage other than primary storage located within computing environment 114 that is directly accessible by processors located therein. Network-attached data storage may include secondary, tertiary or auxiliary storage, such as large hard drives, servers, virtual memory, among other types. Storage devices may include portable or non-portable storage devices, optical storage devices, and various other mediums capable of storing, containing data. A machine-readable storage medium or computer-readable storage medium may include a non-transitory medium in which data can be stored and that does not include carrier waves and/or transitory electronic signals. Examples of a non-transitory medium may include, for example, a magnetic disk or tape, optical storage media such as compact disk or digital versatile disk, flash memory, memory or memory devices. A computer-program product may include code and/or machine-executable instructions that may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, among others. Furthermore, the data stores may hold a variety of different types of data. For example, network-attached data stores 110 may hold unstructured (e.g., raw) data, such as manufacturing data (e.g., a database containing records identifying products being manufactured with parameter data for each product, such as colors and models) or product sales databases (e.g., a database containing individual data records identifying details of individual product sales).

The unstructured data may be presented to the computing environment 114 in different forms such as a flat file or a conglomerate of data records, and may have data values and accompanying time stamps. The computing environment 114 may be used to analyze the unstructured data in a variety of ways to determine the best way to structure (e.g., hierarchically) that data, such that the structured data is tailored to a type of further analysis that a user wishes to perform on the data. For example, after being processed, the unstructured time stamped data may be aggregated by time (e.g., into daily time period units) to generate time series data and/or structured hierarchically according to one or more dimensions (e.g., parameters, attributes, and/or variables). For example, data may be stored in a hierarchical data structure, such as a ROLAP OR MOLAP database, or may be stored in another tabular form, such as in a flat-hierarchy form.

Data transmission network 100 may also include one or more server farms 106. Computing environment 114 may route select communications or data to the one or more sever farms 106 or one or more servers within the server farms. Server farms 106 can be configured to provide information in a predetermined manner. For example, server farms 106 may access data to transmit in response to a communication. Server farms 106 may be separately housed from each other device within data transmission network 100, such as computing environment 114, and/or may be part of a device or system.

Server farms 106 may host a variety of different types of data processing as part of data transmission network 100. Server farms 106 may receive a variety of different data from network devices, from computing environment 114, from cloud network 116, or from other sources. The data may have been obtained or collected from one or more sensors, as inputs from a control database, or may have been received as inputs from an external system or device. Server farms 106 may assist in processing the data by turning raw data into processed data based on one or more rules implemented by the server farms. For example, sensor data may be analyzed to determine changes in an environment over time or in real-time.

Data transmission network 100 may also include one or more cloud networks 116. Cloud network 116 may include a cloud infrastructure system that provides cloud services. In certain embodiments, services provided by the cloud network 116 may include a host of services that are made available to users of the cloud infrastructure system on demand Cloud network 116 is shown in FIG. 1 as being connected to computing environment 114 (and therefore having computing environment 114 as its client or user), but cloud network 116 may be connected to or utilized by any of the devices in FIG. 1. Services provided by the cloud network can dynamically scale to meet the needs of its users. The cloud network 116 may comprise one or more computers, servers, and/or systems. In some embodiments, the computers, servers, and/or systems that make up the cloud network 116 are different from the user's own on-premises computers, servers, and/or systems. For example, the cloud network 116 may host an application, and a user may, via a communication network such as the Internet, on demand, order and use the application.

While each device, server and system in FIG. 1 is shown as a single device, it will be appreciated that multiple devices may instead be used. For example, a set of network devices can be used to transmit various communications from a single user, or remote server 140 may include a server stack. As another example, data may be processed as part of computing environment 114.

Each communication within data transmission network 100 (e.g., between client devices, between a device and connection management system 150, between servers 106 and computing environment 114 or between a server and a device) may occur over one or more networks 108. Networks 108 may include one or more of a variety of different types of networks, including a wireless network, a wired network, or a combination of a wired and wireless network. Examples of suitable networks include the Internet, a personal area network, a local area network (LAN), a wide area network (WAN), or a wireless local area network (WLAN). A wireless network may include a wireless interface or combination of wireless interfaces. As an example, a network in the one or more networks 108 may include a short-range communication channel, such as a Bluetooth or a Bluetooth Low Energy channel. A wired network may include a wired interface. The wired and/or wireless networks may be implemented using routers, access points, bridges, gateways, or the like, to connect devices in the network 114, as will be further described with respect to FIG. 2. The one or more networks 108 can be incorporated entirely within or can include an intranet, an extranet, or a combination thereof. In one embodiment, communications between two or more systems and/or devices can be achieved by a secure communications protocol, such as secure sockets layer (SSL) or transport layer security (TLS). In addition, data and/or transactional details may be encrypted.

Some aspects may utilize the Internet of Things (IoT), where things (e.g., machines, devices, phones, sensors) can be connected to networks and the data from these things can be collected and processed within the things and/or external to the things. For example, the IoT can include sensors in many different devices, and high value analytics can be applied to identify hidden relationships and drive increased efficiencies. This can apply to both big data analytics and real-time (e.g., ESP) analytics. This will be described further below with respect to FIG. 2.

As noted, computing environment 114 may include a communications grid 120 and a transmission network database system 118. Communications grid 120 may be a grid-based computing system for processing large amounts of data. The transmission network database system 118 may be for managing, storing, and retrieving large amounts of data that are distributed to and stored in the one or more network-attached data stores 110 or other data stores that reside at different locations within the transmission network database system 118. The compute nodes in the grid-based computing system 120 and the transmission network database system 118 may share the same processor hardware, such as processors that are located within computing environment 114.

Figure 2:
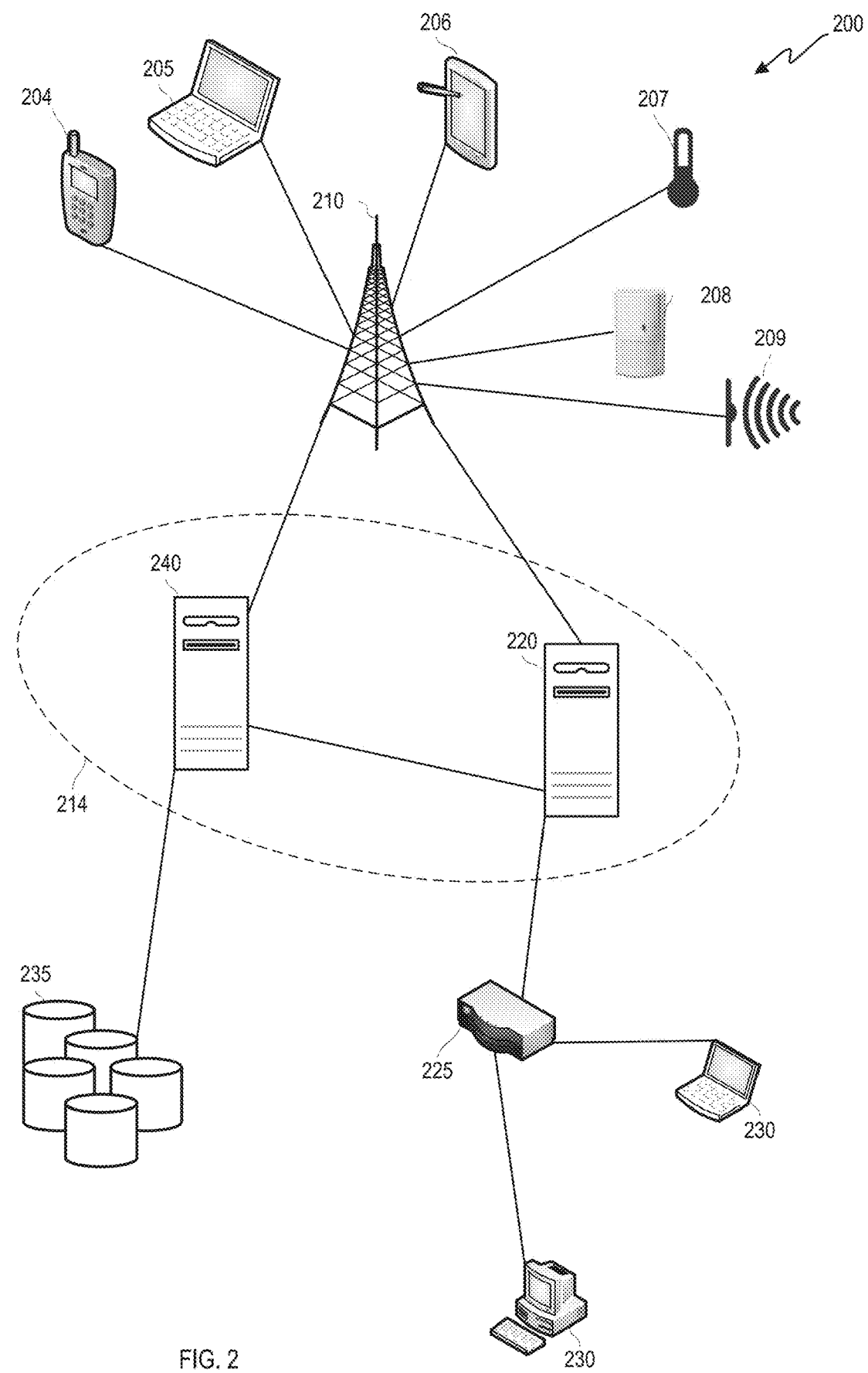
FIG. 2 illustrates an example network including an example set of devices communicating with each other over an exchange system and via a network, according to some embodiments of the present technology.

FIG. 2 illustrates an example network including an example set of devices communicating with each other over an exchange system and via a network, according to embodiments of the present technology. As noted, each communication within data transmission network 100 may occur over one or more networks. System 200 includes a network device 204 configured to communicate with a variety of types of client devices, for example client devices 230, over a variety of types of communication channels.

As shown in FIG. 2, network device 204 can transmit a communication over a network (e.g., a cellular network via a base station 210). The communication can be routed to another network device, such as network devices 205-209, via base station 210. The communication can also be routed to computing environment 214 via base station 210. For example, network device 204 may collect data either from its surrounding environment or from other network devices (such as network devices 205-209) and transmit that data to computing environment 214.

Although network devices 204-209 are shown in FIG. 2 as a mobile phone, laptop computer, tablet computer, temperature sensor, motion sensor, and audio sensor respectively, the network devices may be or include sensors that are sensitive to detecting aspects of their environment. For example, the network devices may include sensors such as water sensors, power sensors, electrical current sensors, chemical sensors, optical sensors, pressure sensors, geographic or position sensors (e.g., GPS), velocity sensors, acceleration sensors, flow rate sensors, among others. Examples of characteristics that may be sensed include force, torque, load, strain, position, temperature, air pressure, fluid flow, chemical properties, resistance, electromagnetic fields, radiation, irradiance, proximity, acoustics, moisture, distance, speed, vibrations, acceleration, electrical potential, electrical current, among others. The sensors may be mounted to various components used as part of a variety of different types of systems (e.g., an oil drilling operation). The network devices may detect and record data related to the environment that it monitors, and transmit that data to computing environment 214.

As noted, one type of system that may include various sensors that collect data to be processed and/or transmitted to a computing environment according to certain embodiments includes an oil drilling system. For example, the one or more drilling operation sensors may include surface sensors that measure a hook load, a fluid rate, a temperature and a density in and out of the wellbore, a standpipe pressure, a surface torque, a rotation speed of a drill pipe, a rate of penetration, a mechanical specific energy, etc. and downhole sensors that measure a rotation speed of a bit, fluid densities, downhole torque, downhole vibration (axial, tangential, lateral), a weight applied at a drill bit, an annular pressure, a differential pressure, an azimuth, an inclination, a dog leg severity, a measured depth, a vertical depth, a downhole temperature, etc. Besides the raw data collected directly by the sensors, other data may include parameters either developed by the sensors or assigned to the system by a client or other controlling device. For example, one or more drilling operation control parameters may control settings such as a mud motor speed to flow ratio, a bit diameter, a predicted formation top, seismic data, weather data, etc. Other data may be generated using physical models such as an earth model, a weather model, a seismic model, a bottom hole assembly model, a well plan model, an annular friction model, etc. In addition to sensor and control settings, predicted outputs, of for example, the rate of penetration, mechanical specific energy, hook load, flow in fluid rate, flow out fluid rate, pump pressure, surface torque, rotation speed of the drill pipe, annular pressure, annular friction pressure, annular temperature, equivalent circulating density, etc. may also be stored in the data warehouse.

In another example, another type of system that may include various sensors that collect data to be processed and/or transmitted to a computing environment according to certain embodiments includes a home automation or similar automated network in a different environment, such as an office space, school, public space, sports venue, or a variety of other locations. Network devices in such an automated network may include network devices that allow a user to access, control, and/or configure various home appliances located within the user's home (e.g., a television, radio, light, fan, humidifier, sensor, microwave, iron, and/or the like), or outside of the user's home (e.g., exterior motion sensors, exterior lighting, garage door openers, sprinkler systems, or the like). For example, network device 102 may include a home automation switch that may be coupled with a home appliance. In another embodiment, a network device can allow a user to access, control, and/or configure devices, such as office-related devices (e.g., copy machine, printer, or fax machine), audio and/or video related devices (e.g., a receiver, a speaker, a projector, a DVD player, or a television), media-playback devices (e.g., a compact disc player, a CD player, or the like), computing devices (e.g., a home computer, a laptop computer, a tablet, a personal digital assistant (PDA), a computing device, or a wearable device), lighting devices (e.g., a lamp or recessed lighting), devices associated with a security system, devices associated with an alarm system, devices that can be operated in an automobile (e.g., radio devices, navigation devices), and/or the like. Data may be collected from such various sensors in raw form, or data may be processed by the sensors to create parameters or other data either developed by the sensors based on the raw data or assigned to the system by a client or other controlling device.

In another example, another type of system that may include various sensors that collect data to be processed and/or transmitted to a computing environment according to certain embodiments includes a power or energy grid. A variety of different network devices may be included in an energy grid, such as various devices within one or more power plants, energy farms (e.g., wind farm, solar farm, among others) energy storage facilities, factories, homes and businesses of consumers, among others. One or more of such devices may include one or more sensors that detect energy gain or loss, electrical input or output or loss, and a variety of other efficiencies. These sensors may collect data to inform users of how the energy grid, and individual devices within the grid, may be functioning and how they may be made more efficient.

Network device sensors may also perform processing on data it collects before transmitting the data to the computing environment 114, or before deciding whether to transmit data to the computing environment 114. For example, network devices may determine whether data collected meets certain rules, for example by comparing data or values calculated from the data and comparing that data to one or more thresholds. The network device may use this data and/or comparisons to determine if the data should be transmitted to the computing environment 214 for further use or processing.

Computing environment 214 may include machines 220 and 240. Although computing environment 214 is shown in FIG. 2 as having two machines, 220 and 240, computing environment 214 may have only one machine or may have more than two machines. The machines that make up computing environment 214 may include specialized computers, servers, or other machines that are configured to individually and/or collectively process large amounts of data. The computing environment 214 may also include storage devices that include one or more databases of structured data, such as data organized in one or more hierarchies, or unstructured data. The databases may communicate with the processing devices within computing environment 214 to distribute data to them. Since network devices may transmit data to computing environment 214, that data may be received by the computing environment 214 and subsequently stored within those storage devices. Data used by computing environment 214 may also be stored in data stores 235, which may also be a part of or connected to computing environment 214.

Computing environment 214 can communicate with various devices via one or more routers 225 or other inter-network or intra-network connection components. For example, computing environment 214 may communicate with devices 230 via one or more routers 225. Computing environment 214 may collect, analyze and/or store data from or pertaining to communications, client device operations, client rules, and/or user-associated actions stored at one or more data stores 235. Such data may influence communication routing to the devices within computing environment 214, how data is stored or processed within computing environment 214, among other actions.

Notably, various other devices can further be used to influence communication routing and/or processing between devices within computing environment 214 and with devices outside of computing environment 214. For example, as shown in FIG. 2, computing environment 214 may include a web server 240. Thus, computing environment 214 can retrieve data of interest, such as client information (e.g., product information, client rules, etc.), technical product details, news, current or predicted weather, and so on.

In addition to computing environment 214 collecting data (e.g., as received from network devices, such as sensors, and client devices or other sources) to be processed as part of a big data analytics project, it may also receive data in real time as part of a streaming analytics environment. As noted, data may be collected using a variety of sources as communicated via different kinds of networks or locally. Such data may be received on a real-time streaming basis. For example, network devices may receive data periodically from network device sensors as the sensors continuously sense, monitor and track changes in their environments. Devices within computing environment 214 may also perform pre-analysis on data it receives to determine if the data received should be processed as part of an ongoing project. The data received and collected by computing environment 214, no matter what the source or method or timing of receipt, may be processed over a period of time for a client to determine results data based on the client's needs and rules.

Figure 3:
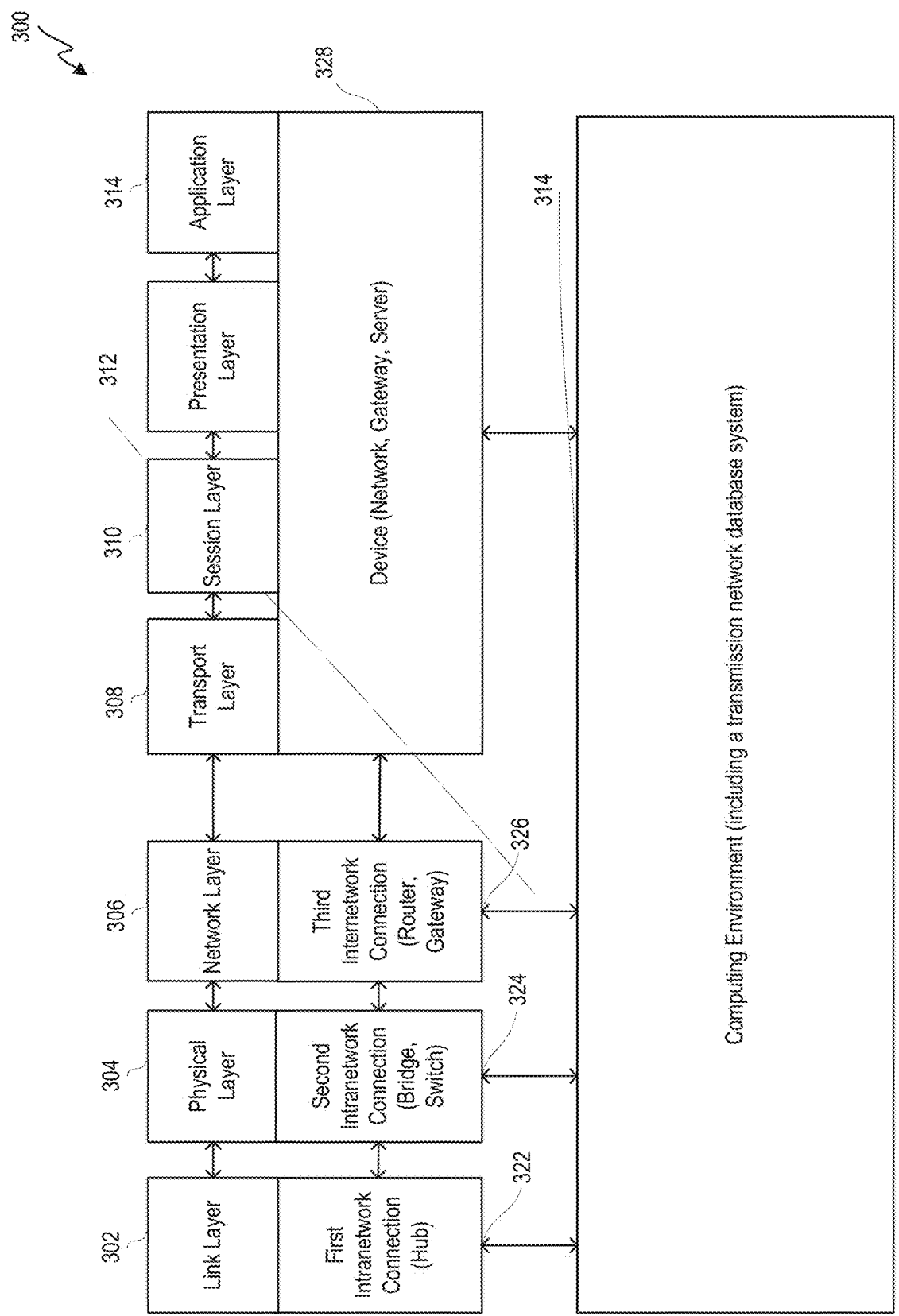
FIG. 3 illustrates a representation of a conceptual model of a communications protocol system, according to some embodiments of the present technology.

FIG. 3 illustrates a representation of a conceptual model of a communications protocol system, according to embodiments of the present technology. More specifically, FIG. 3 identifies operation of a computing environment in an Open Systems Interaction model that corresponds to various connection components. The model 300 shows, for example, how a computing environment, such as computing environment 314 (or computing environment 214 in FIG. 2) may communicate with other devices in its network, and control how communications between the computing environment and other devices are executed and under what conditions.

The model can include layers 302-314. The layers are arranged in a stack. Each layer in the stack serves the layer one level higher than it (except for the application layer, which is the highest layer), and is served by the layer one level below it (except for the physical layer, which is the lowest layer). The physical layer is the lowest layer because it receives and transmits raw bites of data, and is the farthest layer from the user in a communications system. On the other hand, the application layer is the highest layer because it interacts directly with a software application.

As noted, the model includes a physical layer 302. Physical layer 302 represents physical communication, and can define parameters of that physical communication. For example, such physical communication may come in the form of electrical, optical, or electromagnetic signals. Physical layer 302 also defines protocols that may control communications within a data transmission network.

Link layer 304 defines links and mechanisms used to transmit (i.e., move) data across a network. The link layer manages node-to-node communications, such as within a grid computing environment. Link layer 304 can detect and correct errors (e.g., transmission errors in the physical layer 302). Link layer 304 can also include a media access control (MAC) layer and logical link control (LLC) layer.

Network layer 306 defines the protocol for routing within a network. In other words, the network layer coordinates transferring data across nodes in a same network (e.g., such as a grid computing environment). Network layer 306 can also define the processes used to structure local addressing within the network.

Transport layer 308 can manage the transmission of data and the quality of the transmission and/or receipt of that data. Transport layer 308 can provide a protocol for transferring data, such as, for example, a Transmission Control Protocol (TCP). Transport layer 308 can assemble and disassemble data frames for transmission. The transport layer can also detect transmission errors occurring in the layers below it.

Session layer 310 can establish, maintain, and manage communication connections between devices on a network. In other words, the session layer controls the dialogues or nature of communications between network devices on the network. The session layer may also establish checkpointing, adjournment, termination, and restart procedures.

Presentation layer 312 can provide translation for communications between the application and network layers. In other words, this layer may encrypt, decrypt and/or format data based on data types known to be accepted by an application or network layer.

Application layer 314 interacts directly with software applications and end users, and manages communications between them. Application layer 314 can identify destinations, local resource states or availability and/or communication content or formatting using the applications.

Intra-network connection components 322 and 324 are shown to operate in lower levels, such as physical layer 302 and link layer 304, respectively. For example, a hub can operate in the physical layer, a switch can operate in the physical layer, and a router can operate in the network layer. Inter-network connection components 326 and 328 are shown to operate on higher levels, such as layers 306-314. For example, routers can operate in the network layer and network devices can operate in the transport, session, presentation, and application layers.

As noted, a computing environment 314 can interact with and/or operate on, in various embodiments, one, more, all or any of the various layers. For example, computing environment 314 can interact with a hub (e.g., via the link layer) so as to adjust which devices the hub communicates with. The physical layer may be served by the link layer, so it may implement such data from the link layer. For example, the computing environment 314 may control which devices it will receive data from. For example, if the computing environment 314 knows that a certain network device has turned off, broken, or otherwise become unavailable or unreliable, the computing environment 314 may instruct the hub to prevent any data from being transmitted to the computing environment 314 from that network device. Such a process may be beneficial to avoid receiving data that is inaccurate or that has been influenced by an uncontrolled environment. As another example, computing environment 314 can communicate with a bridge, switch, router or gateway and influence which device within the system (e.g., system 200) the component selects as a destination. In some embodiments, computing environment 314 can interact with various layers by exchanging communications with equipment operating on a particular layer by routing or modifying existing communications. In another embodiment, such as in a grid computing environment, a node may determine how data within the environment should be routed (e.g., which node should receive certain data) based on certain parameters or information provided by other layers within the model.

As noted, the computing environment 314 may be a part of a communications grid environment, the communications of which may be implemented as shown in the protocol of FIG. 3. For example, referring back to FIG. 2, one or more of machines 220 and 240 may be part of a communications grid computing environment. A gridded computing environment may be employed in a distributed system with non-interactive workloads where data resides in memory on the machines, or compute nodes. In such an environment, analytic code, instead of a database management system, controls the processing performed by the nodes. Data is co-located by pre-distributing it to the grid nodes, and the analytic code on each node loads the local data into memory. Each node may be assigned a particular task such as a portion of a processing project, or to organize or control other nodes within the grid.

Figure 4:
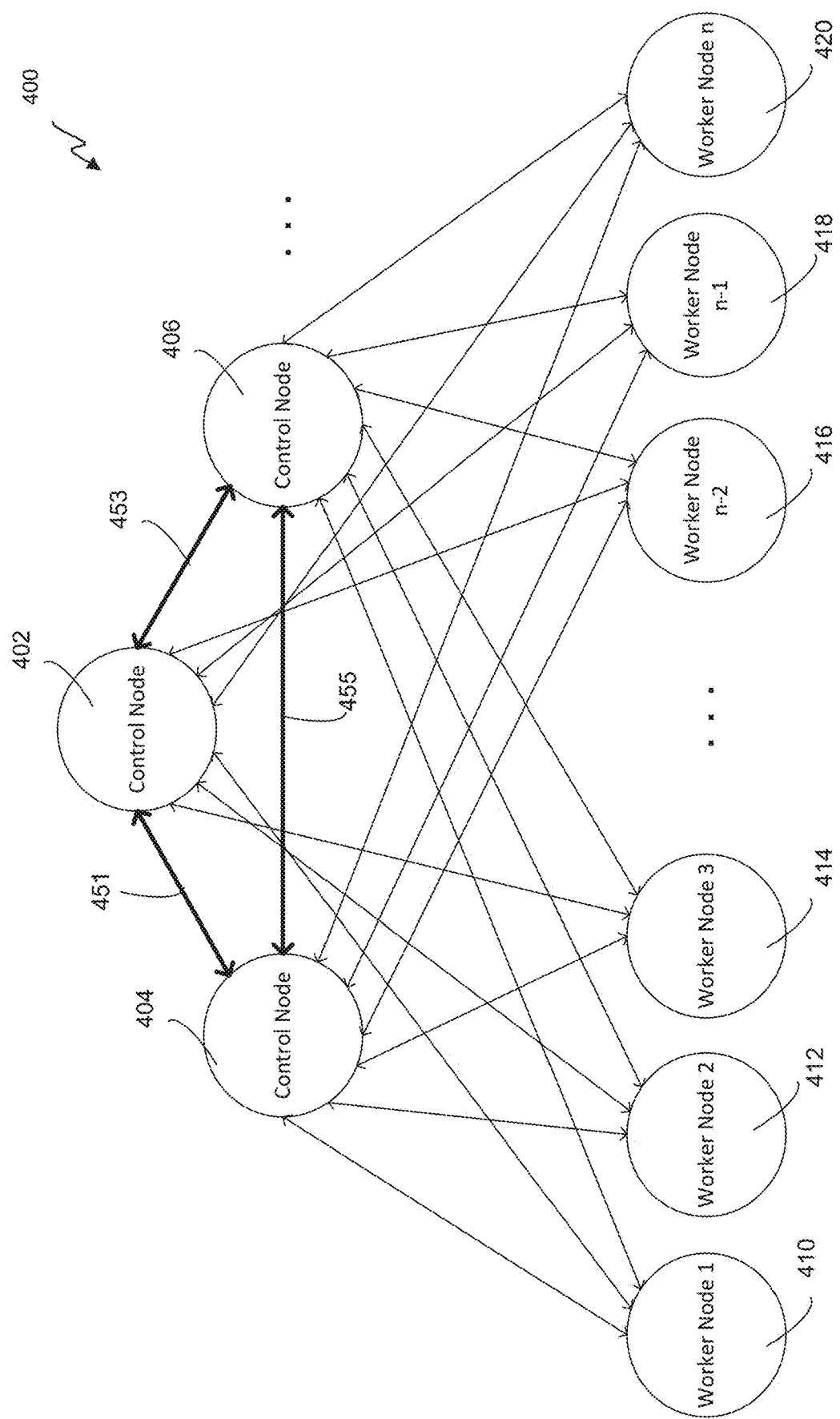
FIG. 4 illustrates a communications grid computing system including a variety of control and worker nodes, according to some embodiments of the present technology.

FIG. 4 illustrates a communications grid computing system 400 including a variety of control and worker nodes, according to embodiments of the present technology. Communications grid computing system 400 includes three control nodes and one or more worker nodes. Communications grid computing system 400 includes control nodes 402, 404, and 406. The control nodes are communicatively connected via communication paths 451, 453, and 455. Therefore, the control nodes may transmit information (e.g., related to the communications grid or notifications), to and receive information from each other. Although communications grid computing system 400 is shown in FIG. 4 as including three control nodes, the communications grid may include more or less than three control nodes.

Communications grid computing system (or just "communications grid") 400 also includes one or more worker nodes. Shown in FIG. 4 are six worker nodes 410-420. Although FIG. 4 shows six worker nodes, a communications grid according to embodiments of the present technology may include more or less than six worker nodes. The number of worker nodes included in a communications grid may be dependent upon how large the project or data set is being processed by the communications grid, the capacity of each worker node, the time designated for the communications grid to complete the project, among others. Each worker node within the communications grid 400 may be connected (wired or wirelessly, and directly or indirectly) to control nodes 402-406. Therefore, each worker node may receive information from the control nodes (e.g., an instruction to perform work on a project) and may transmit information to the control nodes (e.g., a result from work performed on a project). Furthermore, worker nodes may communicate with each other (either directly or indirectly). For example, worker nodes may transmit data between each other related to a job being performed or an individual task within a job being performed by that worker node. However, in certain embodiments, worker nodes may not, for example, be connected (communicatively or otherwise) to certain other worker nodes. In an embodiment, worker nodes may only be able to communicate with the control node that controls it, and may not be able to communicate with other worker nodes in the communications grid, whether they are other worker nodes controlled by the control node that controls the worker node, or worker nodes that are controlled by other control nodes in the communications grid.

A control node may connect with an external device with which the control node may communicate (e.g., a grid user, such as a server or computer, may connect to a controller of the grid). For example, a server or computer may connect to control nodes and may transmit a project or job to the node. The project may include a data set. The data set may be of any size. Once the control node receives such a project including a large data set, the control node may distribute the data set or projects related to the data set to be performed by worker nodes. Alternatively, for a project including a large data set, the data set may be receive or stored by a machine other than a control node (e.g., a Hadoop data node).

Control nodes may maintain knowledge of the status of the nodes in the grid (i.e., grid status information), accept work requests from clients, subdivide the work across worker nodes, coordinate the worker nodes, among other responsibilities. Worker nodes may accept work requests from a control node and provide the control node with results of the work performed by the worker node. A grid may be started from a single node (e.g., a machine, computer, server, etc.). This first node may be assigned or may start as the primary control node that will control any additional nodes that enter the grid.

When a project is submitted for execution (e.g., by a client or a controller of the grid) it may be assigned to a set of nodes. After the nodes are assigned to a project, a data structure (i.e., a communicator) may be created. The communicator may be used by the project for information to be shared between the project code running on each node. A communication handle may be created on each node. A handle, for example, is a reference to the communicator that is valid within a single process on a single node, and the handle may be used when requesting communications between nodes.

A control node, such as control node 402, may be designated as the primary control node. A server, computer or other external device may connect to the primary control node. Once the control node receives a project, the primary control node may distribute portions of the project to its worker nodes for execution. For example, when a project is initiated on communications grid 400, primary control node 402 controls the work to be performed for the project in order to complete the project as requested or instructed. The primary control node may distribute work to the worker nodes based on various factors, such as which subsets or portions of projects may be completed most efficiently and in the correct amount of time. For example, a worker node may perform analysis on a portion of data that is already local (e.g., stored on) the worker node. The primary control node also coordinates and processes the results of the work performed by each worker node after each worker node executes and completes its job. For example, the primary control node may receive a result from one or more worker nodes, and the control node may organize (e.g., collect and assemble) the results received and compile them to produce a complete result for the project received from the end user.

Any remaining control nodes, such as control nodes 404 and 406, may be assigned as backup control nodes for the project. In an embodiment, backup control nodes may not control any portion of the project. Instead, backup control nodes may serve as a backup for the primary control node and take over as primary control node if the primary control node were to fail. If a communications grid were to include only a single control node, and the control node were to fail (e.g., the control node is shut off or breaks) then the communications grid as a whole may fail and any project or job being run on the communications grid may fail and may not complete. While the project may be run again, such a failure may cause a delay (severe delay in some cases, such as overnight delay) in completion of the project. Therefore, a grid with multiple control nodes, including a backup control node, may be beneficial.

To add another node or machine to the grid, the primary control node may open a pair of listening sockets, for example. A socket may be used to accept work requests from clients, and the second socket may be used to accept connections from other grid nodes). The primary control node may be provided with a list of other nodes (e.g., other machines, computers, servers) that will participate in the grid, and the role that each node will fill in the grid. Upon startup of the primary control node (e.g., the first node on the grid), the primary control node may use a network protocol to start the server process on every other node in the grid. Command line parameters, for example, may inform each node of one or more pieces of information, such as: the role that the node will have in the grid, the host name of the primary control node, the port number on which the primary control node is accepting connections from peer nodes, among others. The information may also be provided in a configuration file, transmitted over a secure shell tunnel, recovered from a configuration server, among others. While the other machines in the grid may not initially know about the configuration of the grid, that information may also be sent to each other node by the primary control node. Updates of the grid information may also be subsequently sent to those nodes.

For any control node other than the primary control node added to the grid, the control node may open three sockets. The first socket may accept work requests from clients, the second socket may accept connections from other grid members, and the third socket may connect (e.g., permanently) to the primary control node. When a control node (e.g., primary control node) receives a connection from another control node, it first checks to see if the peer node is in the list of configured nodes in the grid. If it is not on the list, the control node may clear the connection. If it is on the list, it may then attempt to authenticate the connection. If authentication is successful, the authenticating node may transmit information to its peer, such as the port number on which a node is listening for connections, the host name of the node, information about how to authenticate the node, among other information. When a node, such as the new control node, receives information about another active node, it will check to see if it already has a connection to that other node. If it does not have a connection to that node, it may then establish a connection to that control node.

Any worker node added to the grid may establish a connection to the primary control node and any other control nodes on the grid. After establishing the connection, it may authenticate itself to the grid (e.g., any control nodes, including both primary and backup, or a server or user controlling the grid). After successful authentication, the worker node may accept configuration information from the control node.

When a node joins a communications grid (e.g., when the node is powered on or connected to an existing node on the grid or both), the node is assigned (e.g., by an operating system of the grid) a universally unique identifier (UUID). This unique identifier may help other nodes and external entities (devices, users, etc.) to identify the node and distinguish it from other nodes. When a node is connected to the grid, the node may share its unique identifier with the other nodes in the grid. Since each node may share its unique identifier, each node may know the unique identifier of every other node on the grid. Unique identifiers may also designate a hierarchy of each of the nodes (e.g., backup control nodes) within the grid. For example, the unique identifiers of each of the backup control nodes may be stored in a list of backup control nodes to indicate an order in which the backup control nodes will take over for a failed primary control node to become a new primary control node. However, a hierarchy of nodes may also be determined using methods other than using the unique identifiers of the nodes. For example, the hierarchy may be predetermined, or may be assigned based on other predetermined factors.

The grid may add new machines at any time (e.g., initiated from any control node). Upon adding a new node to the grid, the control node may first add the new node to its table of grid nodes. The control node may also then notify every other control node about the new node. The nodes receiving the notification may acknowledge that they have updated their configuration information.

Primary control node 402 may, for example, transmit one or more communications to backup control nodes 404 and 406 (and, for example, to other control or worker nodes within the communications grid). Such communications may sent periodically, at fixed time intervals, between known fixed stages of the project's execution, among other protocols. The communications transmitted by primary control node 402 may be of varied types and may include a variety of types of information. For example, primary control node 402 may transmit snapshots (e.g., status information) of the communications grid so that backup control node 404 always has a recent snapshot of the communications grid. The snapshot or grid status may include, for example, the structure of the grid (including, for example, the worker nodes in the grid, unique identifiers of the nodes, or their relationships with the primary control node) and the status of a project (including, for example, the status of each worker node's portion of the project). The snapshot may also include analysis or results received from worker nodes in the communications grid. The backup control nodes may receive and store the backup data received from the primary control node. The backup control nodes may transmit a request for such a snapshot (or other information) from the primary control node, or the primary control node may send such information periodically to the backup control nodes.

As noted, the backup data may allow the backup control node to take over as primary control node if the primary control node fails without requiring the grid to start the project over from scratch. If the primary control node fails, the backup control node that will take over as primary control node may retrieve the most recent version of the snapshot received from the primary control node and use the snapshot to continue the project from the stage of the project indicated by the backup data. This may prevent failure of the project as a whole.

A backup control node may use various methods to determine that the primary control node has failed. In one example of such a method, the primary control node may transmit (e.g., periodically) a communication to the backup control node that indicates that the primary control node is working and has not failed, such as a heartbeat communication. The backup control node may determine that the primary control node has failed if the backup control node has not received a heartbeat communication for a certain predetermined period of time. Alternatively, a backup control node may also receive a communication from the primary control node itself (before it failed) or from a worker node that the primary control node has failed, for example because the primary control node has failed to communicate with the worker node.

Different methods may be performed to determine which backup control node of a set of backup control nodes (e.g., backup control nodes 404 and 406) will take over for failed primary control node 402 and become the new primary control node. For example, the new primary control node may be chosen based on a ranking or "hierarchy" of backup control nodes based on their unique identifiers. In an alternative embodiment, a backup control node may be assigned to be the new primary control node by another device in the communications grid or from an external device (e.g., a system infrastructure or an end user, such as a server or computer, controlling the communications grid). In another alternative embodiment, the backup control node that takes over as the new primary control node may be designated based on bandwidth or other statistics about the communications grid.

A worker node within the communications grid may also fail. If a worker node fails, work being performed by the failed worker node may be redistributed amongst the operational worker nodes. In an alternative embodiment, the primary control node may transmit a communication to each of the operable worker nodes still on the communications grid that each of the worker nodes should purposefully fail also. After each of the worker nodes fail, they may each retrieve their most recent saved checkpoint of their status and restart the project from that checkpoint to minimize lost progress on the project being executed.

FIG. 5 illustrates a flow chart showing an example process for adjusting a communications grid or a work project in a communications grid after a failure of a node, according to embodiments of the present technology. The process may include, for example, receiving grid status information including a project status of a portion of a project being executed by a node in the communications grid, as described in operation 502. For example, a control node (e.g., a backup control node connected to a primary control node and a worker node on a communications grid) may receive grid status information, where the grid status information includes a project status of the primary control node or a project status of the worker node. The project status of the primary control node and the project status of the worker node may include a status of one or more portions of a project being executed by the primary and worker nodes in the communications grid. The process may also include storing the grid status information, as described in operation 504. For example, a control node (e.g., a backup control node) may store the received grid status information locally within the control node. Alternatively, the grid status information may be sent to another device for storage where the control node may have access to the information.

The process may also include receiving a failure communication corresponding to a node in the communications grid in operation 506. For example, a node may receive a failure communication including an indication that the primary control node has failed, prompting a backup control node to take over for the primary control node. In an alternative embodiment, a node may receive a failure that a worker node has failed, prompting a control node to reassign the work being performed by the worker node. The process may also include reassigning a node or a portion of the project being executed by the failed node, as described in operation 508. For example, a control node may designate the backup control node as a new primary control node based on the failure communication upon receiving the failure communication. If the failed node is a worker node, a control node may identify a project status of the failed worker node using the snapshot of the communications grid, where the project status of the failed worker node includes a status of a portion of the project being executed by the failed worker node at the failure time.

The process may also include receiving updated grid status information based on the reassignment, as described in operation 510, and transmitting a set of instructions based on the updated grid status information to one or more nodes in the communications grid, as described in operation 512. The updated grid status information may include an updated project status of the primary control node or an updated project status of the worker node. The updated information may be transmitted to the other nodes in the grid to update their stale stored information.

Figure 6:
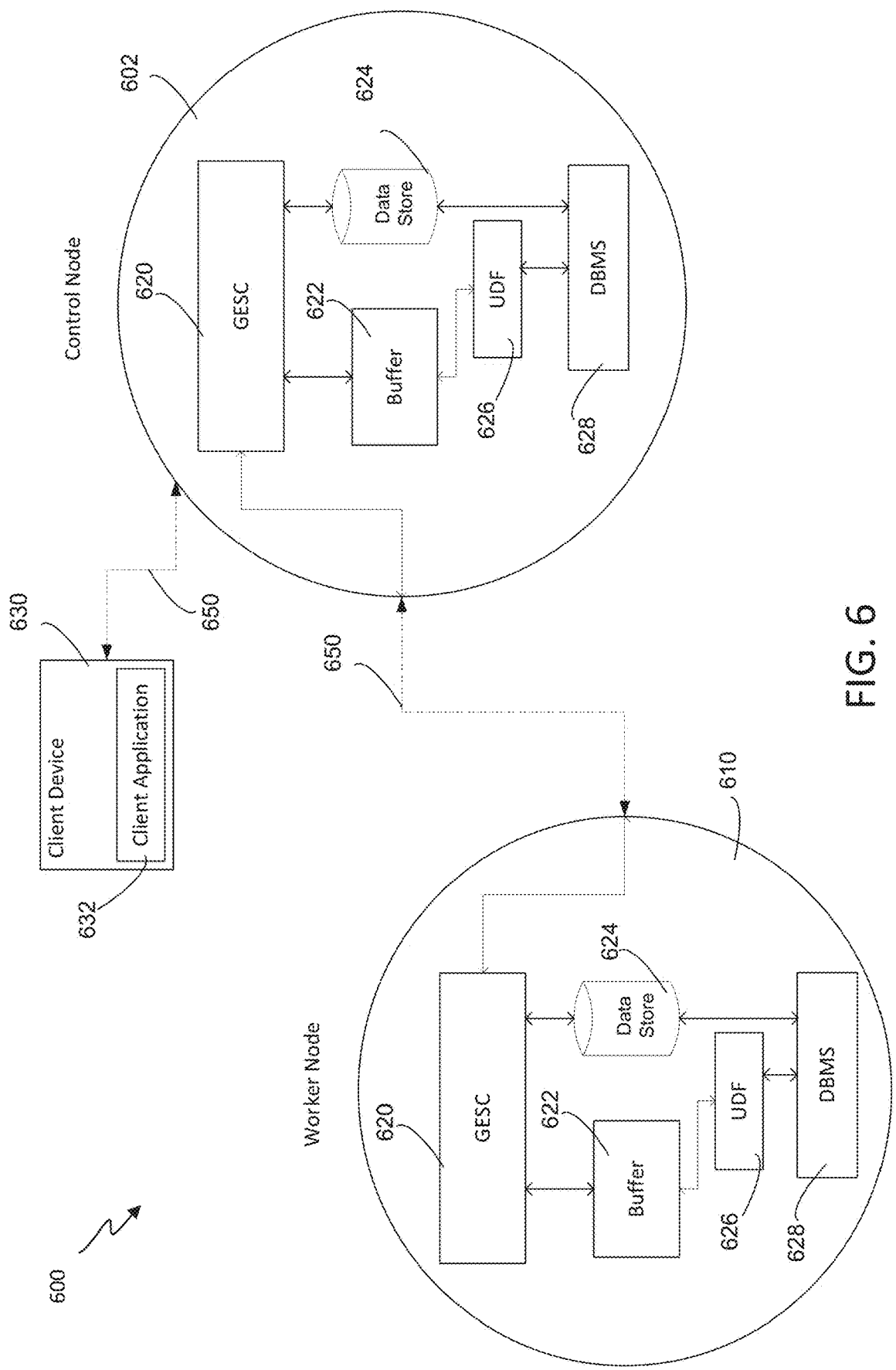
FIG. 6 illustrates a portion of a communications grid computing system including a control node and a worker node, according to some embodiments of the present technology.

FIG. 6 illustrates a portion of a communications grid computing system 600 including a control node and a worker node, according to embodiments of the present technology. Communications grid 600 computing system includes one control node (control node 602) and one worker node (worker node 610) for purposes of illustration, but may include more worker and/or control nodes. The control node 602 is communicatively connected to worker node 610 via communication path 650. Therefore, control node 602 may transmit information (e.g., related to the communications grid or notifications), to and receive information from worker node 610 via path 650.

Similar to in FIG. 4, communications grid computing system (or just "communications grid") 600 includes data processing nodes (control node 602 and worker node 610). Nodes 602 and 610 comprise multi-core data processors. Each node 602 and 610 includes a grid-enabled software component (GESC) 620 that executes on the data processor associated with that node and interfaces with buffer memory 622 also associated with that node. Each node 602 and 610 includes a database management software (DBMS) 628 that executes on a database server (not shown) at control node 602 and on a database server (not shown) at worker node 610.

Each node also includes a data store 624. Data stores 624, similar to network-attached data stores 110 in FIG. 1 and data stores 235 in FIG. 2, are used to store data to be processed by the nodes in the computing environment. Data stores 624 may also store any intermediate or final data generated by the computing system after being processed, for example in non-volatile memory. However in certain embodiments, the configuration of the grid computing environment allows its operations to be performed such that intermediate and final data results can be stored solely in volatile memory (e.g., RAM), without a requirement that intermediate or final data results be stored to non-volatile types of memory. Storing such data in volatile memory may be useful in certain situations, such as when the grid receives queries (e.g., ad hoc) from a client and when responses, which are generated by processing large amounts of data, need to be generated quickly or on-the-fly. In such a situation, the grid may be configured to retain the data within memory so that responses can be generated at different levels of detail and so that a client may interactively query against this information.

Each node also includes a user-defined function (UDF) 626. The UDF provides a mechanism for the DMBS 628 to transfer data to or receive data from the database stored in the data stores 624 that are managed by the DBMS. For example, UDF 626 can be invoked by the DBMS to provide data to the GESC for processing. The UDF 626 may establish a socket connection (not shown) with the GESC to transfer the data. Alternatively, the UDF 626 can transfer data to the GESC by writing data to shared memory accessible by both the UDF and the GESC.

The GESC 620 at the nodes 602 and 620 may be connected via a network, such as network 108 shown in FIG. 1. Therefore, nodes 602 and 620 can communicate with each other via the network using a predetermined communication protocol such as, for example, the Message Passing Interface (MPI). Each GESC 620 can engage in point-to-point communication with the GESC at another node or in collective communication with multiple GESCs via the network. The GESC 620 at each node may contain identical (or nearly identical) software instructions. Each node may be capable of operating as either a control node or a worker node. The GESC at the control node 602 can communicate, over a communication path 652, with a client device 630. More specifically, control node 602 may communicate with client application 632 hosted by the client device 630 to receive queries and to respond to those queries after processing large amounts of data.

DMBS 628 may control the creation, maintenance, and use of database or data structure (not shown) within a nodes 602 or 610. The database may organize data stored in data stores 624. The DMBS 628 at control node 602 may accept requests for data and transfer the appropriate data for the request. With such a process, collections of data may be distributed across multiple physical locations. In this example, each node 602 and 610 stores a portion of the total data managed by the management system in its associated data store 624.

Furthermore, the DBMS may be responsible for protecting against data loss using replication techniques. Replication includes providing a backup copy of data stored on one node on one or more other nodes. Therefore, if one node fails, the data from the failed node can be recovered from a replicated copy residing at another node. However, as described herein with respect to FIG. 4, data or status information for each node in the communications grid may also be shared with each node on the grid.

Figure 7:
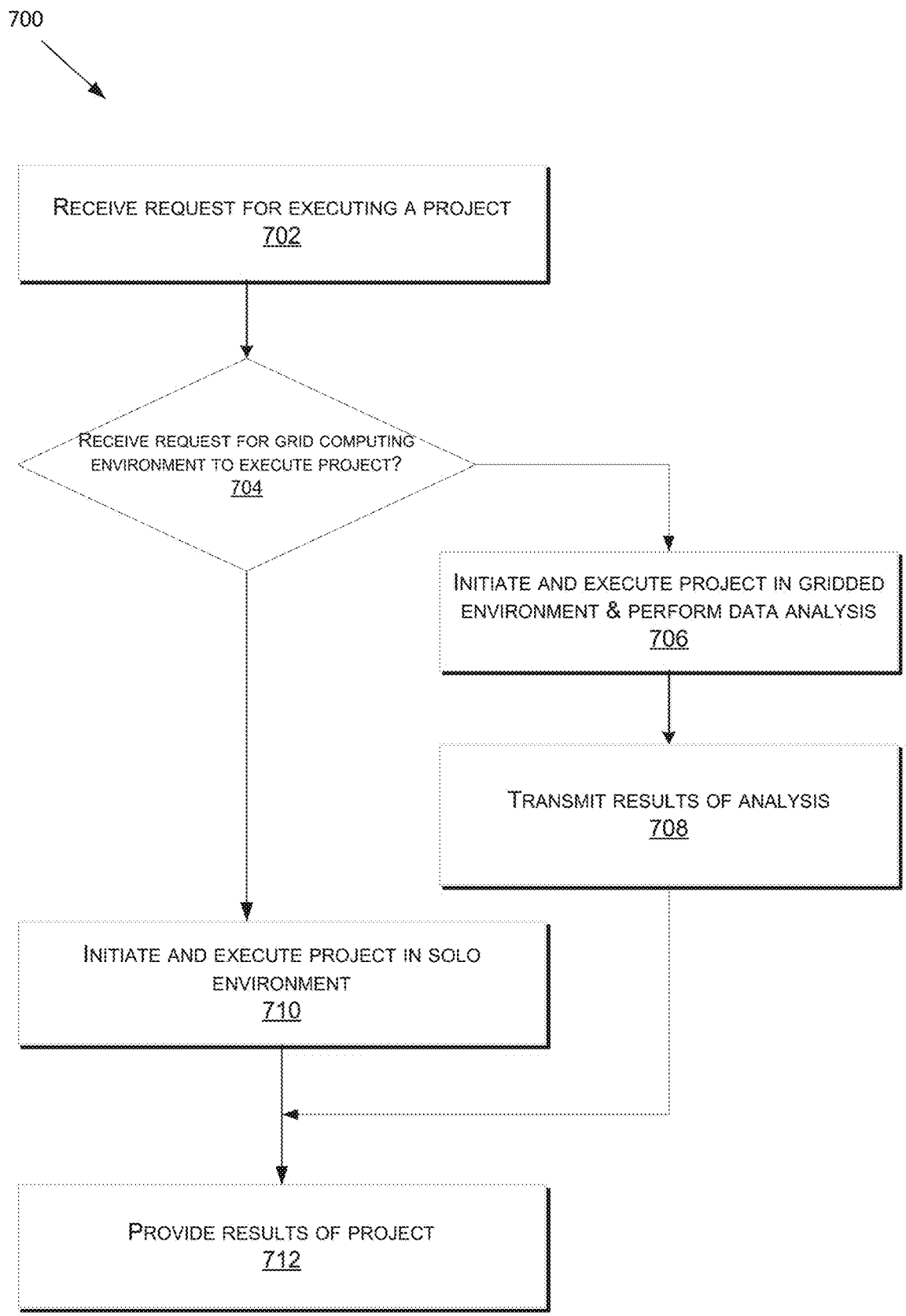
FIG. 7 illustrates a flow chart showing an example process for executing a data analysis or processing project, according to some embodiments of the present technology.

FIG. 7 illustrates a flow chart showing an example method for executing a project within a grid computing system, according to embodiments of the present technology. As described with respect to FIG. 6, the GESC at the control node may transmit data with a client device (e.g., client device 630) to receive queries for executing a project and to respond to those queries after large amounts of data have been processed. The query may be transmitted to the control node, where the query may include a request for executing a project, as described in operation 702. The query can contain instructions on the type of data analysis to be performed in the project and whether the project should be executed using the grid-based computing environment, as shown in operation 704.

To initiate the project, the control node may determine if the query requests use of the grid-based computing environment to execute the project. If the determination is no, then the control node initiates execution of the project in a solo environment (e.g., at the control node), as described in operation 710. If the determination is yes, the control node may initiate execution of the project in the grid-based computing environment, as described in operation 706. In such a situation, the request may include a requested configuration of the grid. For example, the request may include a number of control nodes and a number of worker nodes to be used in the grid when executing the project. After the project has been completed, the control node may transmit results of the analysis yielded by the grid, as described in operation 708. Whether the project is executed in a solo or grid-based environment, the control node provides the results of the project.

As noted with respect to FIG. 2, the computing environments described herein may collect data (e.g., as received from network devices, such as sensors, such as network devices 204-209 in FIG. 2, and client devices or other sources) to be processed as part of a data analytics project, and data may be received in real time as part of a streaming analytics environment (e.g., ESP). Data may be collected using a variety of sources as communicated via different kinds of networks or locally, such as on a real-time streaming basis. For example, network devices may receive data periodically from network device sensors as the sensors continuously sense, monitor and track changes in their environments. More specifically, an increasing number of distributed applications develop or produce continuously flowing data from distributed sources by applying queries to the data before distributing the data to geographically distributed recipients. An event stream processing engine (ESPE) may continuously apply the queries to the data as it is received and determines which entities should receive the data. Client or other devices may also subscribe to the ESPE or other devices processing ESP data so that they can receive data after processing, based on for example the entities determined by the processing engine. For example, client devices 230 in FIG. 2 may subscribe to the ESPE in computing environment 214. In another example, event subscription devices 874*a-c*, described further with respect to FIG. 10, may also subscribe to the ESPE. The ESPE may determine or define how input data or event streams from network devices or other publishers (e.g., network devices 204-209 in FIG. 2) are transformed into meaningful output data to be consumed by subscribers, such as for example client devices 230 in FIG. 2.

FIG. 8 illustrates a block diagram including components of an Event Stream Processing Engine (ESPE), according to embodiments of the present technology. ESPE 800 may include one or more projects 802. A project may be described as a second-level container in an engine model managed by ESPE 800 where a thread pool size for the project may be defined by a user. Each project of the one or more projects 802 may include one or more continuous queries 804 that contain data flows, which are data transformations of incoming event streams. The one or more continuous queries 804 may include one or more source windows 806 and one or more derived windows 808.

The ESPE may receive streaming data over a period of time related to certain events, such as events or other data sensed by one or more network devices. The ESPE may perform operations associated with processing data created by the one or more devices. For example, the ESPE may receive data from the one or more network devices 204-209 shown in FIG. 2. As noted, the network devices may include sensors that sense different aspects of their environments, and may collect data over time based on those sensed observations. For example, the ESPE may be implemented within one or more of machines 220 and 240 shown in FIG. 2. The ESPE may be implemented within such a machine by an ESP application. An ESP application may embed an ESPE with its own dedicated thread pool or pools into its application space where the main application thread can do application-specific work and the ESPE processes event streams at least by creating an instance of a model into processing objects.

The engine container is the top-level container in a model that manages the resources of the one or more projects 802. In an illustrative embodiment, for example, there may be only one ESPE 800 for each instance of the ESP application, and ESPE 800 may have a unique engine name. Additionally, the one or more projects 802 may each have unique project names, and each query may have a unique continuous query name and begin with a uniquely named source window of the one or more source windows 806. ESPE 800 may or may not be persistent.

Continuous query modeling involves defining directed graphs of windows for event stream manipulation and transformation. A window in the context of event stream manipulation and transformation is a processing node in an event stream processing model. A window in a continuous query can perform aggregations, computations, pattern-matching, and other operations on data flowing through the window. A continuous query may be described as a directed graph of source, relational, pattern matching, and procedural windows. The one or more source windows 806 and the one or more derived windows 808 represent continuously executing queries that generate updates to a query result set as new event blocks stream through ESPE 800. A directed graph, for example, is a set of nodes connected by edges, where the edges have a direction associated with them.

An event object may be described as a packet of data accessible as a collection of fields, with at least one of the fields defined as a key or unique identifier (ID). The event object may be created using a variety of formats including binary, alphanumeric, XML, etc. Each event object may include one or more fields designated as a primary identifier (ID) for the event so ESPE 800 can support operation codes (opcodes) for events including insert, update, upsert, and delete. Upsert opcodes update the event if the key field already exists; otherwise, the event is inserted. For illustration, an event object may be a packed binary representation of a set of field values and include both metadata and field data associated with an event. The metadata may include an opcode indicating if the event represents an insert, update, delete, or upsert, a set of flags indicating if the event is a normal, partial-update, or a retention generated event from retention policy management, and a set of microsecond timestamps that can be used for latency measurements.

An event block object may be described as a grouping or package of event objects. An event stream may be described as a flow of event block objects. A continuous query of the one or more continuous queries 804 transforms a source event stream made up of streaming event block objects published into ESPE 800 into one or more output event streams using the one or more source windows 806 and the one or more derived windows 808. A continuous query can also be thought of as data flow modeling.

The one or more source windows 806 are at the top of the directed graph and have no windows feeding into them. Event streams are published into the one or more source windows 806, and from there, the event streams may be directed to the next set of connected windows as defined by the directed graph. The one or more derived windows 808 are all instantiated windows that are not source windows and that have other windows streaming events into them. The one or more derived windows 808 may perform computations or transformations on the incoming event streams. The one or more derived windows 808 transform event streams based on the window type (that is operators such as join, filter, compute, aggregate, copy, pattern match, procedural, union, etc.) and window settings. As event streams are published into ESPE 800, they are continuously queried, and the resulting sets of derived windows in these queries are continuously updated.

FIG. 9 illustrates a flow chart showing an example process including operations performed by an event stream processing engine, according to some embodiments of the present technology. As noted, the ESPE 800 (or an associated ESP application) defines how input event streams are transformed into meaningful output event streams. More specifically, the ESP application may define how input event streams from publishers (e.g., network devices providing sensed data) are transformed into meaningful output event streams consumed by subscribers (e.g., a data analytics project being executed by a machine or set of machines).

Within the application, a user may interact with one or more user interface windows presented to the user in a display under control of the ESPE independently or through a browser application in an order selectable by the user. For example, a user may execute an ESP application, which causes presentation of a first user interface window, which may include a plurality of menus and selectors such as drop down menus, buttons, text boxes, hyperlinks, etc. associated with the ESP application as understood by a person of skill in the art. As further understood by a person of skill in the art, various operations may be performed in parallel, for example, using a plurality of threads.

At operation 900, an ESP application may define and start an ESPE, thereby instantiating an ESPE at a device, such as machine 220 and/or 240. In an operation 902, the engine container is created. For illustration, ESPE 800 may be instantiated using a function call that specifies the engine container as a manager for the model.

In an operation 904, the one or more continuous queries 804 are instantiated by ESPE 800 as a model. The one or more continuous queries 804 may be instantiated with a dedicated thread pool or pools that generate updates as new events stream through ESPE 800. For illustration, the one or more continuous queries 804 may be created to model business processing logic within ESPE 800, to predict events within ESPE 800, to model a physical system within ESPE 800, to predict the physical system state within ESPE 800, etc. For example, as noted, ESPE 800 may be used to support sensor data monitoring and management (e.g., sensing may include force, torque, load, strain, position, temperature, air pressure, fluid flow, chemical properties, resistance, electromagnetic fields, radiation, irradiance, proximity, acoustics, moisture, distance, speed, vibrations, acceleration, electrical potential, or electrical current, etc.).

ESPE 800 may analyze and process events in motion or "event streams." Instead of storing data and running queries against the stored data, ESPE 800 may store queries and stream data through them to allow continuous analysis of data as it is received. The one or more source windows 806 and the one or more derived windows 808 may be created based on the relational, pattern matching, and procedural algorithms that transform the input event streams into the output event streams to model, simulate, score, test, predict, etc. based on the continuous query model defined and application to the streamed data.

In an operation 906, a publish/subscribe (pub/sub) capability is initialized for ESPE 800. In an illustrative embodiment, a pub/sub capability is initialized for each project of the one or more projects 802. To initialize and enable pub/sub capability for ESPE 800, a port number may be provided. Pub/sub clients can use a host name of an ESP device running the ESPE and the port number to establish pub/sub connections to ESPE 800.

FIG. 10 illustrates an ESP system 850 interfacing between publishing device 872 and event subscribing devices 874a-c, according to embodiments of the present technology. ESP system 850 may include ESP device or subsystem 851, event publishing device 872, an event subscribing device A 874a, an event subscribing device B 874b, and an event subscribing device C 874c. Input event streams are output to ESP device 851 by publishing device 872. In alternative embodiments, the input event streams may be created by a plurality of publishing devices. The plurality of publishing devices further may publish event streams to other ESP devices. The one or more continuous queries instantiated by ESPE 800 may analyze and process the input event streams to form output event streams output to event subscribing device A 874a, event subscribing device B 874b, and event subscribing device C 874c. ESP system 850 may include a greater or a fewer number of event subscribing devices of event subscribing devices.

Publish-subscribe is a message-oriented interaction paradigm based on indirect addressing. Processed data recipients specify their interest in receiving information from ESPE 800 by subscribing to specific classes of events, while information sources publish events to ESPE 800 without directly addressing the receiving parties. ESPE 800 coordinates the interactions and processes the data. In some cases, the data source receives confirmation that the published information has been received by a data recipient.

A publish/subscribe API may be described as a library that enables an event publisher, such as publishing device 872, to publish event streams into ESPE 800 or an event subscriber, such as event subscribing device A 874a, event subscribing device B 874b, and event subscribing device C 874c, to subscribe to event streams from ESPE 800. For illustration, one or more publish/subscribe APIs may be defined. Using the publish/subscribe API, an event publishing application may publish event streams into a running event stream processor project source window of ESPE 800, and the event subscription application may subscribe to an event stream processor project source window of ESPE 800.

The publish/subscribe API provides cross-platform connectivity and endianness compatibility between ESP application and other networked applications, such as event publishing applications instantiated at publishing device 872, and event subscription applications instantiated at one or more of event subscribing device A 874a, event subscribing device B 874b, and event subscribing device C 874c.

Referring back to FIG. 9, operation 906 initializes the publish/subscribe capability of ESPE 800. In an operation 908, the one or more projects 802 are started. The one or more started projects may run in the background on an ESP device. In an operation 910, an event block object is received from one or more computing device of the event publishing device 872.

ESP subsystem 800 may include a publishing client 852, ESPE 800, a subscribing client A 854, a subscribing client B 856, and a subscribing client C 858. Publishing client 852 may be started by an event publishing application executing at publishing device 872 using the publish/subscribe API. Subscribing client A 854 may be started by an event subscription application A, executing at event subscribing device A 874a using the publish/subscribe API. Subscribing client B 856 may be started by an event subscription application B executing at event subscribing device B 874b using the publish/subscribe API. Subscribing client C 858 may be started by an event subscription application C executing at event subscribing device C 874c using the publish/subscribe API.

An event block object containing one or more event objects is injected into a source window of the one or more source windows 806 from an instance of an event publishing application on event publishing device 872. The event block object may generated, for example, by the event publishing application and may be received by publishing client 852. A unique ID may be maintained as the event block object is passed between the one or more source windows 806 and/or the one or more derived windows 808 of ESPE 800, and to subscribing client A 854, subscribing client B 806, and subscribing client C 808 and to event subscription device A 874a, event subscription device B 874b, and event subscription device C 874c. Publishing client 852 may further generate and include a unique embedded transaction ID in the event block object as the event block object is processed by a continuous query, as well as the unique ID that publishing device 872 assigned to the event block object.

In an operation 912, the event block object is processed through the one or more continuous queries 804. In an operation 914, the processed event block object is output to one or more computing devices of the event subscribing devices 874a-c. For example, subscribing client A 804, subscribing client B 806, and subscribing client C 808 may send the received event block object to event subscription device A 874a, event subscription device B 874b, and event subscription device C 874c, respectively.

ESPE 800 maintains the event block containership aspect of the received event blocks from when the event block is published into a source window and works its way through the directed graph defined by the one or more continuous queries 804 with the various event translations before being output to subscribers. Subscribers can correlate a group of subscribed events back to a group of published events by comparing the unique ID of the event block object that a publisher, such as publishing device 872, attached to the event block object with the event block ID received by the subscriber.

In an operation 916, a determination is made concerning whether or not processing is stopped. If processing is not stopped, processing continues in operation 910 to continue receiving the one or more event streams containing event block objects from the, for example, one or more network devices. If processing is stopped, processing continues in an operation 918. In operation 918, the started projects are stopped. In operation 920, the ESPE is shutdown.

As noted, in some embodiments, big data is processed for an analytics project after the data is received and stored. In other embodiments, distributed applications process continuously flowing data in real-time from distributed sources by applying queries to the data before distributing the data to geographically distributed recipients. As noted, an event stream processing engine (ESPE) may continuously apply the queries to the data as it is received and determines which entities receive the processed data. This allows for large amounts of data being received and/or collected in a variety of environments to be processed and distributed in real time. For example, as shown with respect to FIG. 2, data may be collected from network devices that may include devices within the internet of things, such as devices within a home automation network. However, such data may be collected from a variety of different resources in a variety of different environments. In any such situation, embodiments of the present technology allow for real-time processing of such data.

Aspects of the current disclosure provide technical solutions to technical problems, such as computing problems that arise when an ESP device fails which results in a complete service interruption and potentially significant data loss. The data loss can be catastrophic when the streamed data is supporting mission critical operations such as those in support of an ongoing manufacturing or drilling operation. An embodiment of an ESP system achieves a rapid and seamless failover of ESPE running at the plurality of ESP devices without service interruption or data loss, thus significantly improving the reliability of an operational system that relies on the live or real-time processing of the data streams. The event publishing systems, the event subscribing systems, and each ESPE not executing at a failed ESP device are not aware of or effected by the failed ESP device. The ESP system may include thousands of event publishing systems and event subscribing systems. The ESP system keeps the failover logic and awareness within the boundaries of out-messaging network connector and out-messaging network device.

In one example embodiment, a system is provided to support a failover when event stream processing (ESP) event blocks. The system includes, but is not limited to, an out-messaging network device and a computing device. The computing device includes, but is not limited to, a processor and a computer-readable medium operably coupled to the processor. The processor is configured to execute an ESP engine (ESPE). The computer-readable medium has instructions stored thereon that, when executed by the processor, cause the computing device to support the failover. An event block object is received from the ESPE that includes a unique identifier. A first status of the computing device as active or standby is determined. When the first status is active, a second status of the computing device as newly active or not newly active is determined Newly active is determined when the computing device is switched from a standby status to an active status. When the second status is newly active, a last published event block object identifier that uniquely identifies a last published event block object is determined. A next event block object is selected from a non-transitory computer-readable medium accessible by the computing device. The next event block object has an event block object identifier that is greater than the determined last published event block object identifier. The selected next event block object is published to an out-messaging network device. When the second status of the computing device is not newly active, the received event block object is published to the out-messaging network device. When the first status of the computing device is standby, the received event block object is stored in the non-transitory computer-readable medium.

Figure 11:
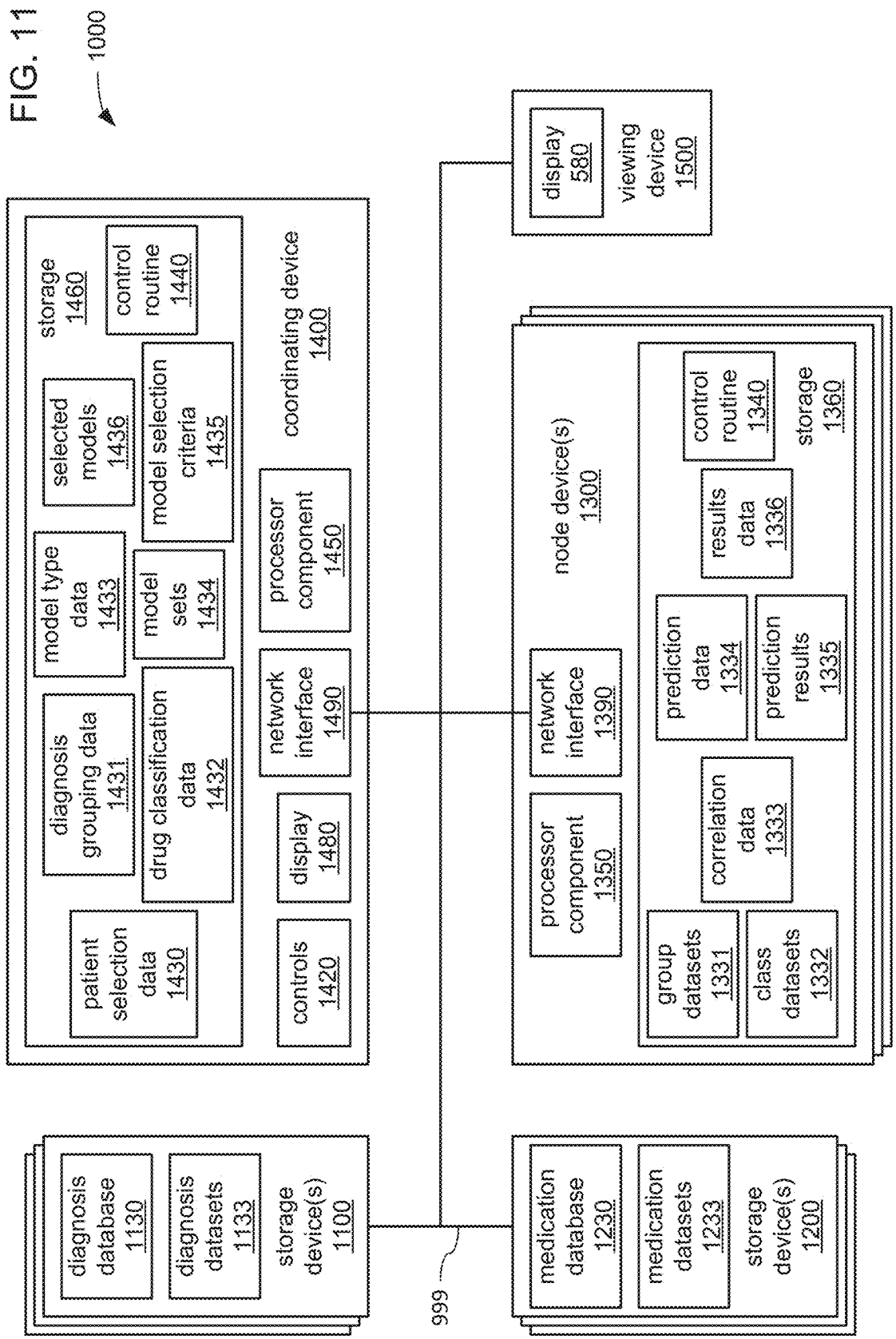
FIG. 11 illustrates an example embodiment of a prescription fraud detection system.

FIG. 11 illustrates a block diagram of an example embodiment of a prescription fraud detection system 1000 incorporating one or more storage devices 1100, one or more storage devices 1200, one or more node devices 1300, a coordinating device 1400, and/or a viewing device 1500. As depicted, these devices 1100, 1200, 1300, 1400 and/or 1500 may exchange at least a portion of a diagnosis database 1130, and at least a portion of a medication database 1230, as well as other data indicative of models generated and results derived from the use of models in detecting suspicious prescription filling patterns via a network 1999. However, it should be noted that one or more of the devices 1100, 1200, 1300, 1400 and/or 1500 may exchange other data entirely unrelated to medical histories and/or detecting suspicious prescription filling patterns thereamong or with still other devices (not shown) via the network 1999. In various embodiments, the network 1999 may be a single network that may extend within a single building or other relatively limited area, a combination of connected networks that may extend a considerable distance, and/or may include the Internet. Thus, the network 1999 may be based on any of a variety (or combination) of communications technologies by which communications may be effected, including without limitation, wired technologies employing electrically and/or optically conductive cabling, and wireless technologies employing infrared, radio frequency or other forms of wireless transmission.

The diagnosis database 1130 may include a very large number of patient diagnosis records that each describe a medical history of a patient, including diagnoses. As familiar to those skilled in the art, each diagnosis may be indicated with an alphanumeric code that may be accompanied by an indication of when the diagnosis was made. The medication database 1230 may include a very large number of patient medication records that each describe a history of the filling of prescriptions for a patient. As familiar to those skilled in the art, each instance of filling a prescription for a patient may include an alphanumeric code indicating what medication was provided to the patient, and may be accompanied by an indication of when that medication was provided. As depicted, the diagnosis database 1130 may be stored within the one or more storage devices 1100, while the medication database 1230 may be stored within the one or more storage devices 1200. In some embodiments, the one or more storage devices 1100 may be maintained by one insurer, while the one or more storage devices 1200 may be maintained by an entirely different insurer as a result of a tendency in various markets for insurance coverage for prescription medications to be provided as a separate service from insurance coverage for other aspects of medical care, including diagnoses.

In various embodiments, each of the one or more node devices 1300 incorporates one or more of a processor component 1350, a storage 1360 and a network interface 1390 to couple each of the one or more node devices 1300 to the network 1999. The storage 1360 may store one or more of a control routine 1340, group datasets 1331, class datasets 1332, correlation data 1333, prediction data 1334, prediction results 1335 and results data 1336. The control routine 1340 may incorporate a sequence of instructions operative on the processor component 1350 to implement logic to perform various functions.

In various embodiments, the coordination device 1400 incorporates one or more of a processor component 1450, a storage 1460, manually-operable controls 1420, a display 1480 and a network interface 1490 to couple the coordinating device 1400 to the network 1999. The storage 1460 may store one or more of a control routine 1440, patient selection data 1430, diagnosis grouping data 1431, drug classification data 1432, model type data 1433, model sets 1434, model selection criteria 1435 and selected models 1436. The control routine 1440 may incorporate a sequence of instructions operative on the processor component 1450 to implement logic to perform various functions.

In executing the control routine 1340, the processor component 1350 of at least one of the one or more node devices 1300 may operate the network interface 1390 to receive commands to generate models correlating medication classes to diagnosis groups, to conduct tests on those models, and to use selected ones of the models to detect suspicious prescription filling patterns. In executing the control routine 1440, the processor component 1450 of the coordinating device 1400 may operate the network interface 1490 to transmit commands to the one or more node devices 1300 to perform those functions. More specifically, in executing the control routine 1440, the processor component 1450 may be caused to control the selections of patients for inclusion in datasets to be employed by the one or more node devices 1300 to derive and then conduct tests the models. The processor component 1450 may be caused to select, based on the results of the tests, a subset of the models to be used by the one or more node devices 1300 to detect suspicious prescription filling patterns. Subsequently, as the processor component 1350 of at least one of the one or more node devices 1300 is used to detect suspicious prescription filling patterns, the resulting indications of those suspicious patterns may be transmitted to the coordinating device 1400 and/or to the viewing device 1500.

Figure 12A:
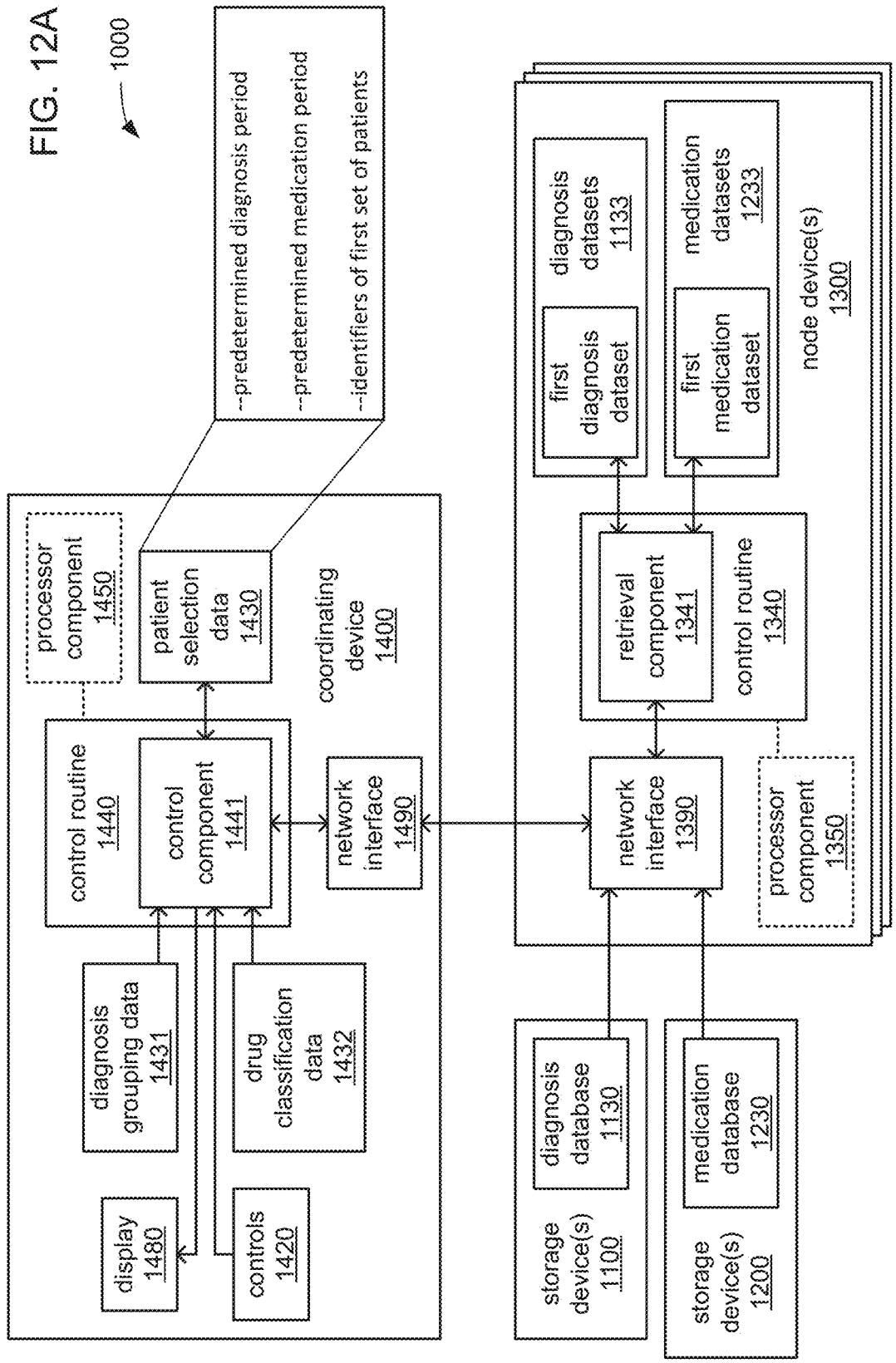
Figure 12B:
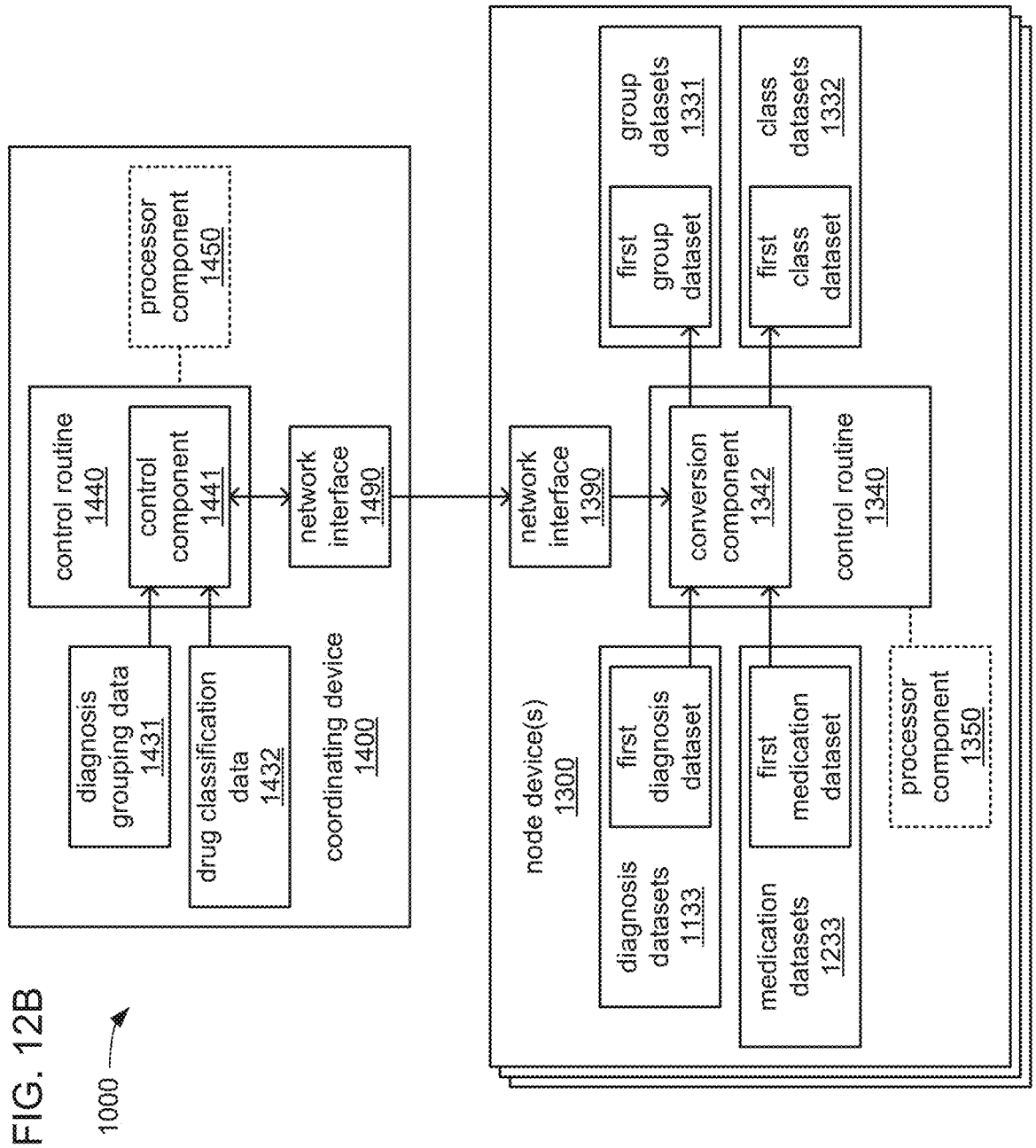
Figure 12E:
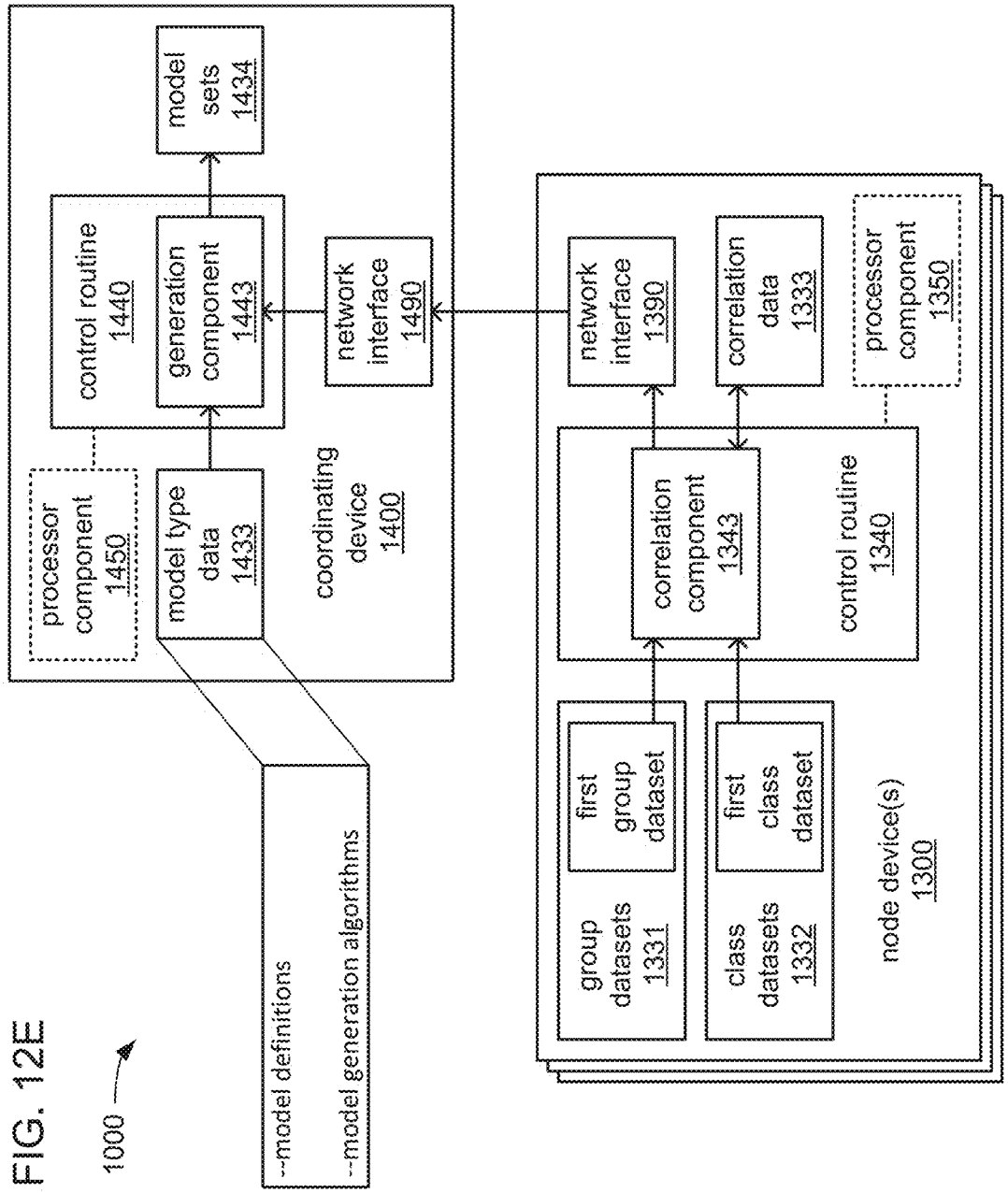

FIGS. 12A-E, together, illustrate an example of generating sets of models in embodiments of the fraud detection system 1000 of FIG. 11 in greater detail. More specifically, FIG. 12A depicts aspects of the retrieval and filtering of diagnosis and medication histories of a randomly selected first set of patients. FIGS. 12B, 12C and 12D, together, depict aspects of converting diagnoses to diagnosis groups and medications to medication classes. FIG. 12E depicts aspects of the generation of sets of models based on multiple model definitions and correlations identified in those diagnosis and medication histories.

As recognizable to those skilled in the art, the control routines 1340 and 1440, including the components of which each is composed, are selected to be operative on whatever type of processor or processors that are selected to implement applicable ones of the processor components 1350 and 1450. In various embodiments, each of these routines may include one or more of an operating system, device drivers and/or application-level routines (e.g., so-called "software suites" provided on disc media, "applets" obtained from a remote server, etc.). Where an operating system is included, the operating system may be any of a variety of available operating systems appropriate for the processor components 1350 and/or 1450. Where one or more device drivers are included, those device drivers may provide support for any of a variety of other components, whether hardware or software components, of the coordinating device 1400, and/or the one or more node devices 1300.

Turning to FIG. 12A, as depicted, the control routine 1440 may include a control component 1441 to trigger and/or control the generation of sets of models. In some embodiments, the control component 1441 may operate the controls 1420 and/or the display 1480 to provide a user interface enabling an operator of the coordinating device 1400 to provide a command to the coordinating device 1400 to trigger the generation, testing, selection and/or use of models in identifying suspicious prescription filling patterns. In other embodiments, the control component 1441 may monitor the passage of time and trigger such generation, testing, selection and/or use of models on a recurring basis in response to the elapsing of a recurring interval of time (e.g., triggering daily, weekly, monthly, etc.).

In still other embodiments, the control component 1441 may monitor the status of the diagnosis grouping data 1431 and/or the drug classification data 1432 for indications of changes made thereto. Such changes may be made over time by an operator of the coordinating device 1400 via the user interface provided by the display 1480 and/or the controls 1420. Alternatively or additionally, updated versions of the diagnosis grouping data 1431 and/or the drug classification data 1432 may occasionally be received via the network 1999 and/or other mechanisms from another device (not shown). In such embodiments, the control component 1441 may trigger such generation, testing selection and/or use of models in response to a degree of change made in one or both of the diagnosis grouping data 1431 and the drug classification data 1432 that exceeds a predetermined threshold of change.

The diagnosis grouping data 1431 may indicate the manner in which numerous specific diagnoses may be categorized into diagnosis groups devised by various experts in the medical field. By way of example, the diagnosis grouping data 1431 may be based on diagnosis groupings developed by the National Center for Health Statistics (NCHS) of the Centers for Disease Control (CDC) of Atlanta, Ga., and may be based on which system of the human body is primarily involved in each diagnosis (e.g., the gastro-intestinal system, the endocrine system, etc.). The drug classification data 1432 may indicate the manner in which numerous medications are categorized into medication classes that may also be devised by various experts in the medical field. By way of example, the drug classification data 1432 may be based on the medication classifications of the Anatomical Therapeutic Chemical Classification System (ATC) developed by the World Health Organization (WHO) of Geneva, Switzerland, and may be based on the type of physiological change made by each medication and/or on the mechanism by which each medication affects the human body.

As also depicted in FIG. 12A, the control routine 1340 may include a retrieval component 1341 to retrieve the diagnosis and medication histories and to limit the patients included in the first set of patients to those with diagnosis and medication histories that fit specified criteria. In some embodiments the triggering of at least the generation of models by the control component 1441 of the control routine 1440 may entail the control component 1441 operating the network interface 1490 of the coordinating device 1400 to transmit a command to the one or more node devices 1300 to begin the retrieval of diagnosis and medication histories for the first set of patients. The command may be accompanied by indications of the criteria that the patients of the first set of patients must meet, which the control component 1441 may retrieve from the patient selection data 1430. The command may also specify a minimum quantity of patients to be included in the first set of patients.

Such triggering of at least the generation of models may also entail the retrieval component 1341 in each of the one or more node devices 1300 operating the network interface 1390 thereof to receive the command transmitted by the control component 1441, along with the criteria specified in the command that each of the patients in the first set of patients must meet. In response to the receipt of such a command, the retrieval component 1341 may operate the network interface 1390 to retrieve multiple patient diagnosis records from the diagnosis database 1130 stored by the one or more storage devices 1100, and to retrieve multiple patient medication records for the same patients from the medication database 1230. In some embodiments, the retrieval component 1341 may first retrieve an index of patient identifiers from one or both of the databases 1130 and 1230, and may randomly select patients for which to retrieve such records from that index.

As the retrieval component 1341 retrieves those records, it may filter out ones of the records associated with patients that do not meet the specified criteria. The retrieval component 1341 may store the retrieved patient diagnosis records as at least a portion of a first diagnosis dataset of the diagnosis datasets 1133, and may store the retrieved patient medication records as at least a portion of a first medication dataset of the medication datasets 1233. However, in so doing, the retrieval component 1341 may limit the records so stored to those associated with patients who meet the specified criteria.

More specifically, and as depicted, the patient selection data 1430 may specify a predetermined diagnosis period extending into the past from the present day during which each patient in the first set of patients must have received at least one diagnosis of at least one medical condition (as opposed to having been found to have no medical conditions). The patient selection data 1430 may also specify a predetermined medication period extending into the past from the present day during which each patient in the first set of patients must have received at least one medication on at least one occasion. Again, as it may be expected that the provision of medication under prescription arises from a diagnosis having been made, the predetermined diagnosis period may reach further back in time than the predetermined medication period (e.g., a predetermined diagnosis period of two years into the past versus a predetermined medication period of one year into the past).

Thus, the retrieval component 1341 may not include patients in the first set of patients those who have not received at least one diagnosis of at least one medical condition during the predetermined diagnosis period or who have not been provided with at least one medication on at least one occasion during the predetermined medication period. In so doing, the retrieval component 1341 may ensure that the first diagnosis dataset and the first medication dataset include patient diagnosis records and patient medication records, respectively, that are associated only with patients that meet such specified criteria. In embodiments in which the retrieval component 1341 within each of multiple ones of the one or more node devices 1300 retrieve records from the databases 1130 and 1230, and filters out patients who do not meet the specified criteria, the control component 1441 may receive from each of the one or more node devices 1300 indications of which patients have been included in the first set of patients, and may store those indications in the patient selection data 1430 as part of coordinating those operations.

Turning to FIG. 12B, as depicted, the control routine 1340 may include a conversion component 1342 to convert the indications of specific diagnoses to diagnosis groups and indications of specific medications to medication classes. As familiar to those skilled in the art, there can be many slight variations in diagnoses to specify details such as severity of a medical condition, stage of progression thereof, the onset of differing complications, etc. Correspondingly, there can be many variations of a particular medication to specify manufacturer, country of origin, type of delivery mechanism, dosage size, etc. Further, it is common practice in the medical field to specify each of these variations of diagnoses and medications with a unique alphanumeric code. Unfortunately, medical professionals can, on occasion, become confused on the subject of what specific code to use for a particular slight variation of diagnosis or medication. The conversion of such specific indications of diagnoses into corresponding diagnosis groups and such specific indications of medications into corresponding medication classes may, therefore, be deemed desirable to reduce the complexity of the models by basing those models on the more limited sets of diagnosis groups and medication classes, then on the far larger sets of codes associated with individual diagnoses and medications. Thus, the conversion component 1342 may operate the network interface 1390 to receive the diagnosis grouping data 1431 and/or the drug classification data 1432 as transmitted from the coordinating device 1400 by the control component 1441.

As depicted in FIG. 12C, the conversion component 1342 may employ the diagnosis grouping data 1431 to convert each indication in the first diagnosis dataset of a specific diagnosis made during the predetermined diagnosis period into an indication in a first group dataset of a diagnosis belonging to a particular diagnosis group. Stated differently, for each patient diagnosis record within the first diagnosis dataset, a corresponding diagnosis group record may be generated in the first group dataset. Also, for each diagnosis indicated in the each patient diagnosis record as having been made during the predetermined diagnosis period, a corresponding indication of a diagnosis group to which that diagnosis belongs may be included in the corresponding diagnosis group record.

Correspondingly, as depicted in FIG. 12D, the conversion component 1342 may employ the drug classification data 1432 to convert each indication in the first medication dataset of the provision of a specific medication during the predetermined medication period into an indication in a first class dataset of the provision of a medication belonging to a particular medication class. Stated differently, for each patient medication record within the first diagnosis dataset, a corresponding medication class record may be generated in the first class dataset. Also, for each medication indicated in the each patient medication record as having been provided during the predetermined medication period, a corresponding indication of a medication class to which that medication belongs may be included in the corresponding medication class record.

Turning to FIG. 12E, as depicted, the control routine 1340 may include a correlation component 1343 to analyze each diagnosis group record within the first group dataset and the medication class record that corresponds by patient within the first class dataset to identify the correlations between diagnosis groups and medication classes therebetween. The correlation component 1343 may store indications of the identified correlations as the correlation data 1333, and operate the network interface 1390 to transmit the correlation data 1333 to the coordinating device 1400.

As also depicted in FIG. 12E, the control routine 1440 may include a generation component 1443 to generate a set of models based on the correlations indicated in the correlation data. More specifically, the generation component 1443 may operate the network interface 1490 to receive the correlation data 1333 from each of the one or more node devices 1300 in which an instance of the correlation component 1343 provides an instance of the correlation data 1333. For each diagnosis group to which at least one medication class is correlated in at least one instance of the correlation data 1333, the generation component may generate a model set 1434 that includes multiple models. All of the models within a model set 1434 are based on all of the correlations of its associated diagnosis group to any medication class, regardless of whether there is only one such correlation across multiple instances of correlation data 1333, or many. However, each of the models within a model set 1434 may be a different type of model generated by the generation component using a different generation algorithm (e.g., a decision tree model, a regression model, a neural network model, etc.). The generation component 1443 may retrieve definitions for each of the different types of models and the algorithms to generate each type from the model type data 1433.

Figure 13A:
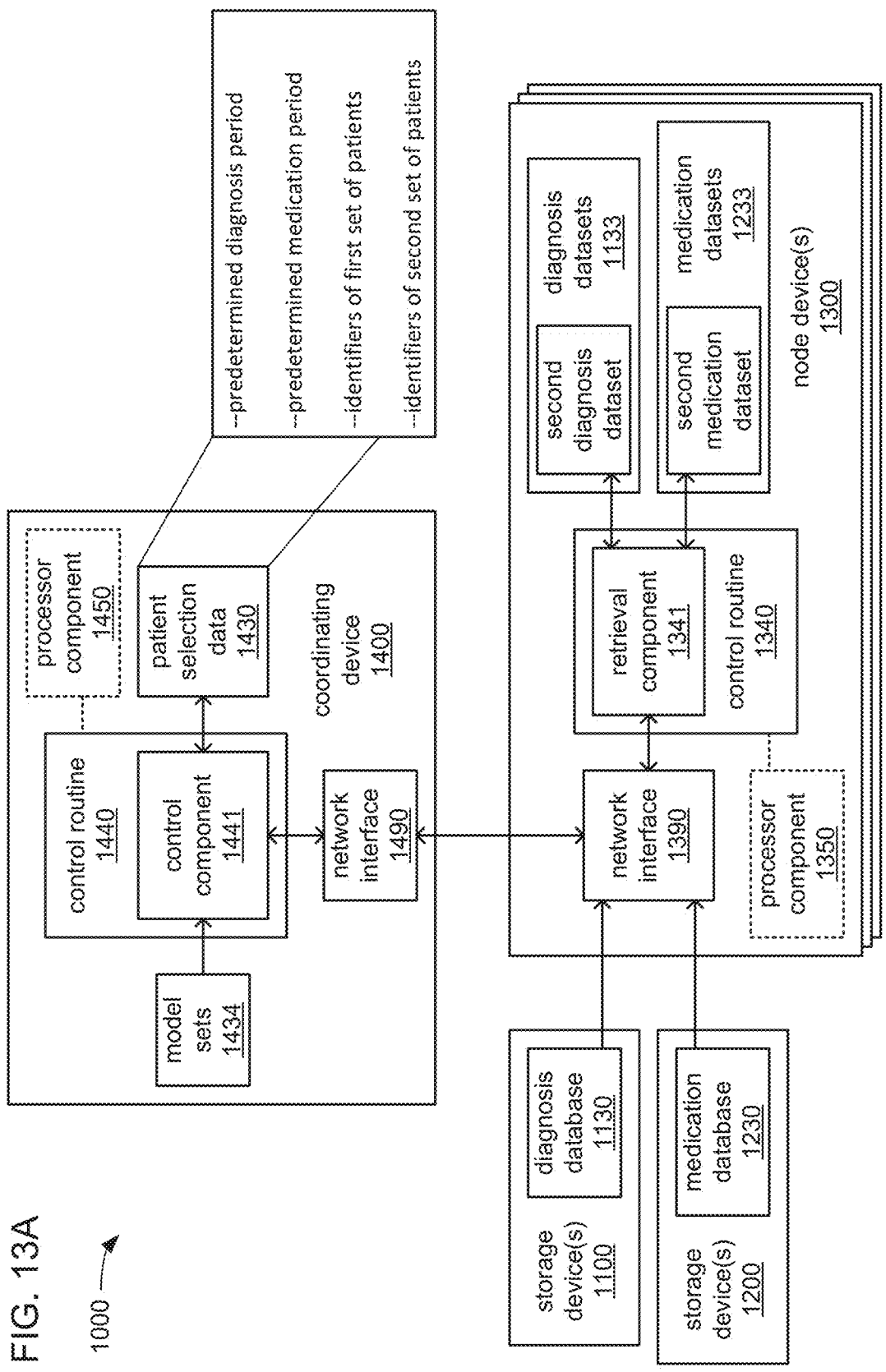
FIGS. 13A, 13B and 13C, together, illustrate an example of selecting a model from each set of models of FIGS. 12A-E to use in detecting suspicious prescription filling behavior.
Figure 13B:
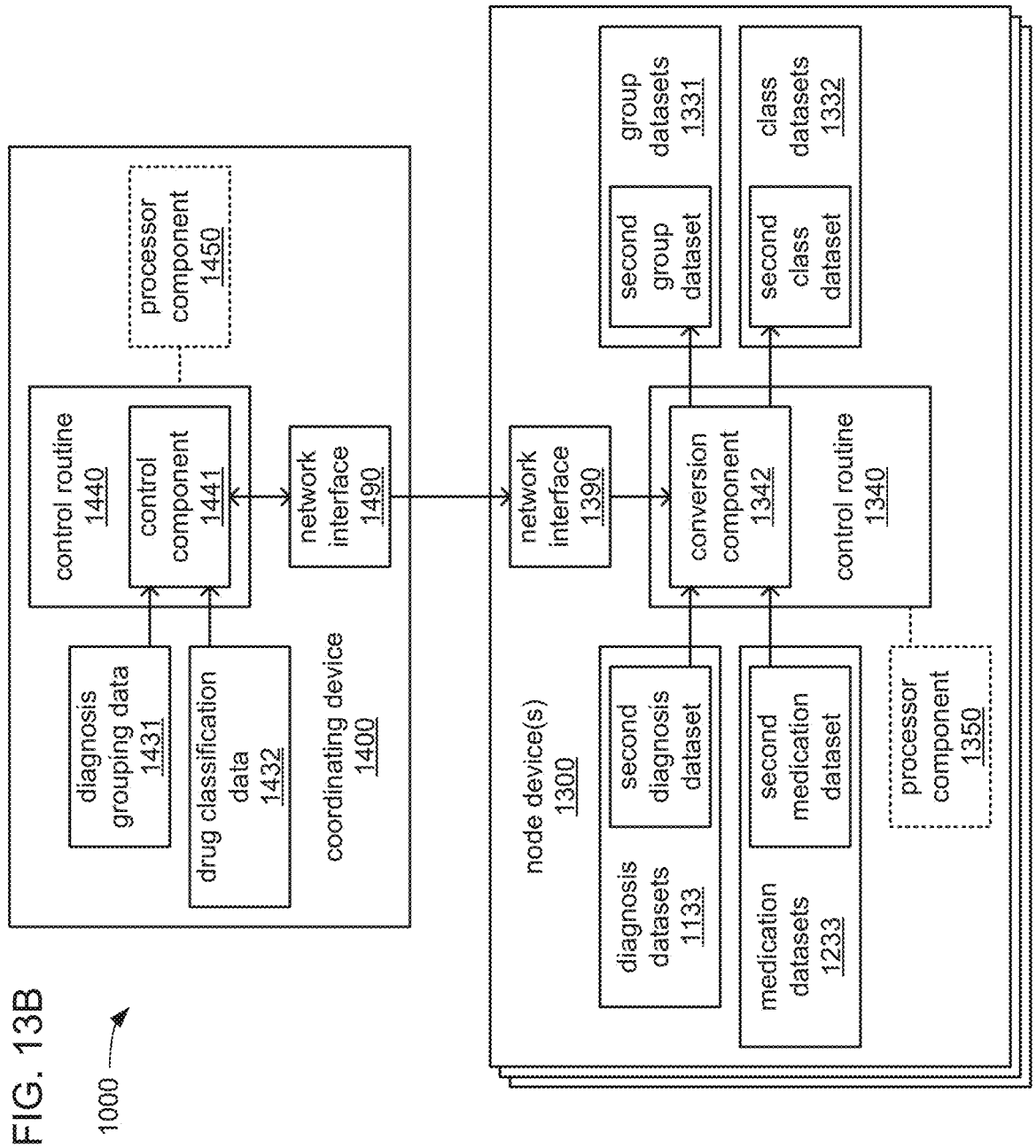
Figure 13C:
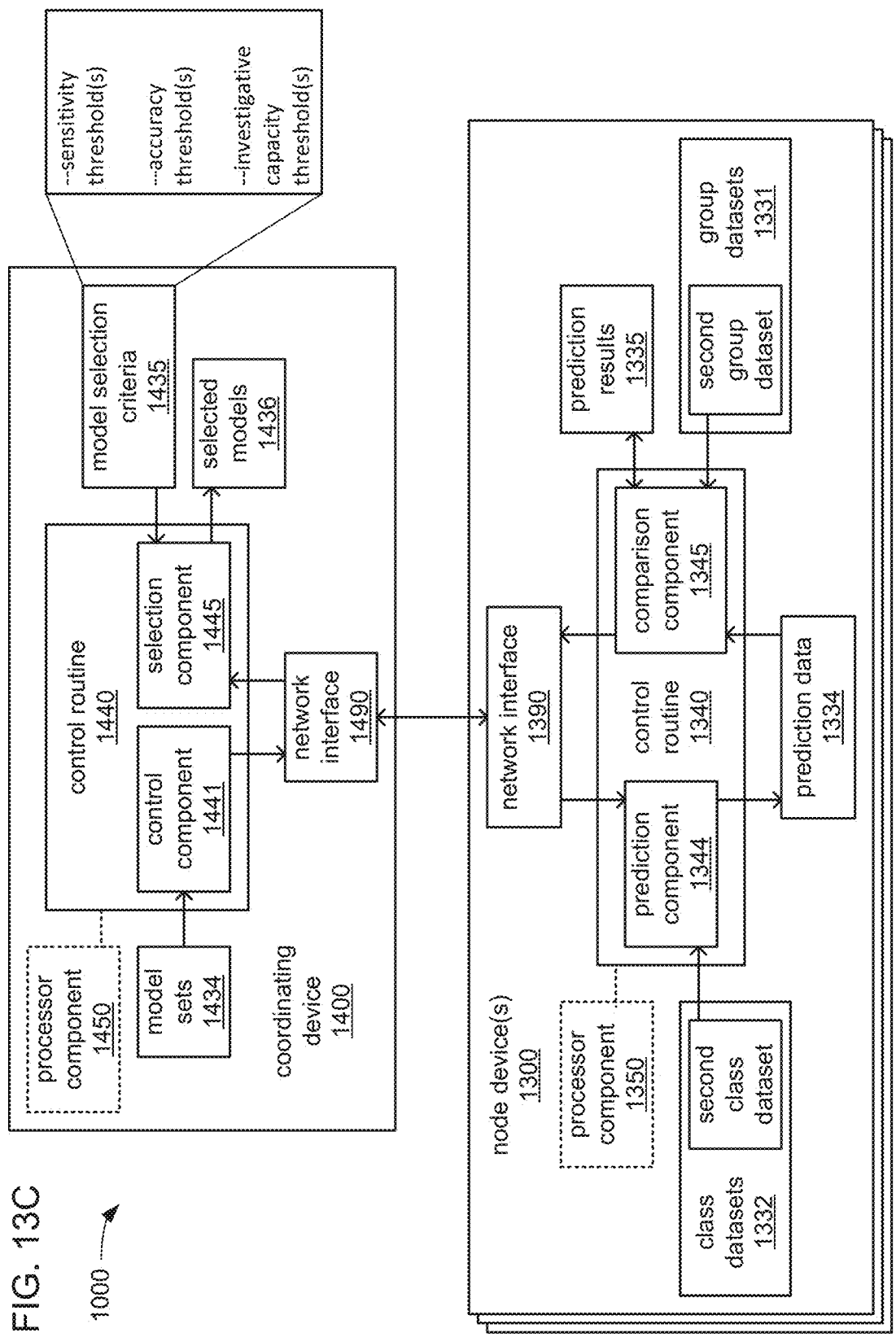

FIGS. 13A-C, together, illustrate an example of testing and selecting models from each set of models in embodiments of the fraud detection system 1000 of FIG. 11 in greater detail. More specifically, FIG. 13A depicts aspects of the retrieval and filtering of diagnosis and medication histories of a randomly selected second set of patients. FIG. 13B depicts aspects of converting diagnoses to diagnosis groups and medications to medication classes. FIG. 13C depicts aspects of the selection of a model from each set of models.

Turning to FIG. 13A, as depicted, the control routine 1440 may trigger the testing of the models within each model set 1434 associated with a diagnosis group by operating the network interface 1490 of the coordinating device 1400 to transmit a command to the one or more node devices 1300 to begin the retrieval of diagnosis and medication histories for a second set of patients. As was the case in the retrieval of diagnosis and medication histories for the first set of patients, this command may be accompanied by indications of the criteria that the patients of the second set of patients must meet, which the control component 1441 may retrieve from the patient selection data 1430. The command may also specify a minimum quantity of patients to be included in the second set of patients. In some embodiments, the requirements to be met by the second set of patients and/or the quantity of patients may be the same as those for the first set of patients.

Again, the retrieval component 1341 in each of the one or more node devices 1300 may operate the network interface 1390 thereof to receive the command transmitted by the control component 1441, along with the criteria specified in the command that each of the patients in the second set of patients must meet. In response to the receipt of such a command, the retrieval component 1341 may again operate the network interface 1390 to retrieve multiple patient diagnosis records from the diagnosis database 1130 stored by the one or more storage devices 1100, and to retrieve multiple patient medication records for the same patients from the medication database 1230.

Again, as the retrieval component 1341 retrieves those records, it may filter out ones of the records associated with patients that do not meet the specified criteria, and may store the retrieved patient diagnosis records as at least a portion of a second diagnosis dataset of the diagnosis datasets 1133, and may store the retrieved patient medication records as at least a portion of a second medication dataset of the medication datasets 1233. Additionally, the control component 1441 may retrieve indications of the identifiers of the patients that were included in the first set of patients from the patient selection data 1430, and may operate the network interface 1490 to distribute those indications among the one or more node devices 1300. The retrieval component 1341 within each of the one or more node devices 1300 involved in retrieving records for the second set of patients may refer to the indications of identifiers of the first set of patients received from the control component 1441 to avoid including any patients of the first set of patients in the second set of patients. Still further, the control component 1441 may receive from each of the one or more node devices 1300 indications of which patients have been included in the second set of patients, and may store those indications in the patient selection data 1430 as part of coordinating the operations performed by the one or more node devices 1300.

Turning to FIG. 13B, as depicted, the conversion component 1342 may again be employed to convert indications of specific diagnoses to diagnosis groups and indications of specific medications to medication classes. In a manner similar to what was done with records associated with the first set of patients, the conversion component 1342 may employ the diagnosis grouping data 1431 to convert each indication in the second diagnosis dataset of a specific diagnosis made during the predetermined diagnosis period into an indication in a second group dataset of a diagnosis belonging to a particular diagnosis group. Stated differently, for each patient diagnosis record within the second diagnosis dataset, a corresponding diagnosis group record may be generated in the second group dataset. Correspondingly, the conversion component 1342 may employ the drug classification data 1432 to convert each indication in the second medication dataset of the provision of a specific medication during the predetermined medication period into an indication in a second class dataset of the provision of a medication belonging to a particular medication class. Stated differently, for each patient medication record within the second diagnosis dataset, a corresponding medication class record may be generated in the second class dataset.

Turning to FIG. 13C, as depicted, the control routine 1340 may include a prediction component 1344 to employ the earlier generated model sets 1434 to generate predictions of diagnosis groups from indications of medication classes. More specifically, for each medication class record in the second class dataset, the prediction component may employ the indications of which medication class(es) are associated with medications that were provided to predict what diagnosis groups are associated with diagnosis(es) that lead to the provision of those medications. In so doing, the prediction component may employ all of the models in all of the earlier derived sets of models 1434. As previously discussed, each model set 1434 is associated with a different diagnosis group such that each model set 1434 is made up of models that correlate medications belong to one or more medication class to the diagnosis group associated with that model set 1434. The predictions made by each of the models of each model set 1434 may be stored by the prediction component 1344 as the prediction data 1334.

As also depicted in FIG. 13C, the control routine 1340 may also include a comparison component 1345 to compare the predictions of diagnosis groups associated with the second set of patients to the diagnosis groups indicated in the diagnosis histories of the second set of patients as having actually been made. More specifically, for each diagnosis group record in the second group dataset, the comparison component 1345 may compare each prediction of what diagnosis groups would be indicated therein by each model of each model set 1434 to what diagnosis groups are actually indicated therein. As the comparison component 1345 progresses through each of those diagnosis group records, the comparison component 1345 may accrue scores for each of the models of each of the model sets 1434 of true positives in which a correct prediction of the inclusion of a diagnosis group was made and of false positives in which an incorrect prediction of the inclusion of a diagnosis group was made. The comparison component 1345 may store those accrued tallies of false and true positives for each model of each model set 1434 as the prediction results 1335, which the comparison component 1345 may operate the network interface 1390 to transmit to the coordinating device 1400.

As further depicted in FIG. 13C, the control routine 1440 may include a selection component 1445 to select one model within each model set 1434 for use in detecting suspicious prescription filling patterns based at least on the tallies of false positives and true positives for each model of each model set 1434. More specifically, the selection component 1445 may operate the network interface 1490 to receive each instance of the predictions results 1335 transmitted to the coordinating device 1400 by each of the one or more node devices 1300 in which models were tested. From the tallies of false positives and true positives for each model, the selection component 1445 may determine a degree of accuracy of prediction and/or a degree of sensitivity to suspicious prescription filling patterns of that model. For each model set 1434, the selection component 1445 may then select one model to be used in detecting suspicious prescription filling patterns based on the degrees of accuracy and/or sensitivity of each of the models within that model set 1434. In so doing, the selection component 1445 may retrieve indications of one or more thresholds for accuracy and/or sensitivity from the model selection criteria 1435. By way of example, the model selection criteria 1435 may specify a threshold of sensitivity as a percentage of the predictions that are determined to be true positives, and/or may specify a threshold of accuracy as a combination of the percentage of predictions that are determined to be true positives and a percentage of correlations that are determined to actually be present that were not missed by the predictions. It should be noted that still other measures may be specified and/or used in selecting models.

The selection component 1445 may also base its selection of one model within each model set 1434 on indications of one or more thresholds for available capacity to investigate pharmacies and/or patients associated with detected suspicious prescription filling patterns. By way of example, the prescription fraud detection system 1000 may be operated by and/or on behalf of an investigative agency of a government that is constrained by a budget such that there are limits on the number of investigations into possible prescription fraud that can be conducted at any one time. The model selection criteria 1435 retrieved and employed by the selection component 1445 may include a threshold of a maximum number of suspicious prescription filling patterns that should be detected through use of a model on each occasion that the model is used. Following the selection of one model for each model set 1434, the selection component 1445 may store indications of the models that were so selected as the selected models 1436.

Alternatively or additionally, there may be instances in which the selection component 1445 may refrain from selecting any of the models within one or more of the model sets 1434. By way of example, if none of the models within a model set 1434 meet one or more thresholds for accuracy, sensitivity and/or another measure of degree of effectiveness, then the selection component 1445 may not select any of the models within that model set 1434. Although this may result in no predictions and/or analysis of correlations involving the diagnosis group associated with that model set 1434, leaving out that associated diagnosis group may be deemed preferable to selecting and employing a model of that model set 1434 that does not meet one or more of such thresholds. This preference may be based on a desire to avoid the use of limited investigative resources to investigate prescription filling patterns that are incorrectly indicated as being suspicious as a result of using such a model. Thus, the selected models 1436 may not include any model from one or more of the model sets 1434 where no model was selected.

Figure 14A:
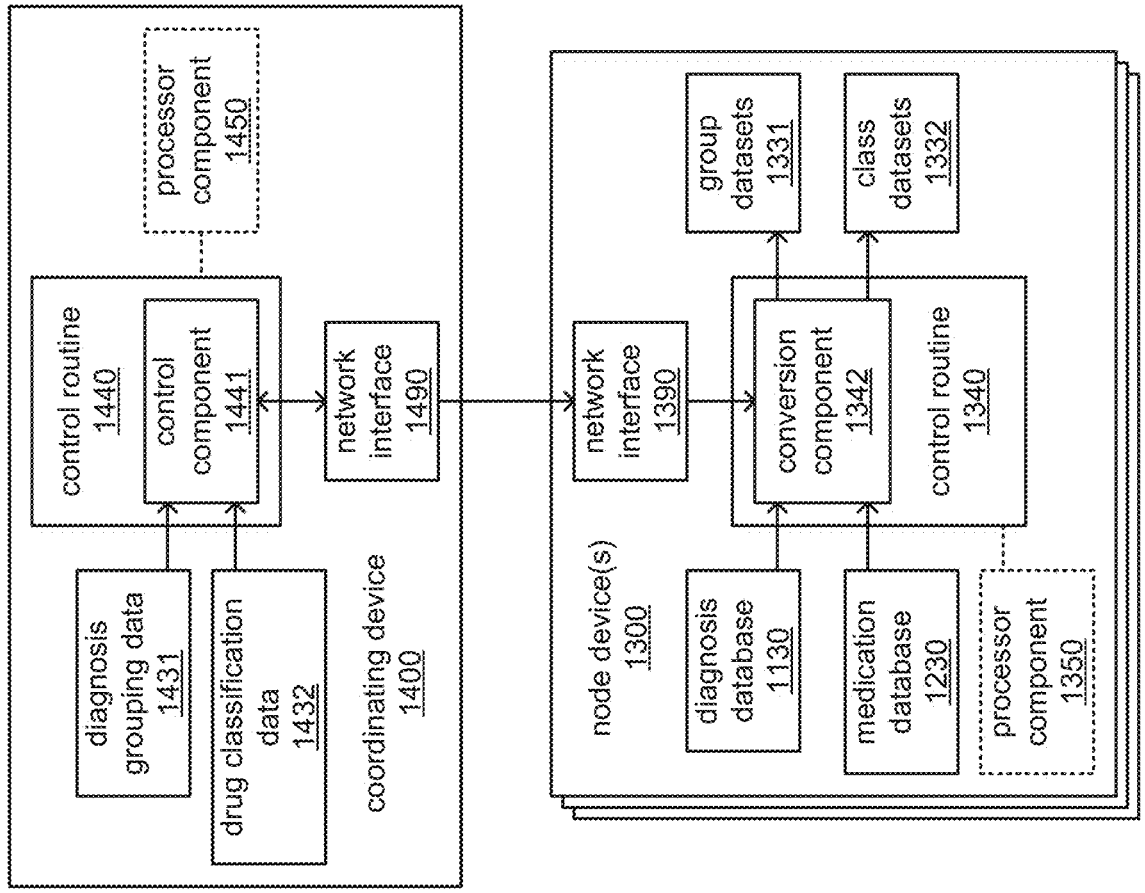
FIGS. 14A and 14B, together, illustrate an example of using the selected models of FIGS. 13A-C to detect suspicious prescription filling behavior.
Figure 14B:
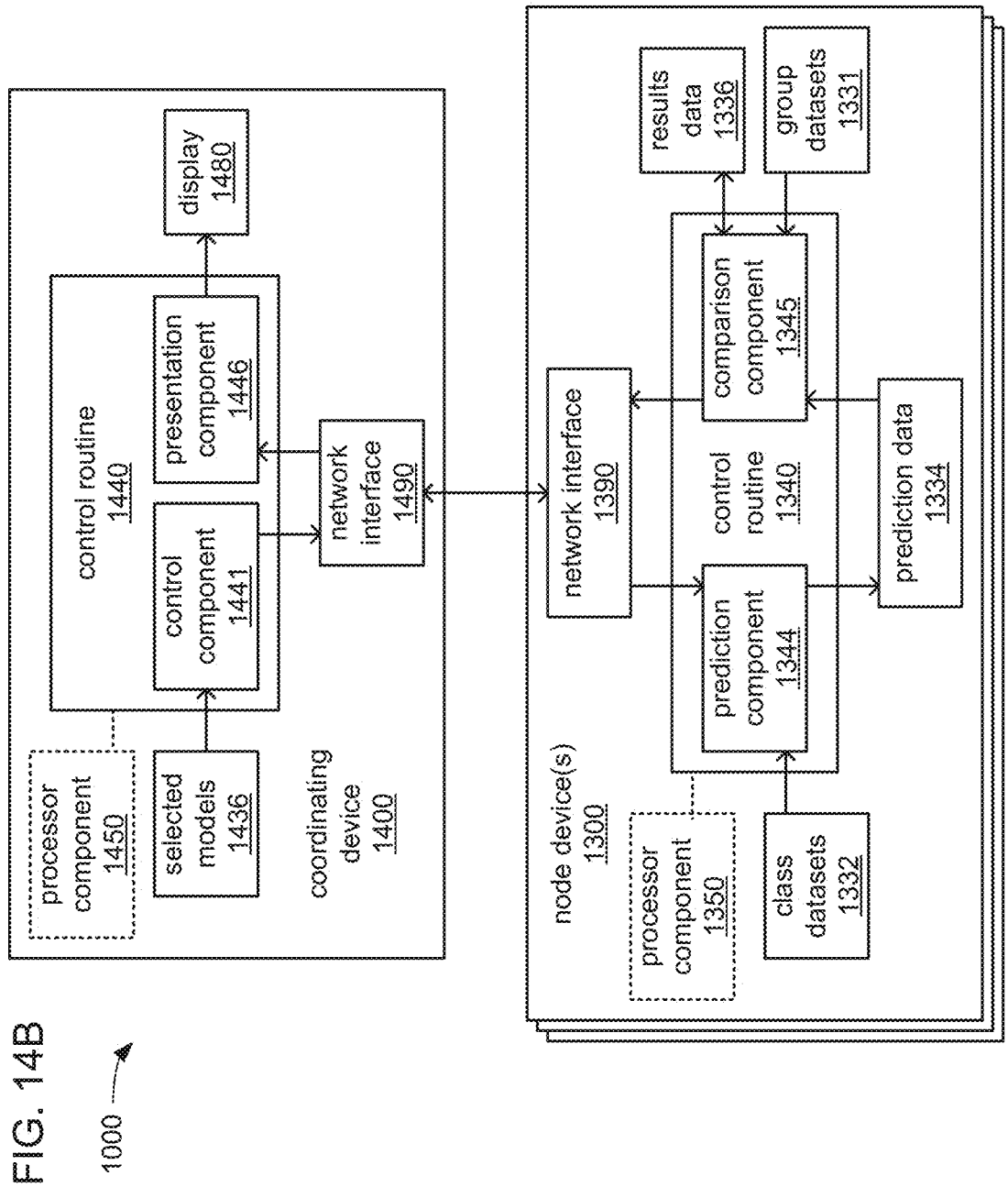

FIGS. 14A-B, together, illustrate an example of using the selected models 1436 to detect suspicious prescription filling patterns in embodiments of the fraud detection system 1000 of FIG. 11 in greater detail. FIG. 14A depicts aspects of converting diagnoses to diagnosis groups and medications to medication classes for still more patients within the diagnosis database 1130 and the medication database 1230. FIG. 14B depicts aspects of the use of the selected models 1436.

Turning to FIG. 14A, instead of retrieving diagnosis and medication records of relatively limited sets of patients for the generation, testing and selection of models, as was depicted and discussed in relation to FIGS. 12A and 13A, the diagnosis and medication records of at least a relatively large portion of the patients who are included in both the diagnosis database 1130 and the medication database 1230 may be retrieved as inputs for the conversion component 1342. The conversion component 1342 may again be employed to convert indications of specific diagnoses in the patient diagnosis records of the diagnosis database 1130 to indications of diagnosis groups in the diagnosis group records of one or more group datasets 1331 using the diagnosis grouping data 1431, and to convert indications of specific medications in the patient medication records of the medication database 1230 to indications of medication classes in the medication class records of one or more class datasets 1332 using the drug classification data 1432.

Turning to FIG. 14B, the prediction component 1344 may again generate predictions of diagnosis groups from indications of medication classes. More specifically, for each medication class record in the one or more class datasets 1332 generated in FIG. 14A, the prediction component 1344 may employ the selected models 1436 provided to the prediction component 1344 by the control component 1441 to predict what diagnosis groups are associated with diagnosis(es) that lead to the provision of those medications. The prediction component 1344 may again store its predictions as the prediction data 1334.

The comparison component 1345 may then again compare the predictions of diagnosis groups made by the prediction component 1344 from each medication class record of the one or more class datasets 1332 to the diagnosis groups indicated as having actually been made in corresponding ones of the diagnosis records of the one or more group datasets 1331. As the comparison component 1345 progresses through each of the diagnosis group records of the one or more group datasets 1331, the comparison component 1345 may accrue scores for each pharmacy indicating the number of times a prediction of a diagnosis group was made that was not matched by an indication of an actual diagnosis of that diagnosis group having actually been made. The comparison component 1345 may store indications of those accrued scores for each pharmacy found in the one or more group datasets 1331 as part of the results data 1336. Generally, pharmacies with larger accrued scores than the median or mean score, or that have scores in a higher percentile than the others may be deemed to be demonstrating a suspicious prescription filling pattern. Alternatively or additionally, as the comparison component 1345 progresses through each of the diagnosis group records of the one or more group datasets 1331, the comparison component 1345 may store indications of degrees by which predictions of diagnosis groups were not matched by indications of diagnosis groups for which there were indications of actual diagnoses for each patient found in the one or more group datasets 1331. Generally, patients with greater degrees of such a mismatch may be deemed to be demonstrating a suspicious prescription filling pattern.

As also depicted in FIG. 14B, the control routine 1440 may include a presentation component 1446 to operate the display 1480 and/or another output device of the coordinating device 1400 to provide an indication of the results of the use of the selected models 1436 to detect suspicious prescription filling patterns. The presentation component 1446 may operate the network interface 1490 to receive each instance of the results data 1336 from each of the one or more node devices 1300 that performed the work of using the selected models 1436 to detect suspicious prescription filling patterns. Where there are multiple instances of the results data 1336, the presentation component 1446 may combine the accrued scores for pharmacies among those multiple instances to derive the total accrued scores to present on the display 1480 and/or otherwise output through another output device. Among such other output devices may be the network interface where the presentation component 1446 may transmit indications of the combined scores for patients and/or the total accrued scores for pharmacies to another device for presentation, such as the viewing device 1500, which may present those indications on the display 1580.

Returning to FIG. 11, the processor component 1350 of each of the one or more node devices 1300 may be selected to efficiently perform the conversions of indications of specific diagnoses and medication to diagnosis groups and medication classes, respectively. Alternatively or additionally, the processor component 1350 of each of the one or more node devices 1300 may be selected to efficiently employ each of multiple models at least partly in parallel to predict indications of diagnosis groups in diagnosis group records based on indications of medication classes in medication class records. By way of example, the processor component 1350 may incorporate a single-instruction multiple-data (SIMD) architecture, may incorporate multiple processing pipelines, and/or may incorporate the ability to support multiple simultaneous threads of execution per processing pipeline. This may enable conversions of multiple indications within a record and/or across multiple records to be performed at least partly in parallel, and/or may enable the use of multiple models of a single model set 1434 and/or multiple models of the selected models 1436 at least partly simultaneously. Each of these node devices 1300 may be any of a variety of types of device that incorporates at least the processing resources to enable efficient performance of such conversions at least partly in parallel. Each of these node devices may be any of a variety of types of device that incorporates at least the processing resources to enable efficient testing and/or use of multiple models at least partly in parallel.

In various embodiments, each of the processor components 1350 and 1450 may include any of a wide variety of commercially available processors. Further, one or more of these processor components may include multiple processors, a multi-threaded processor, a multi-core processor (whether the multiple cores coexist on the same or separate dies), and/or a multi-processor architecture of some other variety by which multiple physically separate processors are linked.

However, in a specific embodiment, the processor component 1350 of one or more of the node devices 1300 may incorporate multi-threaded capabilities that may be implemented with multiple processing cores such that one or more additional threads to separately process one or more patient diagnosis records, patient medication records, diagnosis group records and/or medication class records may be distributed among multiple processing cores.

In various embodiments, each of the storages 1360 and 1460 may be based on any of a wide variety of information storage technologies, including volatile technologies requiring the uninterrupted provision of electric power, and/or including technologies entailing the use of machine-readable storage media that may or may not be removable. Thus, each of these storages may include any of a wide variety of types (or combination of types) of storage device, including without limitation, read-only memory (ROM), random-access memory (RAM), dynamic RAM (DRAM), Double-Data-Rate DRAM (DDR-DRAM), synchronous DRAM (SDRAM), static RAM (SRAM), programmable ROM (PROM), erasable programmable ROM (EPROM), electrically erasable programmable ROM (EEPROM), flash memory, polymer memory (e.g., ferroelectric polymer memory), ovonic memory, phase change or ferroelectric memory, silicon-oxide-nitride-oxide-silicon (SONOS) memory, magnetic or optical cards, one or more individual ferromagnetic disk drives, or a plurality of storage devices organized into one or more arrays (e.g., multiple ferromagnetic disk drives organized into a Redundant Array of Independent Disks array, or RAID array). It should be noted that although each of these storages is depicted as a single block, one or more of these may include multiple storage devices that may be based on differing storage technologies. Thus, for example, one or more of each of these depicted storages may represent a combination of an optical drive or flash memory card reader by which programs and/or data may be stored and conveyed on some form of machine-readable storage media, a ferromagnetic disk drive to store programs and/or data locally for a relatively extended period, and one or more volatile solid state memory devices enabling relatively quick access to programs and/or data (e.g., SRAM or DRAM). It should also be noted that each of these storages may be made up of multiple storage components based on identical storage technology, but which may be maintained separately as a result of specialization in use (e.g., some DRAM devices employed as a main storage while other DRAM devices employed as a distinct frame buffer of a graphics controller).

However, in a specific embodiment, the storage 1360 of the one or more node devices 1300 that stores one or more of the datasets 1133, 1233, 1331 and 1332 may be implemented with a redundant array of independent discs (RAID) of a RAID level selected to provide fault tolerance to prevent loss of one or more of these datasets and/or to provide increased speed in accessing one or more of these datasets.

In various embodiments, the network interfaces 1390 and 1490 may employ any of a wide variety of communications technologies enabling these devices to be coupled to other devices as has been described. Each of these interfaces includes circuitry providing at least some of the requisite functionality to enable such coupling. However, each of these interfaces may also be at least partially implemented with sequences of instructions executed by corresponding ones of the processor components (e.g., to implement a protocol stack or other features). Where electrically and/or optically conductive cabling is employed, these interfaces may employ timings and/or protocols conforming to any of a variety of industry standards, including without limitation, RS-232C, RS-422, USB, Ethernet (IEEE-802.3) or IEEE-1394. Where the use of wireless transmissions is entailed, these interfaces may employ timings and/or protocols conforming to any of a variety of industry standards, including without limitation, IEEE 802.11a, 802.11b, 802.11g, 802.16, 802.20 (commonly referred to as "Mobile Broadband Wireless Access"); Bluetooth; ZigBee; or a cellular radiotelephone service such as GSM with General Packet Radio Service (GSM/GPRS), CDMA/1xRTT, Enhanced Data Rates for Global Evolution (EDGE), Evolution Data Only/Optimized (EV-DO), Evolution For Data and Voice (EV-DV), High Speed Downlink Packet Access (HSDPA), High Speed Uplink Packet Access (HSUPA), 4G LTE, etc.

However, in a specific embodiment, the network interface 1390 of the one or more node devices 1300 that stores one or more of the datasets 1133, 1233, 1331 and 1332 may be implemented with multiple copper-based or fiber-optic based network interface ports to provide redundant and/or parallel pathways in exchanging one or more of these datasets.

FIG. 15 illustrates an example embodiment of a logic flow 2100. The logic flow 2100 may be representative of some or all of the operations executed by one or more embodiments described herein. More specifically, the logic flow 2100 may illustrate operations performed by the processor components 1350 and/or 1450 in executing the control routines 1340 and/or 1440, and/or performed by other component(s) of at least the coordinating device 1400, and/or the one or more node devices 1300.

At 2110, a processor component of a coordinating device (e.g., the processor component 1450 of the coordinating device 1400) may check whether a diagnosis grouping data (e.g., the diagnosis grouping data 1431) has been changed to a degree that meets a threshold of change. If not, then the processor component may check at 2112 whether a drug classification data (e.g., the drug classification data 1432) has been changed to a degree that meets a threshold of change. If not, then the processor component may check at 2114 whether an interval of time predetermined to be the maximum interval of time between instances of regenerating models for detecting suspicious prescription filling patterns has elapsed. If not, then the processor component may repeat the check made at 2110.

However, if the threshold of change of the diagnosis grouping data has been met at 2110, if the threshold of change of the drug classification data has been met at 2112, or if the maximum interval of time between regenerations of the models has elapsed at 2114, then the processor component may trigger at least the regeneration of the models at 2120. More specifically, at 2120, the processor component of the coordinating device may command at least one processor component of at least one node device (e.g., the processor component 1350 of at least one node device 1300) to randomly select a first set of patients with at least one diagnosis of having a medical condition made during a first time period (e.g., the predetermined diagnosis period) and at least one instance of filling at least one prescription for medication during a second time period (e.g., the predetermined medication period). As has been discussed, based on an assumption that the provision of medication would be based on an earlier made diagnosis, the first time period may be longer so as to reach further back into time than the second time period.

At 2122, the processor component of the coordinating device may generate a separate set of models for each of multiple diagnosis groups based on correlations identified between diagnosis groups and medication classes identified by the at least one processor component of the at least one node device. More specifically, and as previously discussed, the at least one processor component of the at least one node device may convert specific diagnoses associated with each patient of the first set of patients into a corresponding diagnosis group, and may convert each instance of the provision of a medication to a patient of the first set of patients into an indication of provision of a medication belonging to a medication class. The at least one processor circuit of the at least one node may then generate correlation data (e.g., the correlation data 1333) identifying all of the correlations found between diagnosis groups and medication classes for each patient of the first set of patients, and provide that correlation data to the coordinating device. The processor component of the coordinating device may then use the correlation data in deriving each of the sets of models for each diagnosis group found among the first set of patients.

At 2130, the processor component of the coordinating device may command the at least one processor component of the at least one node device to randomly select a second set of patients with at least one diagnosis of having a medical condition made during the first time period and at least one instance of filling at least one prescription for medication during the second time period. As has been discussed, the processor component of the coordinating device may distribute indications of the identifiers of the patients of the first set of patients to the processor component of the at least one node device to enable the processor component of the at least one node device to avoid including one of the patients of the first set in the second set of patients.

At 2132, the processor component of the coordinating device may select a model of each of the sets of models to be used in detecting suspicious prescription filling patterns based on the results of tests of each of the models in each set of models performed by the at least one processor component of the at least one node device. More specifically, and as previously discussed, the at least one processor component of the at least one node device may use each model of each set of models to make predictions of what diagnosis groups will be found to be associated with each indication of a medication class for which a medication was provided to one of the patients of the second group of patients. The at least one processor component of the at least one node device may then compare the predictions made using each of the models of each of the sets of models to the medication classes for which there are indications of medications having actually been provided to each of the patients of the second set of patients. The at least one processor of the at least one node device may accrue scores of false positives and true positives for each model of each set of models, and provide those prediction results to the coordinating device. The processor component of the coordinating device may then derive measures of prediction accuracy and measures of sensitivity to suspicious prescription filling patterns for each model of each set of models. The processor component of the coordinating device may then use those measures of accuracy and/or sensitivity, along with an indication of available workload capacity for investigating such suspicious patterns, to select one model of each set of models for use in detecting suspicious prescription filling patterns.

Figure 16:
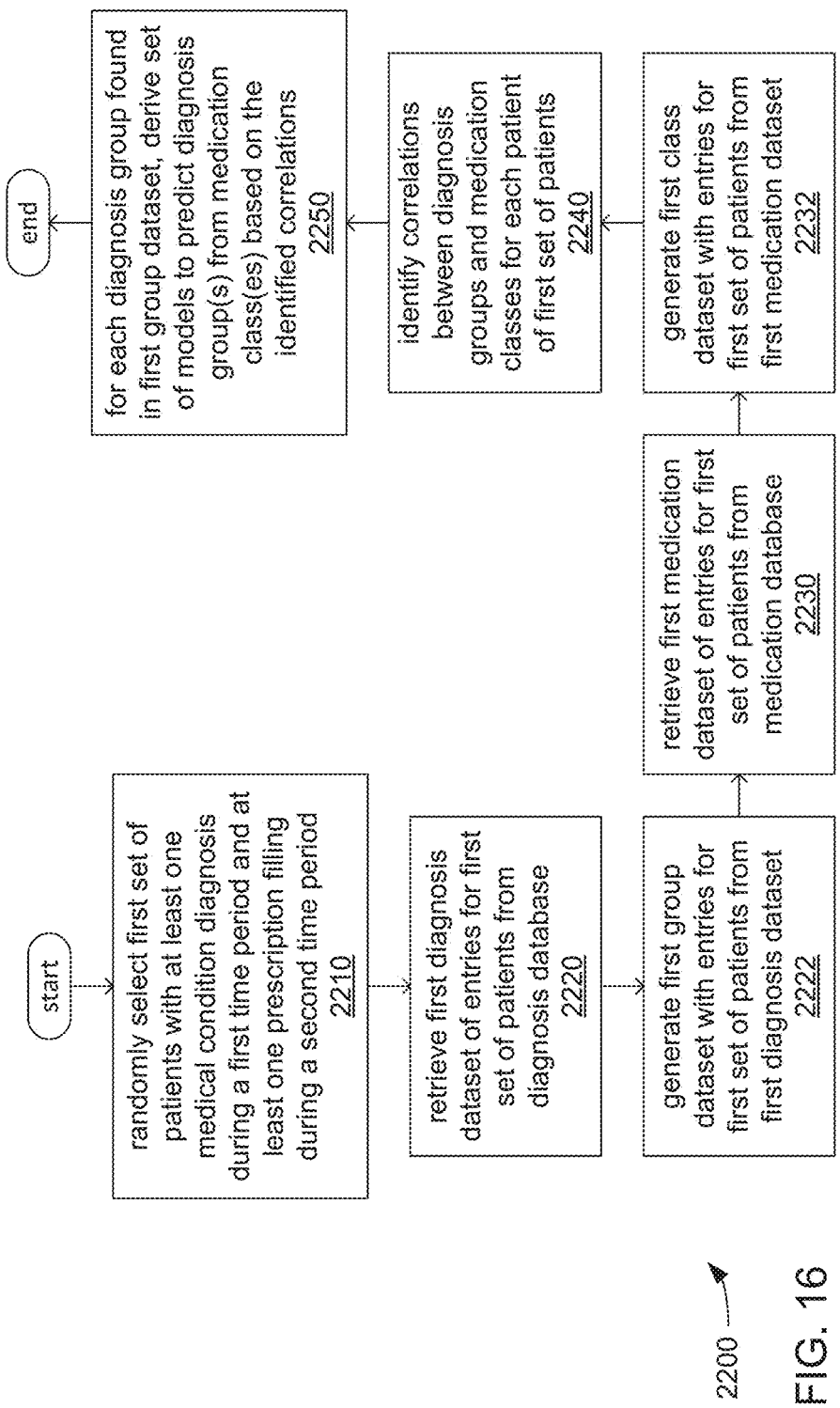
FIG. 16 illustrates an example embodiment of a logic flow of generating models.

FIG. 16 illustrates an example embodiment of a logic flow 2200. The logic flow 2200 may be representative of some or all of the operations executed by one or more embodiments described herein. More specifically, the logic flow 2200 may illustrate operations performed by the processor components 1350 and/or 1450 in executing the control routines 1340 and/or 1440, and/or performed by other component(s) of at least the coordinating device 1400, and/or the one or more node devices 1300.

At 2210, a processor component of a node device (e.g., the processor component 1350 of one of the one or more node devices 1300) may randomly select a first set of patients with at least one diagnosis of having a medical condition made during a first time period (e.g., the predetermined diagnosis period) and at least one instance of filling at least one prescription for medication during a second time period (e.g., the predetermined medication period). As has been discussed, this may be in response to the receipt of a command transmitted by a processor component of a coordinating device (e.g., the processor component 1450 of the coordinating device 1400) to perform a portion of operations to generate sets of models for use in detecting suspicious prescription filling patterns.

At 2220, the processor component of the node device may access a diagnosis database (e.g., the diagnosis database 1130) to retrieve a subset of the patient diagnosis records stored therein that are each associated with a patient of the first set of patients, thereby creating a first diagnosis dataset. At 2222, the processor component of the node device may convert the indications of diagnoses made during the first time period within each patient diagnosis record of the first diagnosis dataset to corresponding indications of diagnoses groups for which diagnoses were made during the first time period within corresponding diagnosis group records of a first group dataset, thereby generating the first group dataset. As previously discussed, such a conversion may entail the use of diagnosis grouping data (e.g., the diagnosis grouping data 1431) that sets forth the manner in which numerous diagnoses are categorized into diagnosis groups defined by experts in the medical field, such as medical experts of the CDC.

At 2230, the processor component of the node device may access a medication database (e.g., the medication database 1230) to retrieve a subset of the patient medication records stored therein that are each associated with a patient of the first set of patients, thereby creating a first medication dataset that corresponds to the diagnosis dataset in that each covers the same first set of patients. At 2232, the processor component of the node device may convert the indications of medications provided during the second time period within each patient medication record of the first medication dataset to corresponding indications of medication classes for which medications were provided during the second time period within corresponding medication class records of a first class dataset, thereby generating the first class dataset. As previously discussed, such a conversion may entail the use of drug classification data (e.g., the drug classification data 1432) that sets forth the manner in which numerous medications are organized into medication classes defined by experts in the medical field, such as medical experts of the WHO.

At 2240, the processor component of the node device may, for each diagnosis group record of the first group dataset and each medication class record of the first class dataset that corresponds by patient, identify at least one correlation between at least one indication of a diagnosis group and at least one indication of a medication class. The processor component of the node device may then transmit correlation data indicating the identified correlations (e.g., the correlation data 1333) to the coordinating device.

At 2250, the processor component of the coordinating device may generate a separate set of models (e.g., the sets of models 1434) for each of the diagnosis groups found in the first group dataset based on the identified correlations, where each model within each set of models correlates at least one medication class to the diagnosis group that is associated with that set of models. As previously discussed, each of the models within each set of models may be of a different model type (e.g., a decision tree model, a regression model, a neural network model, etc.).

Figure 17:
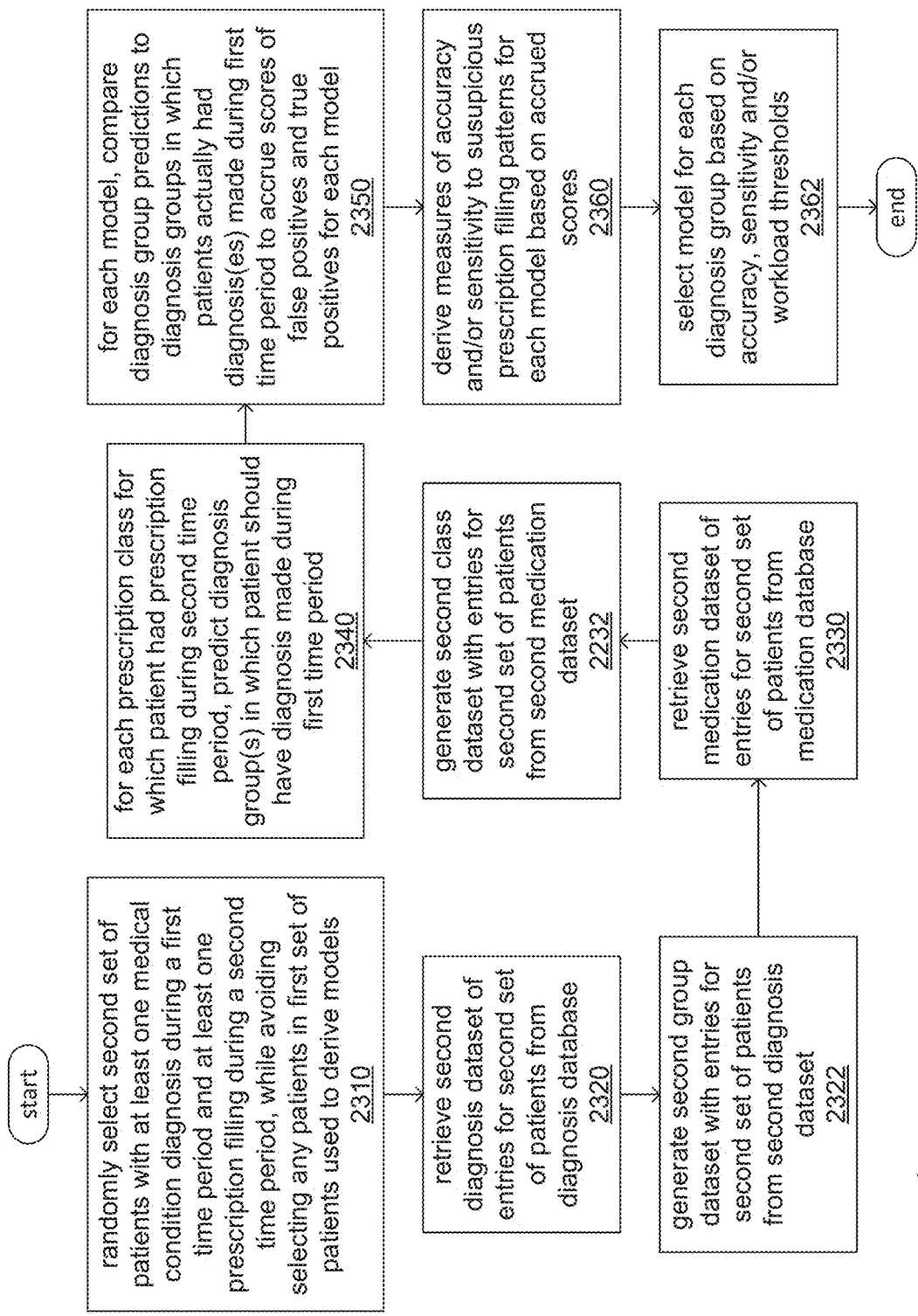
FIG. 17 illustrates an example embodiment of a logic flow of testing and selecting models.

FIG. 17 illustrates an example embodiment of a logic flow 2300. The logic flow 2300 may be representative of some or all of the operations executed by one or more embodiments described herein. More specifically, the logic flow 2300 may illustrate operations performed by the processor components 1350 and/or 1450 in executing the control routines 1340 and/or 1440, and/or performed by other component(s) of at least the coordinating device 1400, and/or the one or more node devices 1300.

At 2310, a processor component of a node device (e.g., the processor component 1350 of one of the one or more node devices 1300) may randomly select a second set of patients with at least one diagnosis of having a medical condition made during a first time period (e.g., the predetermined diagnosis period) and at least one instance of filling at least one prescription for medication during a second time period (e.g., the predetermined medication period). As the processor component of the node device does so, the processor component may avoid including in the second set of patients any patients of an earlier first set used to generate sets of models for use in detecting suspicious prescription filling patterns. As has been discussed, the processor component of the node device may perform these operations in response to the receipt of a command transmitted by a processor component of a coordinating device (e.g., the processor component 1450 of the coordinating device 1400) to perform a portion of operations to test the sets of models.

At 2320, the processor component of the node device may access a diagnosis database (e.g., the diagnosis database 1130) to retrieve a subset of the patient diagnosis records stored therein that are each associated with a patient of the second set of patients, thereby creating a second diagnosis dataset. At 2322, the processor component of the node device may convert the indications of diagnoses made during the first time period within each patient diagnosis record of the second diagnosis dataset to corresponding indications of diagnoses groups for which diagnoses were made during the first time period within corresponding diagnosis group records of a second group dataset, thereby generating the second group dataset.

At 2330, the processor component of the node device may access a medication database (e.g., the medication database 1230) to retrieve a subset of the patient medication records stored therein that are each associated with a patient of the second set of patients, thereby creating a second medication dataset that corresponds to the diagnosis dataset in that each covers the same second set of patients. At 2332, the processor component of the node device may convert the indications of medications provided during the second time period within each patient medication record of the second medication dataset to corresponding indications of medication classes for which medications were provided during the second time period within corresponding medication class records of a second class dataset, thereby generating the second class dataset.

At 2340, the processor component of the node device may use each model of each set of models to make predictions of what diagnosis groups will be found in each diagnosis group record based on the indication(s) of medication class(es) in each medication class record that corresponds by patient of the second set of patients. At 2350, the processor component of the node device may then compare the predictions of medication classes made using each of the models of each of the sets of models to the medication classes for which there are indications of medications having actually been provided to each of the patients of the second set of patients. In so doing, the processor component of the node device may accrue scores of false positives and true positives for each model of each set of models, and provide those prediction results to the coordinating device.

At 2360, the processor component of the coordinating device may then derive measures of prediction accuracy and/or sensitivity to suspicious prescription filling patterns for each model of each set of models. At 2362, the processor component of the coordinating device may then use those measures of accuracy and/or sensitivity, along with an indication of available workload capacity for investigating such suspicious patterns, to select one model of each set of models for use in detecting suspicious prescription filling patterns. Again, in some embodiments, for one or more of the diagnosis groups, there may be found to be no model that meets one or more thresholds for accuracy and/or sensitivity (and/or other measures of degree of effectiveness) such that there may be no model selected to correlate medication class(es) to those one or more diagnosis groups.

Some systems may use Hadoop®, an open-source framework for storing and analyzing big data in a distributed computing environment. Some systems may use cloud computing, which can enable ubiquitous, convenient, on-demand network access to a shared pool of configurable computing resources (e.g., networks, servers, storage, applications and services) that can be rapidly provisioned and released with minimal management effort or service provider interaction. Some grid systems may be implemented as a multi-node Hadoop® cluster, as understood by a person of skill in the art. Apache™ Hadoop® is an open-source software framework for distributed computing.

What has been described above includes examples of the disclosed architecture. It is, of course, not possible to describe every conceivable combination of components and/or methodologies, but one of ordinary skill in the art may recognize that many further combinations and permutations are possible. Accordingly, the novel architecture is intended to embrace all such alterations, modifications and variations that fall within the spirit and scope of the appended claims.

The invention claimed is:

1. An apparatus comprising a processor component and a storage to store instructions that, when executed by the processor component, cause the processor component to:
retrieve, from a diagnosis database, patient diagnosis records of a training set of patients and a testing set of patients;
for each patient diagnosis record associated with a patient of the training set or the testing set that includes at least one indication of a diagnosis made within a first time period, perform operations comprising:
generate a corresponding diagnosis group record;
correlate each diagnosis indicated in the patient diagnosis record as made within the first time period to a diagnosis group; and
for each diagnosis group correlated to at least one diagnosis indicated as made within the first time period, generate in the corresponding diagnosis group record an indication of at least one diagnosis in the diagnosis group made within the first time period;
retrieve, from a medication database, patient medication records of the training set and the testing set;
for each patient medication record associated with a patient of the training set or the testing set that includes at least one indication of at least one medication provided to the patient within a second time period, perform operations comprising:
generate a corresponding medication class record;
correlate each medication indicated in the patient medication record as provided to the patient within the second time period to a medication class; and
for each medication class correlated to at least one medication indicated as provided to the patient within the second time period, generate in the corresponding medication class record an indication of at least one medication in the medication class provided to the patient within the second time period;
for each patient of the training set of patients for which a corresponding diagnosis group record is generated and for which a corresponding medication class record is generated, identify at least one correlation between at least one diagnosis group and at least one medication class;
for each diagnosis group for which at least one correlation is identified, train a set of models that correlate the diagnosis group to at least one medication class based on the at least one identified correlation, wherein each model of the set of models comprises a neural network; and
for each patient of the testing set of patients for which a corresponding diagnosis group record is generated and

49 for which a corresponding medication class record is generated, perform operations comprising:
employ each model of each set of models to make at least one prediction of at least one diagnosis group as indicated in the corresponding diagnosis group record based on at least one medication class indicated in the corresponding medication class record;
compare the at least one prediction to the corresponding diagnosis group record to derive a tally of at least one of true positives or false positives for each prediction; and
for each diagnosis group for which a set of models is trained, select one model of the set of models based on the tally of at least one of true positives or false positives of each model of the set of models.

2. The apparatus of claim 1, wherein:
the diagnosis database comprises a table wherein each patient diagnosis record comprises a row;
each row of the diagnosis database comprises at least one Boolean flag indicating whether a diagnosis is made;
generation of a diagnosis group record comprises an addition of a row that corresponds to a row of the diagnosis database to a table of a group dataset;
each row of the group dataset comprises at least one Boolean flag indicating a whether a diagnosis in a diagnosis group was made within the first time period;
the medication database comprises a table wherein each patient medication record comprises a row;
each row of the medication database comprises at least one count of instances in which a medication is provided to a patient;
generation of a patient class record comprises an addition of a row that corresponds to a row of the medication database to a table of a class dataset; and
each row of the class dataset comprises at least one count of instances in which a medication of a medication class was provided to the patient within the second time period.

3. The apparatus of claim 1, wherein the processor component is caused to, for each diagnosis group for which a set of models is trained, perform operations comprising:
calculate at least one of a measure of sensitivity or a measure of accuracy for each model of the set of models based on the tally of at least one of the true positives and the false positives; and
select one model of the set of models based at least on the measure of sensitivity or the measure of accuracy.

4. The apparatus of claim 3, wherein the measure of accuracy is evaluated based on at least one of a Kolmogorov-Smirnov test, a misclassification rate or an average-square error.

5. The apparatus of claim 3, wherein the processor component is caused to, for each diagnosis group for which a set of models is trained, perform operations comprising:
determine whether at least one model of the set of models meets a threshold of at least one of sensitivity or accuracy; and
condition the selection of the one model on a determination that at least one model of the set of models meets the threshold.

6. The apparatus of claim 3, wherein the processor component is caused to perform operations comprising:
retrieve, from the diagnosis database, patient diagnosis records of a third in-use set of patients;

50 for each patient diagnosis record associated with a patient of the in-use set that includes at least one indication of a diagnosis made within a first time period, perform operations comprising:
generate a corresponding diagnosis group record;
correlate each diagnosis indicated in the patient diagnosis record as made within the first time period to a diagnosis group; and
for each diagnosis group correlated to at least one diagnosis indicated as made within the first time period, generate in the corresponding diagnosis group record an indication of at least one diagnosis in the diagnosis group made within the first time period;
retrieve, from the medication database, patient medication records of the in-use set;
for each patient medication record associated with a patient of the in-use set that includes at least one indication of at least one medication provided to the patient within a second time period, perform operations comprising:
generate a corresponding medication class record;
correlate each medication indicated in the patient medication record as provided to the patient within the second time period to a medication class; and
for each medication class correlated to at least one medication indicated as provided to the patient within the second time period, generate in the corresponding medication class record an indication of at least one medication in the medication class provided to the patient within the second time period;
for each patient of the in-use set of patients for which a corresponding diagnosis group record is generated and for which a corresponding medication class record is generated, perform operations comprising:
employ each selected model of each set of models for which a model is selected to make at least one determination of at least one diagnosis group that should be indicated in the corresponding diagnosis group record based on at least one medication class indicated in the corresponding medication class record; and
compare the at least one determination to the corresponding diagnosis group record to derive a tally of at least one of matches or mismatches for at least one of each patient of the in-use set or each pharmacy that provides at least one medication to a patient of the in-use set.

7. The apparatus of claim 6, wherein the processor component is caused to present an indication of a patient identified by a selected model as having been provided at least one medication of a medication class within the second time period, but not having a diagnosis in a diagnosis group made within the first time period that the model determined should have been made.

8. The apparatus of claim 6, wherein the processor component is caused to present an indication of a pharmacy as having provided medications to a plurality of patients of the third set, wherein:
each patient of the plurality of patients is identified by a selected model as having been provided at least one medication of a medication class within the second time period, but not having a diagnosis in a diagnosis group made within the first time period that the model determined should have been made; and the plurality of patients exceeds in number a predetermined threshold of patients so identified.

9. The apparatus of claim 1, wherein the first time period comprises 24 months and the second time period comprises 12 months.

10. A non-transitory machine-readable storage medium having tangibly embodied thereon a computer-program product including instructions operable to cause a processor component to perform operations including:
retrieve, from a diagnosis database, patient diagnosis records of a training set of patients and a testing set of patients;
for each patient diagnosis record associated with a patient of the training set or the testing set that includes at least one indication of a diagnosis made within a first time period, perform operations including:
generate a corresponding diagnosis group record;
correlate each diagnosis indicated in the patient diagnosis record as made within the first time period to a diagnosis group; and
for each diagnosis group correlated to at least one diagnosis indicated as made within the first time period, generate in the corresponding diagnosis group record an indication of at least one diagnosis in the diagnosis group made within the first time period;
retrieve, from a medication database, patient medication records of the training set and the testing set;
for each patient medication record associated with a patient of the training set or the testing set that includes at least one indication of at least one medication provided to the patient within a second time period, perform operations including:
generate a corresponding medication class record;
correlate each medication indicated in the patient medication record as provided to the patient within the second time period to a medication class; and
for each medication class correlated to at least one medication indicated as provided to the patient within the second time period, generate in the corresponding medication class record an indication of at least one medication in the medication class provided to the patient within the second time period;
for each patient of the training set of patients for which a corresponding diagnosis group record is generated and for which a corresponding medication class record is generated, identify at least one correlation between at least one diagnosis group and at least one medication class;
for each diagnosis group for which at least one correlation is identified, train a set of models that correlate the diagnosis group to at least one medication class based on the at least one identified correlation, wherein each model of the set of models comprises a neural network; and
for each patient of the testing set of patients for which a corresponding diagnosis group record is generated and for which a corresponding medication class record is generated, perform operations including:
employ each model of each set of models to make at least one prediction of at least one diagnosis group as indicated in the corresponding diagnosis group record based on at least one medication class indicated in the corresponding medication class record;
compare the at least one prediction to the corresponding diagnosis group record to derive a tally of at least one of true positives or false positives for each prediction; and
for each diagnosis group for which a set of models is trained, select one model of the set of models based on the tally of at least one of true positives or false positives of each model of the set of models.

11. The storage medium of claim 10, wherein:
the diagnosis database comprises a table wherein each patient diagnosis record comprises a row;
each row of the diagnosis database comprises at least one Boolean flag indicating whether a diagnosis is made;
generating a diagnosis group record comprises adding a row that corresponds to a row of the diagnosis database to a table of a group dataset;
each row of the group dataset comprises at least one Boolean flag indicating a whether a diagnosis in a diagnosis group was made within the first time period;
the medication database comprises a table wherein each patient medication record comprises a row;
each row of the medication database comprises at least one count of instances in which a medication is provided to a patient;
generating a patient class record comprises adding a row that corresponds to a row of the medication database to a table of a class dataset; and
each row of the class dataset comprises at least one count of instances in which a medication of a medication class was provided to the patient within the second time period.

12. The storage medium of claim 10, wherein the processor component is caused to, for each diagnosis group for which a set of models is trained, perform operations including:
calculate at least one of a measure of sensitivity or a measure of accuracy for each model of the set of models based on the tally of at least one of the true positives and the false positives; and
select one model of the set of models based at least on the measure of sensitivity or the measure of accuracy.

13. The storage medium of claim 12, wherein the measure of accuracy is evaluated based on at least one of a Kolmogorov-Smirnov test, a misclassification rate or an average-square error.

14. The storage medium of claim 12, wherein the processor component is caused to, for each diagnosis group for which a set of models is trained, perform operations including:
determine whether at least one model of the set of models meets a threshold of at least one of sensitivity or accuracy; and
condition the selection of the one model on a determination that at least one model of the set of models meets the threshold.

15. The storage medium of claim 12, wherein the processor component is caused to perform operations including:
retrieve, from the diagnosis database, patient diagnosis records of in-use set of patients;
for each patient diagnosis record associated with a patient of the in-use set that includes at least one indication of a diagnosis made within a first time period, perform operations including:
generate a corresponding diagnosis group record;
correlate each diagnosis indicated in the patient diagnosis record as made within the first time period to a diagnosis group; and for each diagnosis group correlated to at least one diagnosis indicated as made within the first time period, generate in the corresponding diagnosis group record an indication of at least one diagnosis in the diagnosis group made within the first time period;

retrieve, from the medication database, patient medication records of the in-use set;

for each patient medication record associated with a patient of the in-use set that includes at least one indication of at least one medication provided to the patient within a second time period, perform operations including:

generate a corresponding medication class record;

correlate each medication indicated in the patient medication record as provided to the patient within the second time period to a medication class; and for each medication class correlated to at least one medication indicated as provided to the patient within the second time period, generate in the corresponding medication class record an indication of at least one medication in the medication class provided to the patient within the second time period;

for each patient of the in-use set of patients for which a corresponding diagnosis group record is generated and for which a corresponding medication class record is generated, perform operations including:

employ each selected model of each set of models for which a model is selected to make at least one determination of at least one diagnosis group that should be indicated in the corresponding diagnosis group record based on at least one medication class indicated in the corresponding medication class record; and compare the at least one determination to the corresponding diagnosis group record to derive a tally of at least one of matches or mismatches for at least one of each patient of the in-use set or each pharmacy that provides at least one medication to a patient of the in-use set.

16. The storage medium of claim 15, wherein the processor component is caused to present an indication of a patient identified by a selected model as having been provided at least one medication of a medication class within the second time period, but not having a diagnosis in a diagnosis group made within the first time period that the model determined should have been made.

17. The storage medium of claim 15, wherein the processor component is caused to present an indication of a pharmacy as having provided medications to a plurality of patients of the third set, wherein:

each patient of the plurality of patients is identified by a selected model as having been provided at least one medication of a medication class within the second time period, but not having a diagnosis in a diagnosis group made within the first time period that the model determined should have been made; and the plurality of patients exceeds in number a predetermined threshold of patients so identified.

18. The storage medium of claim 10, wherein the first time period comprises 24 months and the second time period comprises 12 months.

19. A computer-implemented method comprising:

retrieving, from a diagnosis database, patient diagnosis records of a training set of patients and a testing set of patients;

for each patient diagnosis record associated with a patient of the training set or the testing set that includes at least one indication of a diagnosis made within a first time period, performing operations comprising:

generating a corresponding diagnosis group record;

correlating each diagnosis indicated in the patient diagnosis record as made within the first time period to a diagnosis group; and for each diagnosis group correlated to at least one diagnosis indicated as made within the first time period, generating in the corresponding diagnosis group record an indication of at least one diagnosis in the diagnosis group made within the first time period;

retrieving, from a medication database, patient medication records of the training set and the testing set;

for each patient medication record associated with a patient of the training set or the testing set that includes at least one indication of at least one medication provided to the patient within a second time period, performing operations comprising:

generating a corresponding medication class record;

correlating each medication indicated in the patient medication record as provided to the patient within the second time period to a medication class; and for each medication class correlated to at least one medication indicated as provided to the patient within the second time period, generating in the corresponding medication class record an indication of at least one medication in the medication class provided to the patient within the second time period;

for each patient of the training set of patients for which a corresponding diagnosis group record is generated and for which a corresponding medication class record is generated, identifying at least one correlation between at least one diagnosis group and at least one medication class;

for each diagnosis group for which at least one correlation is identified, training a set of models that correlate the diagnosis group to at least one medication class based on the at least one identified correlation, wherein each model of the set of models comprises a neural network; and for each patient of the testing set of patients for which a corresponding diagnosis group record is generated and for which a corresponding medication class record is generated, performing operations comprising:

employing each model of each set of models to make at least one prediction of at least one diagnosis group as indicated in the corresponding diagnosis group record based on at least one medication class indicated in the corresponding medication class record;

comparing the at least one prediction to the corresponding diagnosis group record to derive a tally of at least one of true positives or false positives for each prediction; and for each diagnosis group for which a set of models is trained, selecting one model of the set of models based on the tally of at least one of true positives or false positives of each model of the set of models.

20. The computer-implemented method of claim 19, wherein the diagnosis database comprises a table wherein each patient diagnosis record comprises a row;

each row of the diagnosis database comprises at least one Boolean flag indicating whether a diagnosis is made;

generating a diagnosis group record comprises adding a row that corresponds to a row of the diagnosis database to a table of a group dataset;

each row of the group dataset comprises at least one Boolean flag indicating a whether a diagnosis in a diagnosis group was made within the first time period;

the medication database comprises a table wherein each patient medication record comprises a row;

each row of the medication database comprises at least one count of instances in which a medication is provided to a patient;

generating a patient class record comprises adding a row that corresponds to a row of the medication database to a table of a class dataset; and each row of the class dataset comprises at least one count of instances in which a medication of a medication class was provided to the patient within the second time period.

21. The computer-implemented method of claim 19, comprising, for each diagnosis group for which a set of models is trained, performing operations comprising:

calculating at least one of a measure of sensitivity or a measure of accuracy for each model of the set of models based on the tally of at least one of the true positives and the false positives; and selecting one model of the set of models based at least on the measure of sensitivity or the measure of accuracy.

22. The computer-implemented method of claim 21, wherein the measure of accuracy is evaluated based on at least one of a Kolmogorov-Smirnov test, a misclassification rate or an average-square error.

23. The computer-implemented method of claim 21, comprising, for each diagnosis group for which a set of models is trained, performing operations comprising:

determining whether at least one model of the set of models meets a threshold of at least one of sensitivity or accuracy; and conditioning the selection of the one model on a determination that at least one model of the set of models meets the threshold.

24. The computer-implemented method of claim 21, comprising performing operations comprising:

retrieving, from the diagnosis database, patient diagnosis records of in-use set of patients;

for each patient diagnosis record associated with a patient of the in-use set that includes at least one indication of a diagnosis made within a first time period, performing operations comprising:

generating a corresponding diagnosis group record;

correlating each diagnosis indicated in the patient diagnosis record as made within the first time period to a diagnosis group; and for each diagnosis group correlated to at least one diagnosis indicated as made within the first time period, generating in the corresponding diagnosis group record an indication of at least one diagnosis in the diagnosis group made within the first time period;

retrieving, from the medication database, patient medication records of the in-use set;

for each patient medication record associated with a patient of the in-use set that includes at least one indication of at least one medication provided to the patient within a second time period, performing operations comprising:

generating a corresponding medication class record;

correlating each medication indicated in the patient medication record as provided to the patient within the second time period to a medication class; and for each medication class correlated to at least one medication indicated as provided to the patient within the second time period, generating in the corresponding medication class record an indication of at least one medication in the medication class provided to the patient within the second time period;

for each patient of the in-use set of patients for which a corresponding diagnosis group record is generated and for which a corresponding medication class record is generated, performing operations comprising:

employing each selected model of each set of models for which a model is selected to make at least one determination of at least one diagnosis group that should be indicated in the corresponding diagnosis group record based on at least one medication class indicated in the corresponding medication class record; and comparing the at least one determination to the corresponding diagnosis group record to derive a tally of at least one of matches or mismatches for at least one of each patient of the in-use set or each pharmacy that provides at least one medication to a patient of the in-use set.

25. The computer-implemented method of claim 24, comprising presenting an indication of a patient identified by a selected model as having been provided at least one medication of a medication class within the second time period, but not having a diagnosis in a diagnosis group made within the first time period that the model determined should have been made.

26. The computer-implemented method of claim 24, comprising presenting an indication of a pharmacy as having provided medications to a plurality of patients of the third set, wherein:

each patient of the plurality of patients is identified by a selected model as having been provided at least one medication of a medication class within the second time period, but not having a diagnosis in a diagnosis group made within the first time period that the model determined should have been made; and the plurality of patients exceeds in number a predetermined threshold of patients so identified.

27. The computer-implemented method of claim 19, wherein the first time period comprises 24 months and the second time period comprises 12 months.

* * * * *